United States Patent
Yamamoto et al.

(10) Patent No.: US 7,144,401 B2
(45) Date of Patent: Dec. 5, 2006

(54) SUTURING DEVICE FOR ENDOSCOPE

(75) Inventors: Tetsuya Yamamoto, Hidaka (JP); Sydney Sheung Chee Chung, Hong Kong (HK); Koichi Kawashima, Hachioji (JP); Junichi Muramatsu, Akiruno (JP); Keita Suzuki, Hachioji (JP); Yoshio Onuki, Hino (JP); Yoshihiko Sugi, Hachioji (JP); Tsukasa Kobayashi, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 10/162,640

(22) Filed: Jun. 6, 2002

(65) Prior Publication Data

US 2002/0198542 A1 Dec. 26, 2002

Related U.S. Application Data

(60) Provisional application No. 60/296,111, filed on Jun. 7, 2001.

(51) Int. Cl.
*A61B 17/04* (2006.01)
(52) U.S. Cl. ..................................................... 606/144
(58) Field of Classification Search ................ 606/144, 606/139, 145, 146, 147, 148
See application file for complete search history.

(56) References Cited

U.S. PATENT DOCUMENTS

| | | | | |
|---|---|---|---|---|
| 3,901,244 A | * | 8/1975 | Schweizer | 606/145 |
| 4,440,171 A | * | 4/1984 | Nomoto et al. | 606/145 |
| 5,037,433 A | | 8/1991 | Wilk et al. | 606/139 |
| 5,350,385 A | * | 9/1994 | Christy | 606/139 |
| 5,364,408 A | * | 11/1994 | Gordon | 606/144 |
| 5,496,331 A | * | 3/1996 | Xu et al. | 606/139 |
| 5,520,703 A | * | 5/1996 | Essig et al. | 606/148 |
| 5,700,273 A | * | 12/1997 | Buelna et al. | 606/148 |
| 5,860,992 A | * | 1/1999 | Daniel et al. | 606/145 |
| 5,911,727 A | * | 6/1999 | Taylor | 606/145 |
| 5,993,466 A | * | 11/1999 | Yoon | 606/147 |
| 6,048,351 A | * | 4/2000 | Gordon et al. | 606/144 |
| 6,443,962 B1 | * | 9/2002 | Gaber | 606/144 |

* cited by examiner

*Primary Examiner*—Eduardo C. Robert
*Assistant Examiner*—Jessica R. Baxter
(74) *Attorney, Agent, or Firm*—Frishauf, Holtz, Goodman & Chick, P.C.

(57) ABSTRACT

A suturing device for an endoscope includes a curved needle rotatably attached on the distal end of the suturing device. A rotary member is provided on the rotation axis of the curved needle for rotating said curved needle and a connecting arm connects the curved needle to the rotary member. The center of curvature of the curved needle is aligned with the rotation axis of the curved needle and engaging means are provided at least at the pointed end of the curved needle for receiving thread.

16 Claims, 87 Drawing Sheets

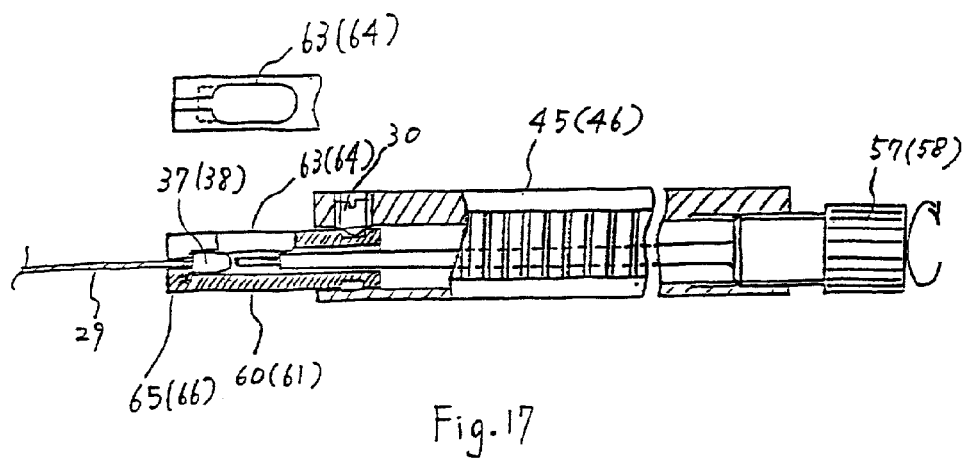
Fig. 17
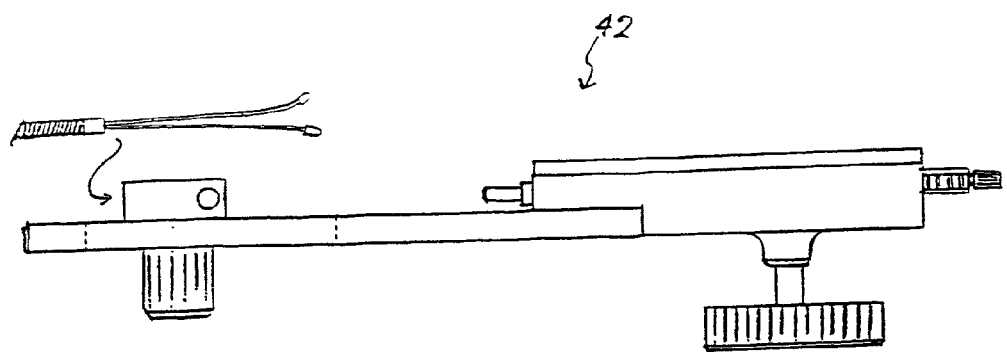
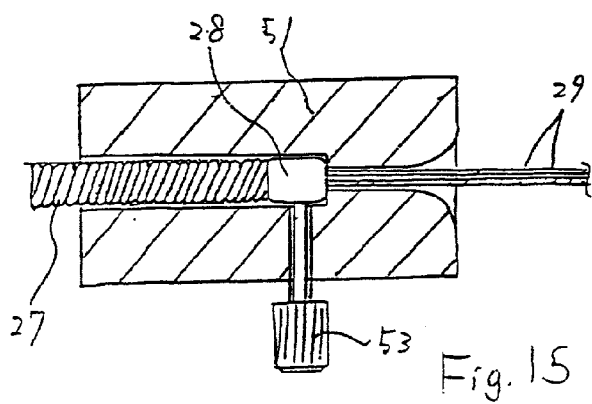
Fig. 15

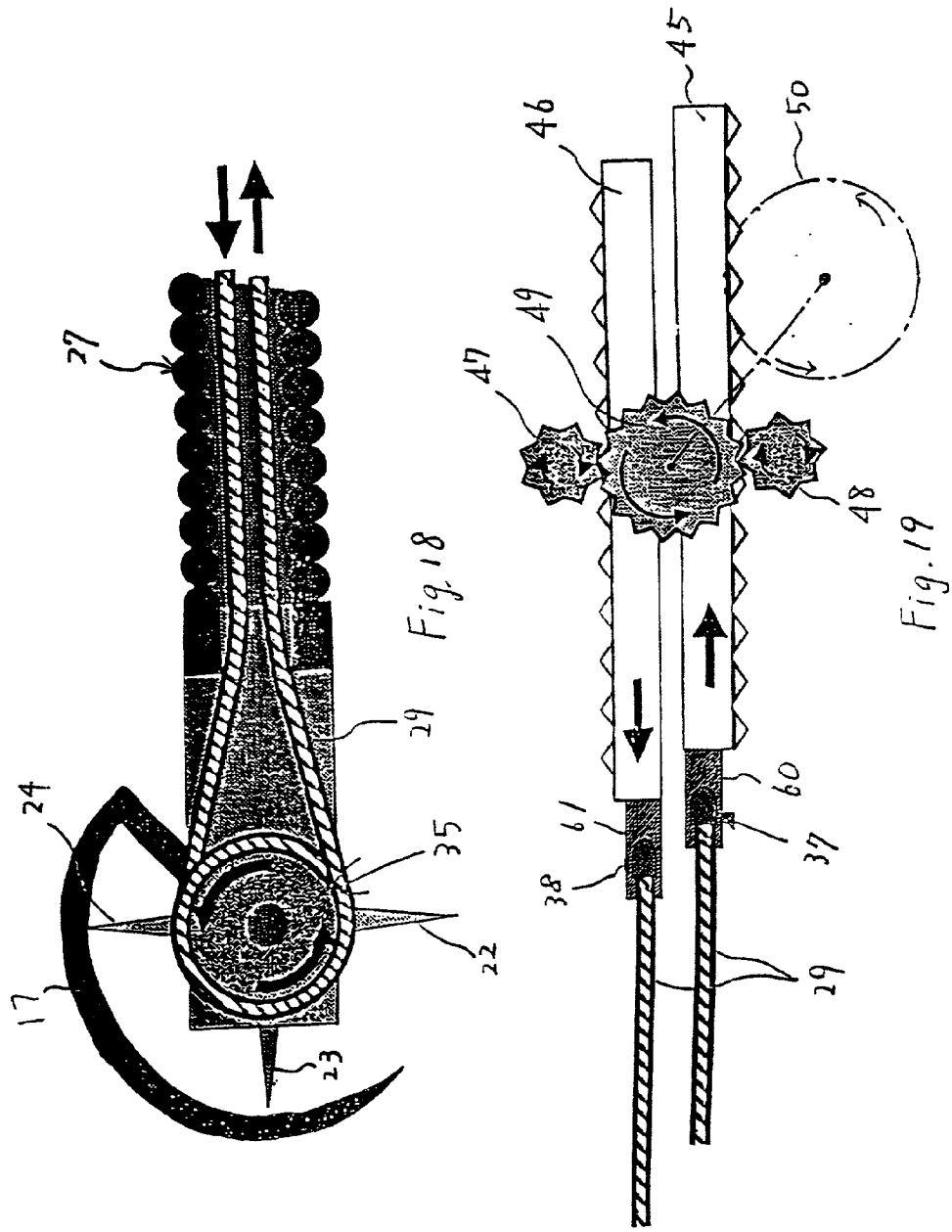

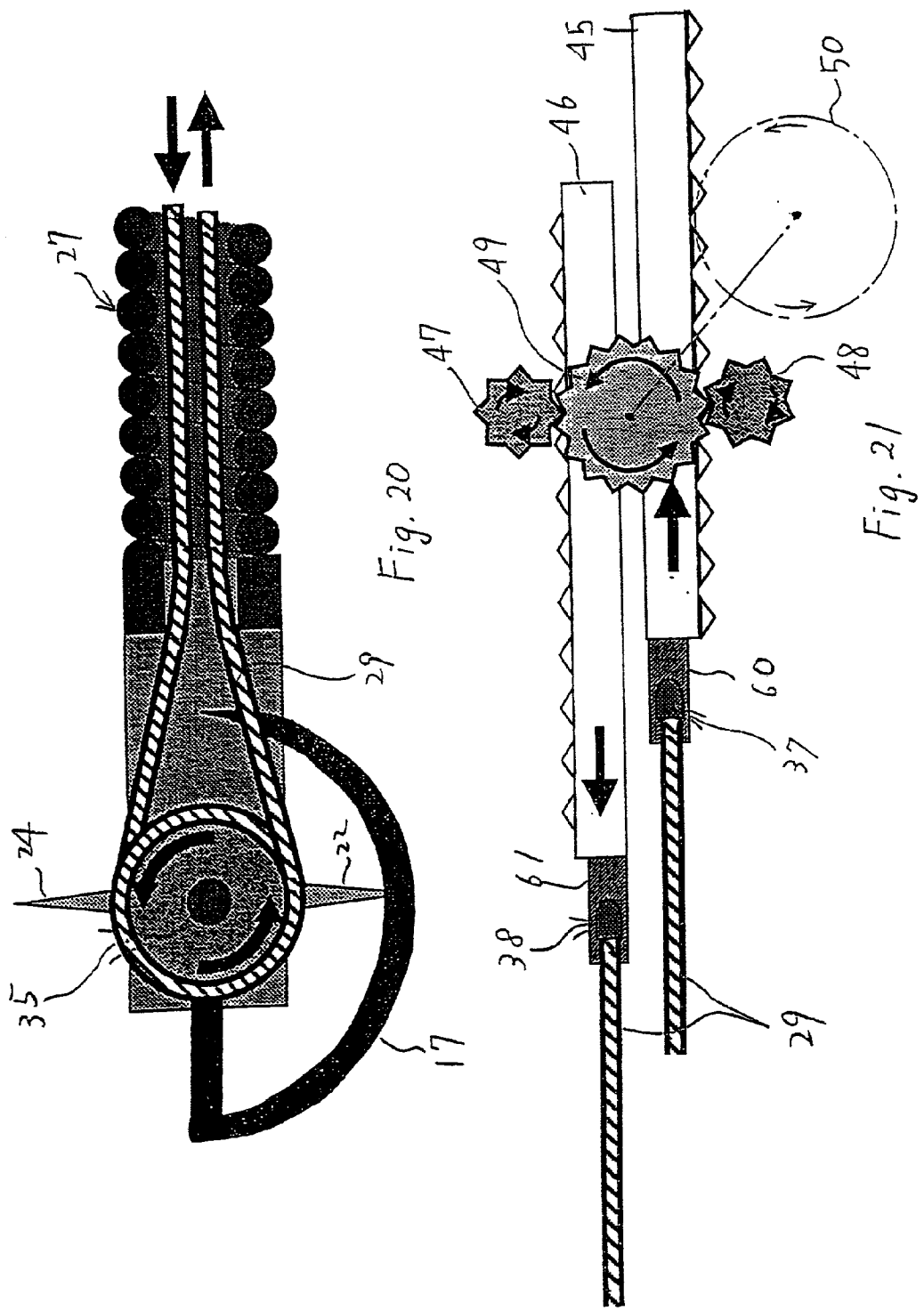

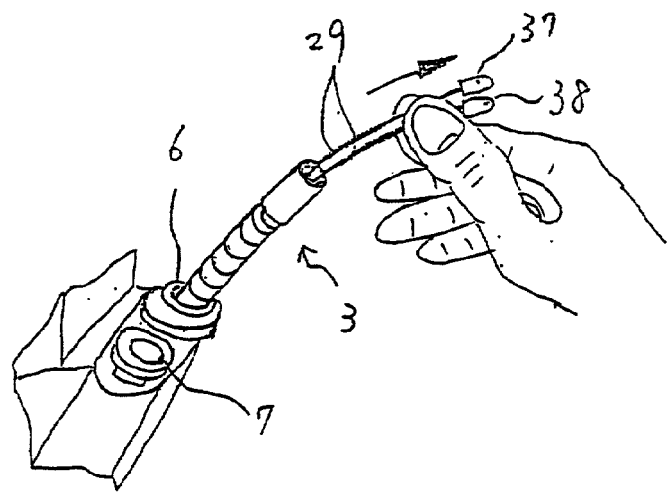
Fig. 35
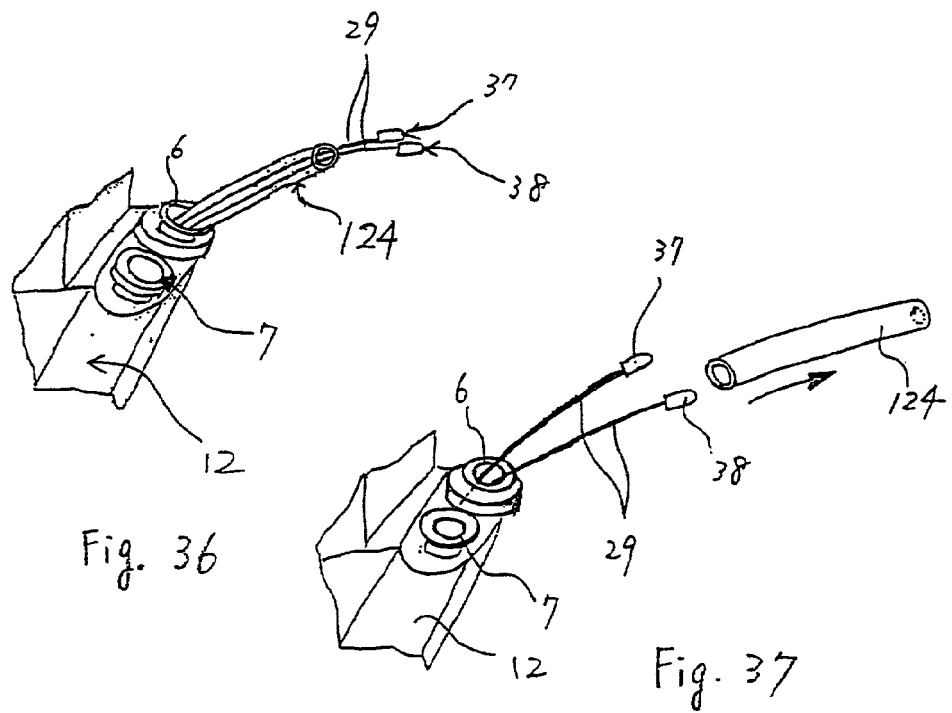
Fig. 36
Fig. 37

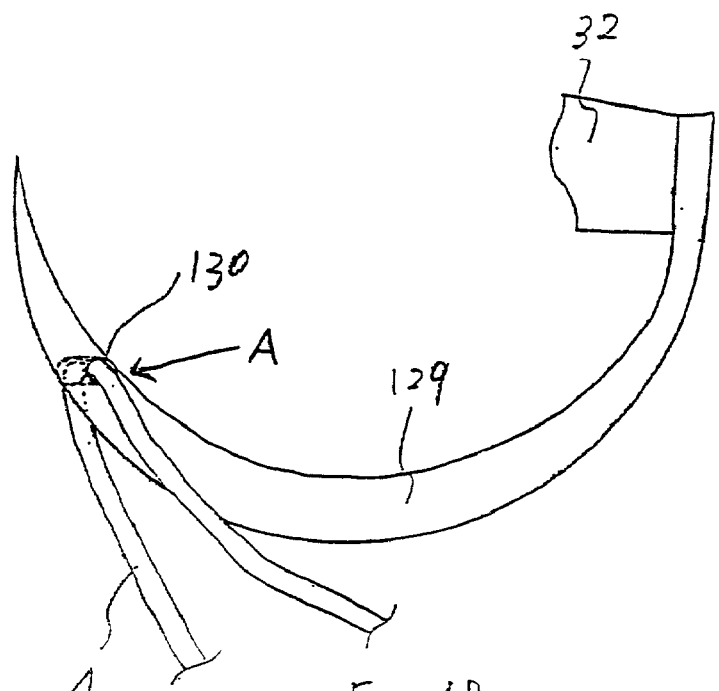
Fig. 48
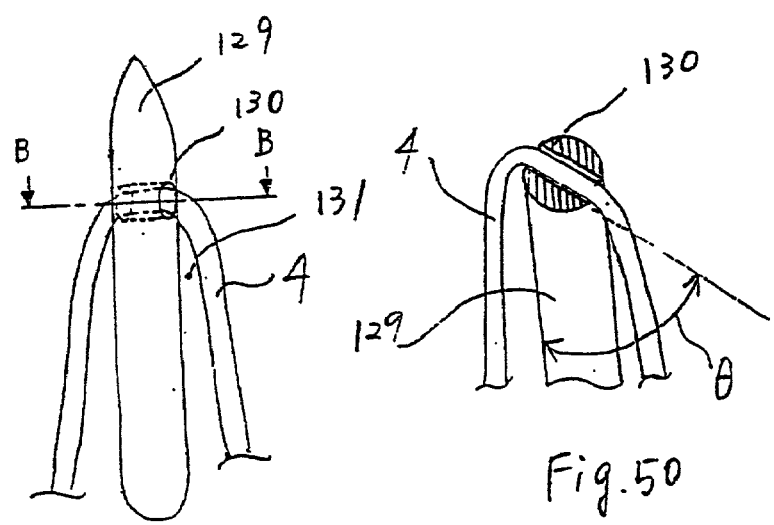
Fig. 49
Fig. 50

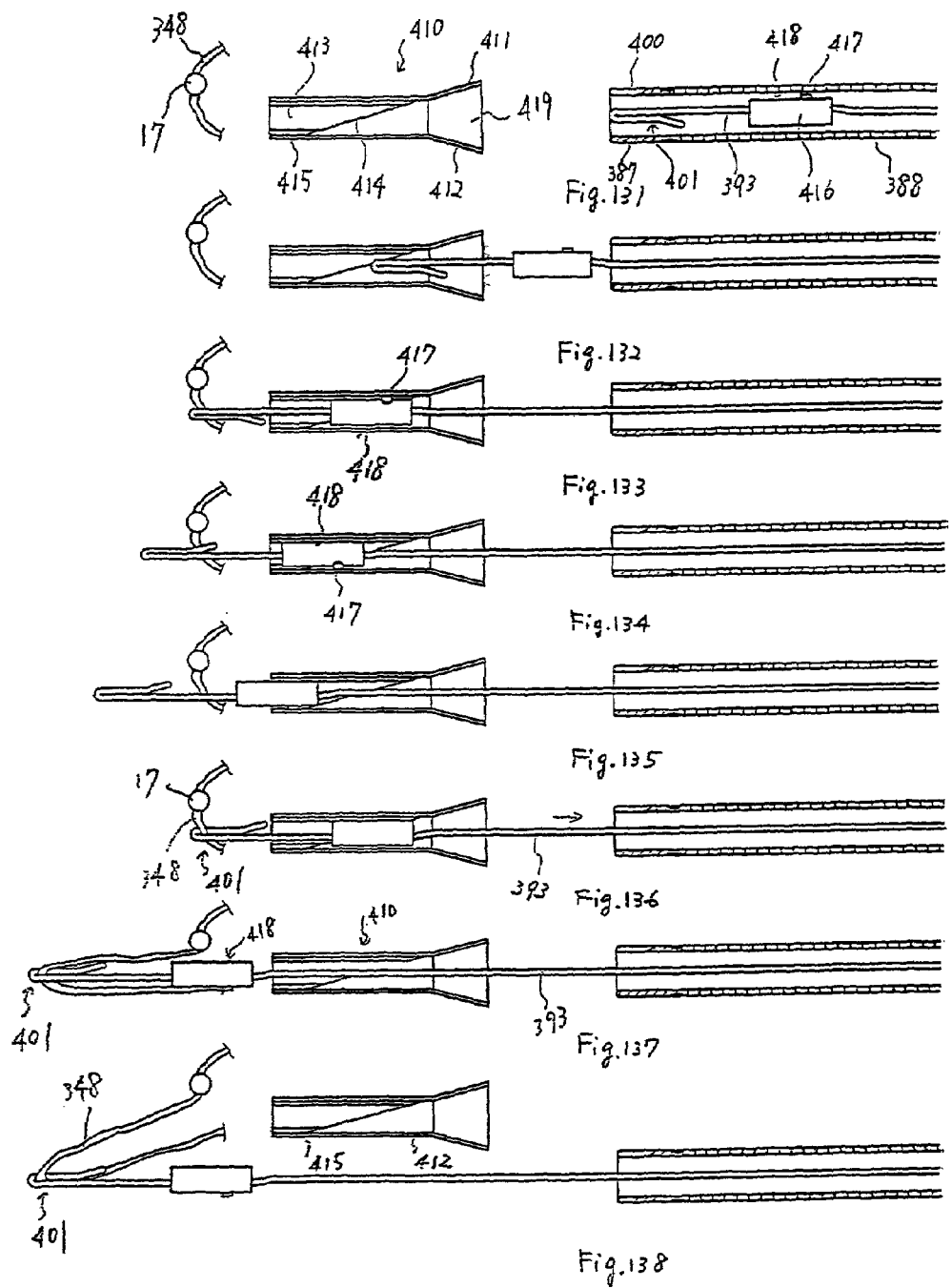

SUTURING DEVICE FOR ENDOSCOPE

CROSS-REFERENCE TO RELATED APPLICATIONS

This application claims the benefit of U.S. Provisional Application to Tetsuya Yamamoto et al, entitled "Suturing Device for Endoscope," application No. 60/296,111, filed Jun. 7, 2001.

BACKGROUND OF THE INVENTION

The present invention relates to a suturing device for suturing using an endoscope for the purpose of hemostasis or for suturing or shunting tissues in body cavities.

In recent years, treatment using endoscopes has been drastically improving to enable various treatment of body organs without large incisions such as in open surgery. Suturing of punctures in body cavities and for hemostasis have become very important techniques among endoscopic treatment, and various methods have been attempted.

U.S. Pat. No. 5,037,433, for example, discloses a construction comprising a flexible endoscope (70) disposed in one of the lumens of an outer tubular member (20), and a forceps instrument (52) having a soft inner tube (32) in another lumen and having a forceps device is in yet another lumen. An elastic and deformable curved needle (44), to which a thread (48) is attached at its operator side, is inserted in its straightened state in the inner tube (32). In order to suture, the curved needle (44) is discharged from the inner tube (32) by pushing push rods (40, 42) which push the curved needle disposed at the distal end side of the inner tube (32) while a wound (66) in a body cavity is sutured by utilizing the force of the curved needle (44) tending toward its original shape.

According to U.S. Pat. No. 5,037,433, however, since the springy curved needle is inserted in a thin inner tube in its straightened state, a decompression force of the springy curved needle works against the inner tube when the curved needle is pushed out of the inner tube by the push rods, the puncture effect of the curved line is degraded and thus the curved needle does not penetrate into the target tissue deeply enough. Since the push rods must have a certain degree of rigidity to push the curved needle out, the outer tube member (20) cannot be curved excessively. In addition, once the needle has punctured the tissue, it cannot be retried, and dislocation of the puncture cannot be corrected.

SUMMARY OF THE INVENTION

In accordance with embodiments of the present invention, a suturing device for endoscope includes a curved needle rotatably attached on the distal end of the suturing device. A rotary member is provided on the rotation axis of the curved needle for rotating the curved needle, and a connecting arm for connecting the curved needle to the rotary member. The center of curvature of the curved needle is aligned with the rotation axis of the curved needle; and engaging means are provided at least at the pointed end of the curved needle for receiving the thread.

The suturing device may include a needle attached on the distal end of the suturing device for suturing, with the engaging means provided at least at the pointed end of the needle for accepting thread and catching means at the distal end side of the suturing device for catching at least a portion of the thread engaged with the engaging means after puncture into tissue.

In addition, the suturing device can have a needle attached on the distal end of the suturing device for suturing and fixing means provided on the distal end side of the suturing device for preventing the suturing device from dislocating from the suturing portion. Furthermore, with a needle attached on the distal end of the suturing device for suturing, fixing means may be provided on the distal end side of the endoscope for preventing the suturing device from dislocating from the suturing portion.

It is also possible for the suturing device to have a needle attached on the distal end of the suturing device for suturing and a thread holding member for detachably holding at least a thread in the vicinity of the trajectory of the needle. In addition, the suturing device with a needle attached on the distal end of the suturing device can include a moving member for moving the needle, wherein at least an operating wire fixed and wound to the moving member for transmitting power is provided and wherein two of the operating wire extend from the proximal end of the endoscope, along with an operating unit for advancing or withdrawing the operating wire.

The endoscope may be a flexible endoscope.

The suturing device detachably or monolithically attached at the distal end of the endoscope is provided with a curved needle detachably or monolithically attached to the driving member. The curved needle is provided with a hole through which a thread may pass, and the thread is inserted through the hole and through one of the channels of the endoscope from the operator side to the distal end.

With the curved needle housed in the protective member, the endoscope having the suturing device at its distal end is inserted through body cavities to the suturing site. The curved needle is moved to a specified position by manipulating the operation unit attached on the operator side of the endoscope for operating the curved needle, and the suturing device is pressed against the suturing site with the angulation mechanism of the endoscope. At this stage, the suturing device is fixed against the tissue with the aid of the needle-shaped tissue fixing member attached on the suturing device. In this state, the operation unit of the curved needle is operated to start a puncture.

After the tissue is punctured, once the end of the needle and the thread are seen over the tissue surface within the field view of the endoscope, an end of the thread is held with a thread grasping member and then led to operator side. With the end of the thread held at the operator side of the endoscope, another puncture is similarly made at slightly different suturing site, and the other end of the thread is held with the grasping member and led to the operator side. Both ends of the thread are tied to make a knot, which is pushed to the suturing site by the knot pusher through a channel of the endoscope. The hereinbeforementioned movement is repeated for several times to ligate the thread to suture the tissues.

BRIEF DESCRIPTION OF THE DRAWINGS

FIG. 5 illustrates the distal end of the supporting member.

FIGS. 9–22 illustrate various aspects of the first embodiment of the present invention.

FIGS. 35 through 45 are diagrams illustrating the suturing method of the present invention.

FIG. 48 shows a third embodiment of the suturing device wherein the curved needle shown in FIGS. 3 and 4 is replaced by the different curved needle.

FIG. 49 is a figure viewed from the arrow A in FIG. 48.

FIG. 50 is a cross sectional view taken from the line BB of FIG. 49.

FIGS. 108 through 121 illustrate a twenty-first embodiment of the present invention.

FIGS. 113 through 121 and 128 through 140 and 142 illustrate a twenty-second embodiment of the present invention.

FIGS. 126 through 127 and 141 illustrate parts of a first embodiment of the present invention.

DETAILED DESCRIPTION

Embodiment 1

A first embodiment of the present invention is shown in FIGS. 1 through 45, 126 through 127 and 141.

Figure 1:
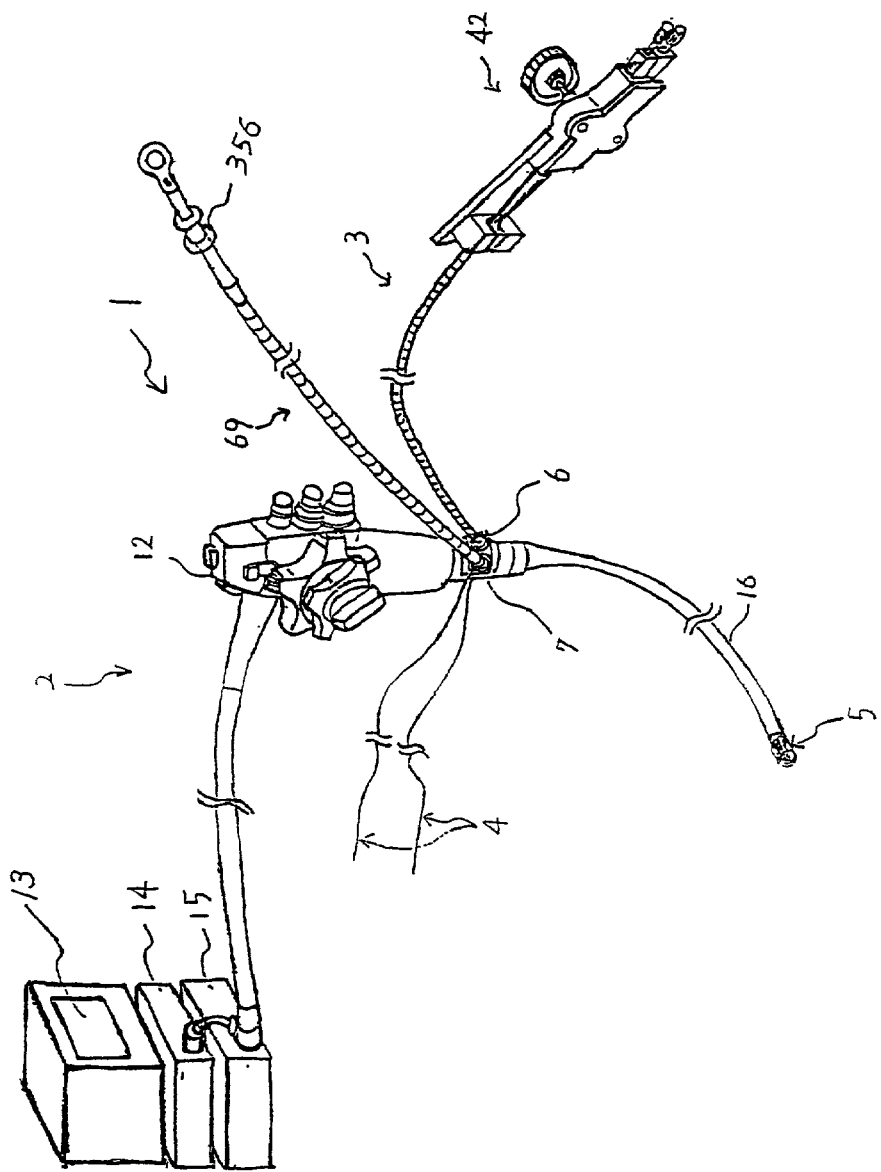
FIG. 1 shows an overall view of the endoscope suturing system of the present invention.
Figure 2:
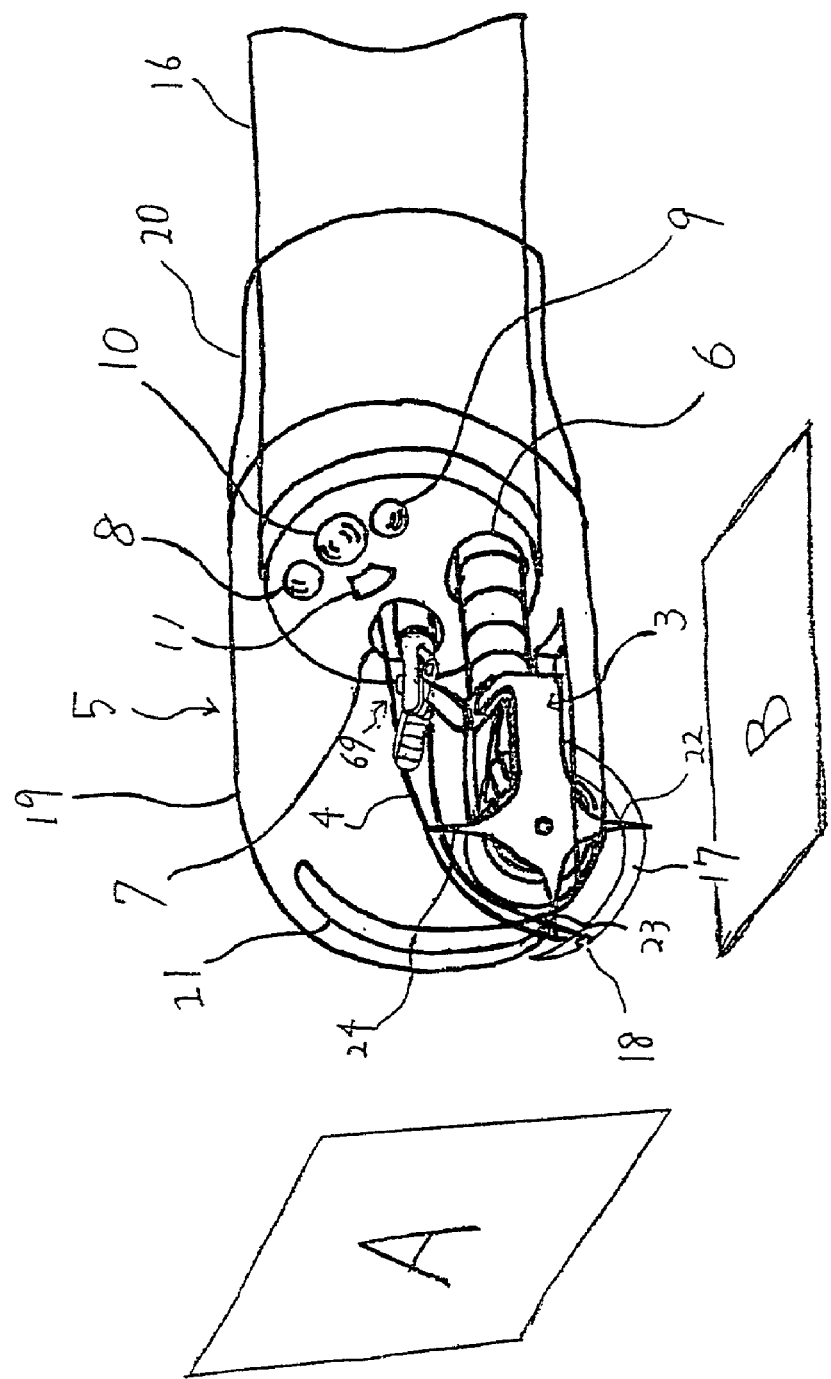
FIG. 2 is an enlarged view showing the distal end of the endoscope.
Figure 122:
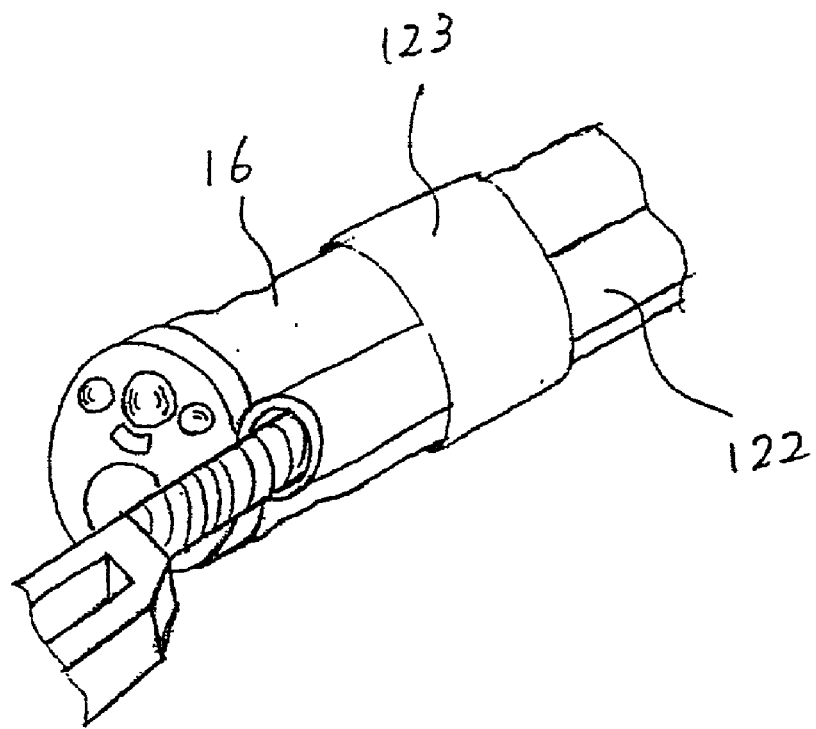
FIG. 122 shows an outer channel fixed with medical tape.

FIG. 1 shows an overall view of the endoscope suturing system 1. FIG. 2 is an enlarged view showing the distal end of the endoscope 11. As shown in FIG. 1, the suturing system 1 comprises an endoscope system 2, suturing device 3, thread 4, and tissue protective member 5. The endoscope system 2 comprises an endoscope 12, image processing unit 14, light source 15, and observation monitor 13. Although the endoscope 12 is equipped with two instrument channel ports 6 and 7, it may have only a single instrument channel port. Alternatively, an outer channel 122 may be fixed to a flexible portion 16 with a medical tape 123 or the like as shown in FIG. 122.

As shown in FIG. 2, the distal end of the endoscope is provided with a CCD camera 10, light guides 8 and 9, instrument channel ports 6 and 7, and a nozzle 11 for washing the lens of the CCD camera. Although a videoscope using a CCD is used in this embodiment, a fiberscope having an eyepiece lens may be used. The suturing device 3 is disposed in the instrument channel port 6. The thread 4 is hooked in a U shape in a needle's slit formed on the curved needle 17 of the suturing device 3, and extends from the operator side of the instrument channel port 7 therethrough. The external diameter of the curved needle 17 may be of any dimension in the order of millimeters as long as it may be inserted into body cavities, but is desirably from 5 mm or more to 30 mm or less for smooth insertion into body cavities and optimum puncture capability of the curved needle. The external diameter of the thread is desirably from 0.1 mm or more to 4 mm or less for the sufficient puncture capability into the tissue and the tensile strength. These external diameters of the curved needle and thread are applicable to all the hereinafter mentioned embodiments.

The tissue protective member 5 comprises a protective portion 19, which is at least partially transparent, and a fixing portion 20 made of elastomer resin such as silicone rubber and the protective portion 19 and the fixing portion 20 are fixed by press fitting or adhesion. The tissue protective member 5, of such a construction, is detachably fixed by the fixing portion 20 pressed in the distal end of the flexible portion 16. On the protective portion 19, protective member's slit 21 having a width to allow the curved needle 17 of the suturing device 3, and fixing needles 22 through 24 formed on the tissue fixing member 25, to pass through is continuously formed from the spherical part of the protective portion 19 to the cylindrical part. Since the protective member 5 is fixed to the distal end of the flexible portion 16, the suturing device 3 does not harm internal organs when the flexible portion 16 is inserted into body cavities. The length of the fixing needles may be longer or shorter than the external diameter of the curved needle, but longer fixing needles will enhance the force to fix the suturing device to the tissue.

Figure 3:
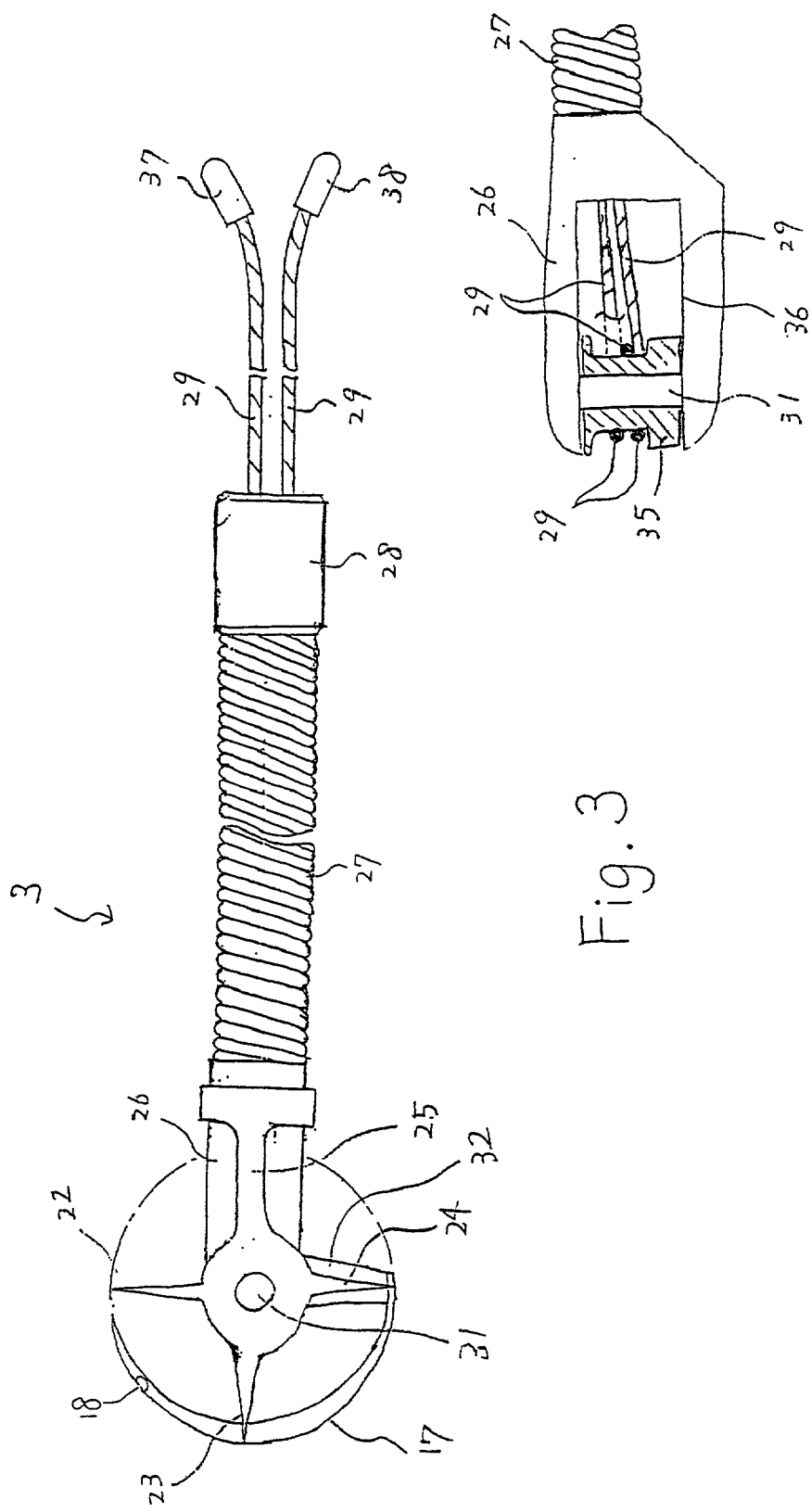
FIGS. 3 and 4 are views showing how the curved need is supported in the first embodiment.
Figure 4:
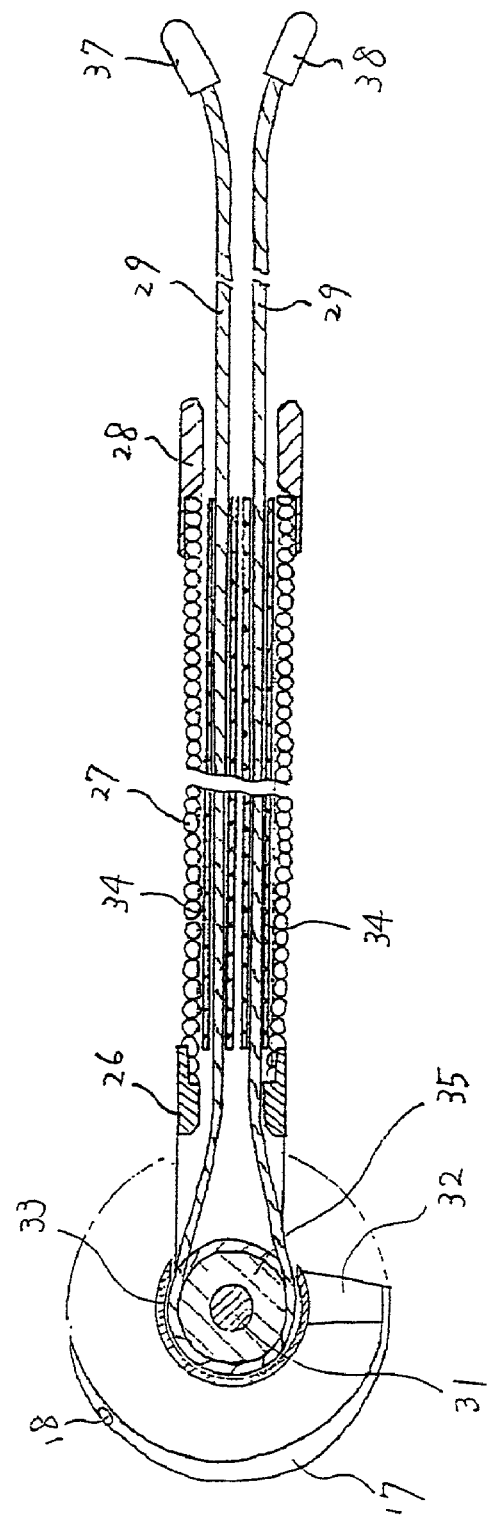
Figure 125:
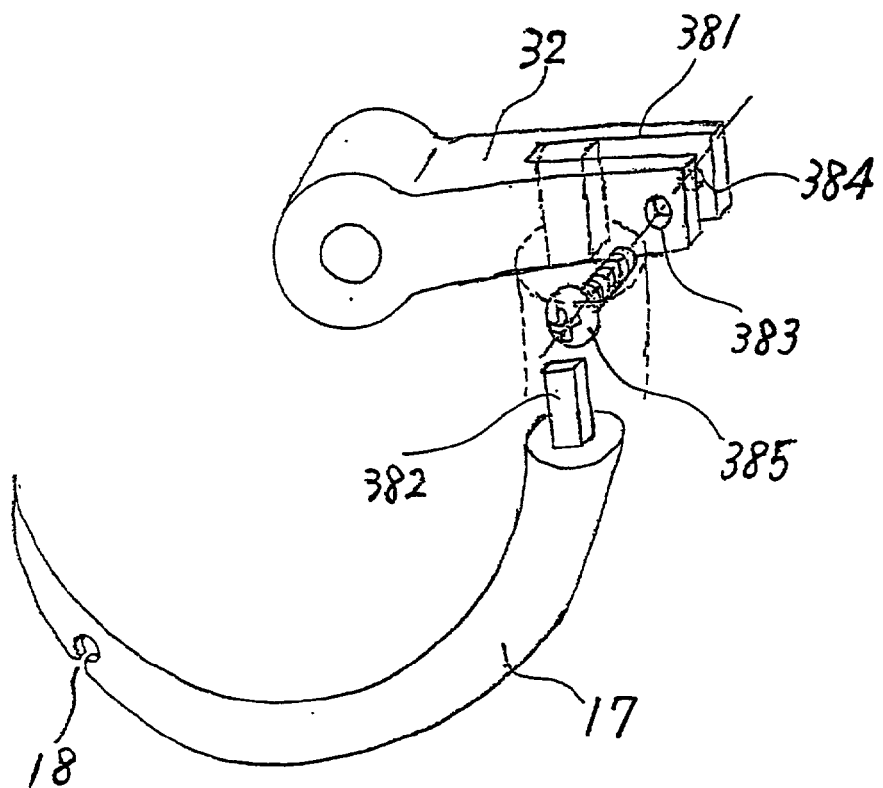
FIG. 125 shows a detachable need arrangement.

As shown in FIGS. 3 and 4, in the suturing device 3, a supporting member 26 is fixed to the distal end of a flexible coil 27 having internal cavity, a sleeve member 28 having internal cavity is disposed at the proximal end, and operating wires 29 pass through the flexible coil 27 and sleeve member 28. As shown in FIG. 5, a clevis 36 is provided at the distal end of the supporting member 26, and a disk 35 for rotating the curved needle between the clevis is provided to rotate on an axis 6, both ends of which are fixed by the supporting member 26. The curved needle 17 is fixed to the disk 35 via an arm 32. The arm 32 and the curved needle 17 may be constructed to be detachable as shown in FIG. 125.

Figure 126:
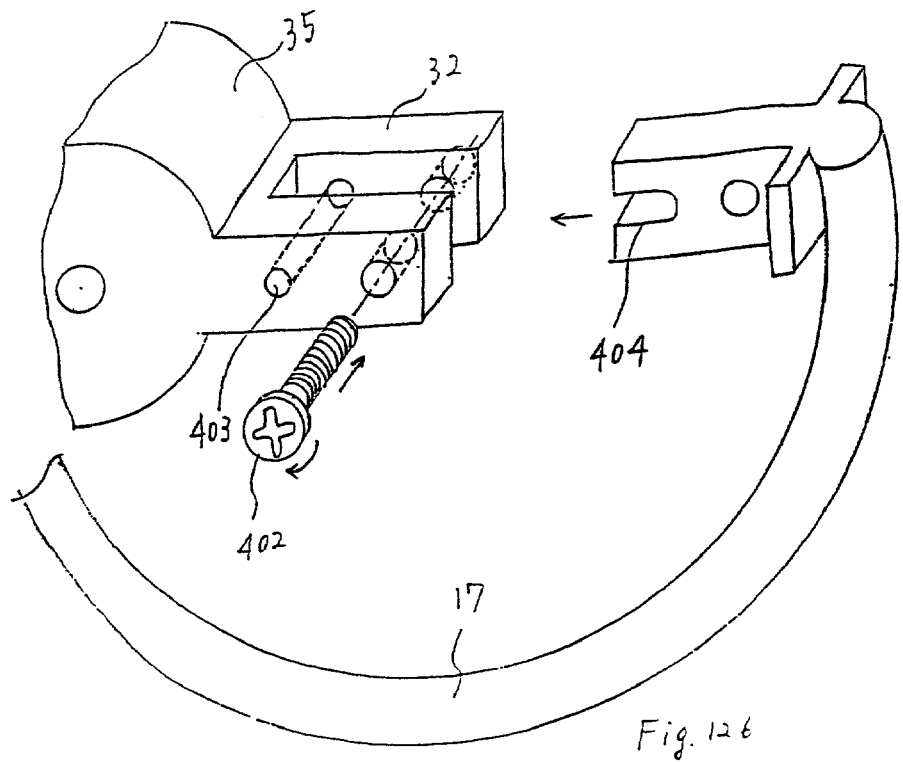
Figure 127:
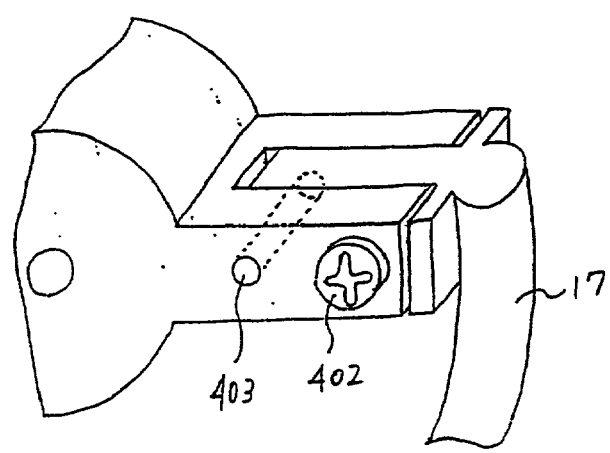

The detachable construction detachably fixes the arm 32 and the curved needle 17 by fitting an engagement member 382 formed on the operator side of the curved needle in a slit 381 formed on the arm 32 and by tightening a screw 385 into a through-hole 383 and a hole 384 provided at the distal end of the arm 32. As shown in FIGS. 126 and 127, they may be detachable by means of a structure in which the pin 403 fixed on arm 32 fits in the slit 404 of the curved needle 17. Such a detachable construction of the curved needle and the arm may be applied to the hereinafter-mentioned Embodiments 2 through 23.

The operating wires 29 run around the circumference of the disk 35 at least for a turn, and a portion of the wound operating wires 29 are fixed to the circumference of the disk 35 by brazing, soldering or friction force so as to transmit the force of the operating wires 29 to the disk 35 reliably. As shown in FIG. 4, a disk cover 33 is fixed to the supporting member 26 by a screw or other means to prevent the operating wires 29 wound around the disk 35 from dislocating therefrom. The curved needle 17 has a curved shape so that the rotation center of the curved needle 17 is substantially identical to its center of curvature.

The operator-side ends of the operating wires 29 are respectively fixed by the stoppers 37 and 38.

Figure 9:
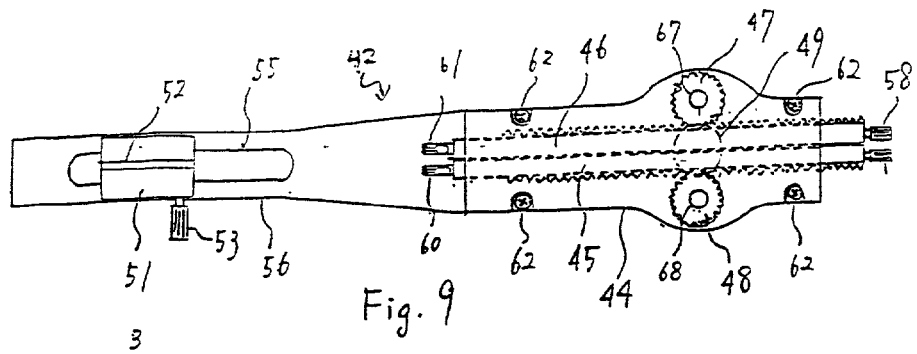
Figure 10:
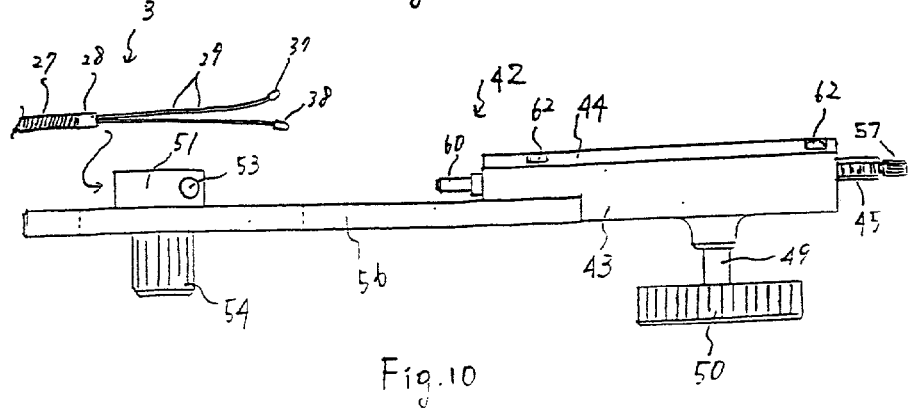
Figure 11:
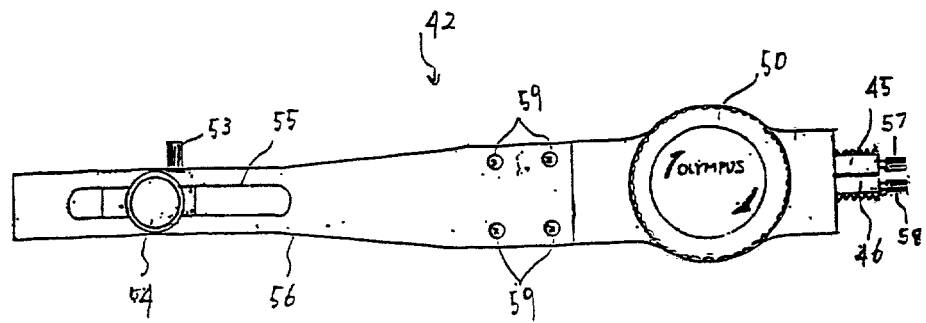
Figure 12:
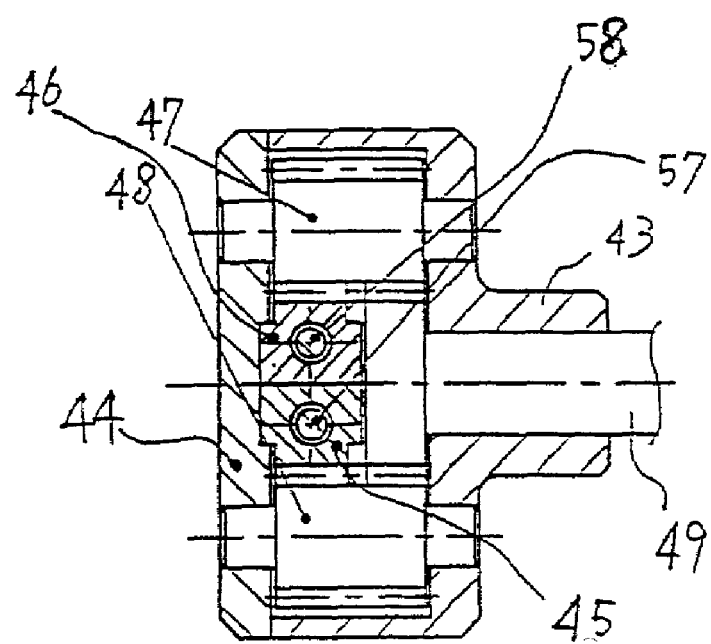

As shown in FIGS. 1 and 9 through 12, the operation unit 42 comprises a housing 43, a plate 56 fixed to the housing 43 with four screws 59, a slider 51 which is slidable in a slot 55 formed on the plate 56 using a setscrew 54 and may be fixed at any given position, two racks 45 and 46 slidably disposed in the housing 43, pinion gears 48 and 47 respectively being in engagement with the racks 45 and 46, a shaft 49 having gears engaged with both the pinion gears 47 and 48, a cover 44 having holes 67 and 68 formed thereon to be engaged with the shafts of the pinion gears 47 and 48 and being fixed with a screw 62, a handle 50 fixed at the end of the shaft 49, and stopper fixing members 60 and 61 respectively fixed with screw 30 to the racks 45 and 46 as shown in FIG. 9 and 17.

Figure 13:
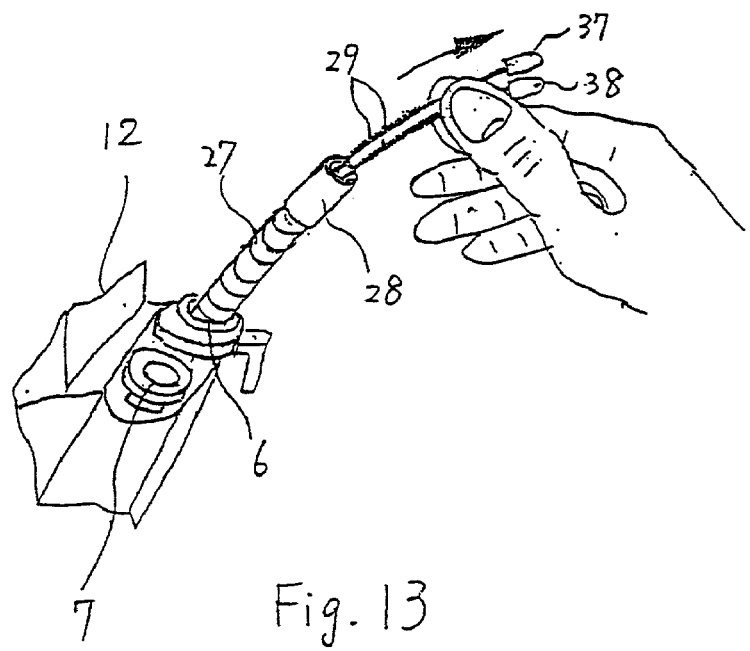
Figure 14:
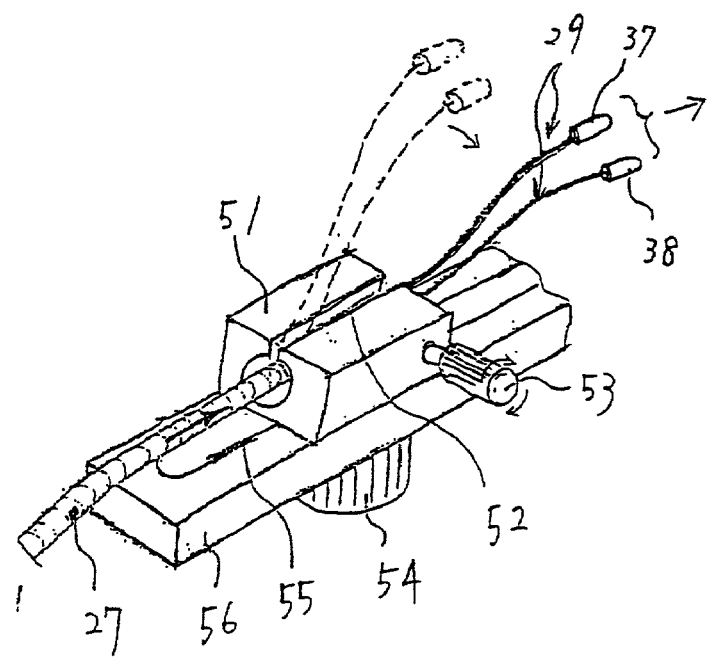
Figure 16:
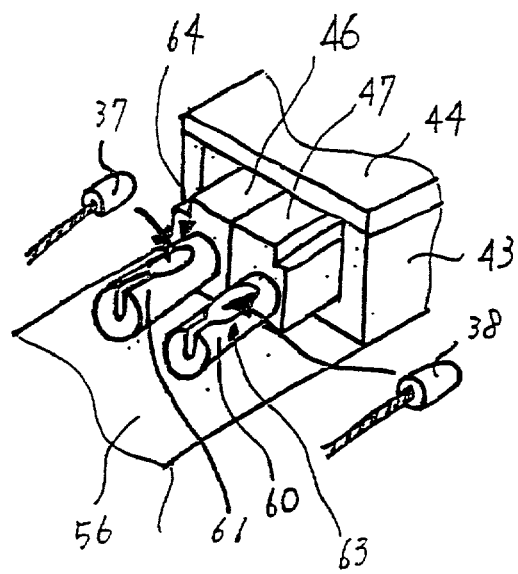

As shown in FIG. 13, the stoppers 37 and 38 coming from the instrument channel port 6 allow the operating wires 29 through a slit 52 of the slider 51 as shown in FIG. 14, and detachably fix the sleeve member 28 with a setscrew 53. Then the stoppers 37 and 38 are inserted into ports 63 and 64 formed on the stopper fixing members 60 and 61 as shown in FIG. 16, hooked on abutment surfaces 65 and 66 formed on the stopper fixing members 60 and 61 as shown in FIG. 17, and held by setscrews 57 and 58 to prevent them from withdrawing from the ports 63 and 64.

Figure 22:
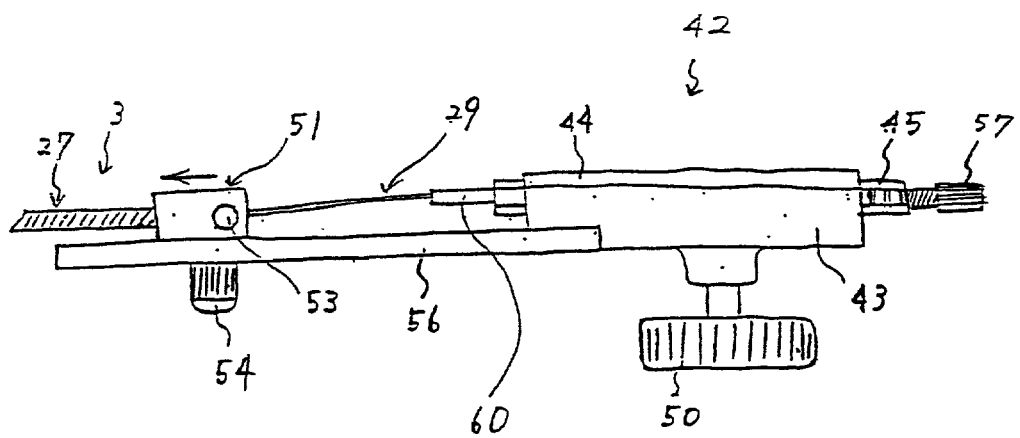

As shown in FIG. 22, the suturing device fixed with the setscrew to the slider 51 is slid in the direction shown with the arrow, and the slider 51 is fixed on the plate 56 with the setscrew 43 with tension applied to the operating wires 29. In the thus constructed operation unit 42, rotational movement of the handle 50 is converted to linear movement of the racks 45 and 46 via the shaft 49 and the pinion gears 47 and 48 as shown in FIGS. 18 through 21 to push or pull the operating wires 29 or rotate the curved needle 17.

Figure 6:
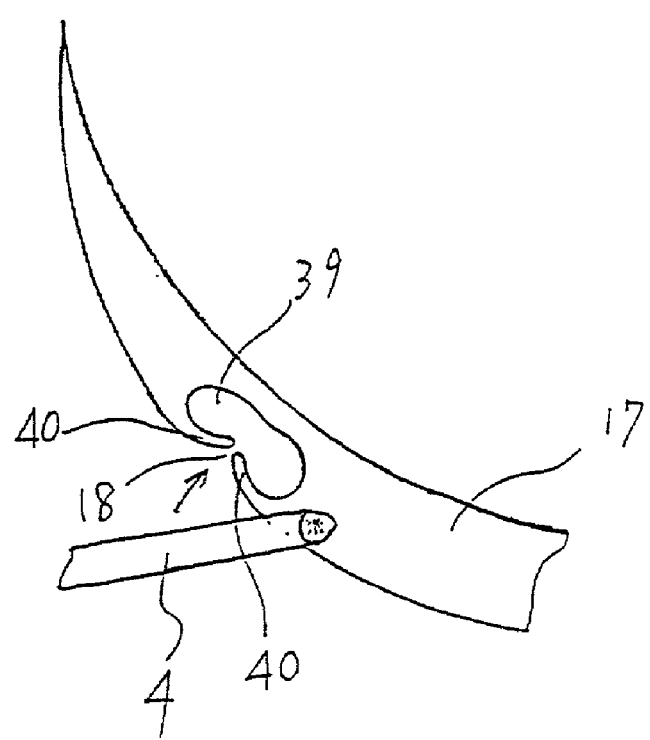
FIGS. 6–8 show a details of a needle and threading thereof.
Figure 7:
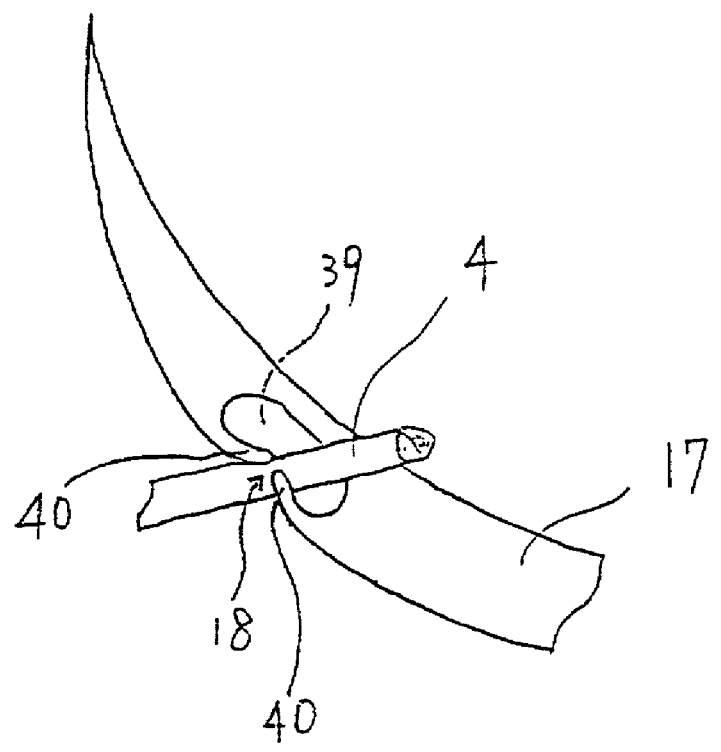

At this stage, the directions of the movement of the racks 45 and 46 are opposite as shown in FIGS. 19 and 21. It is obvious that the curved needle may be rotated in the normal or reverse direction according to the rotational direction of the handle 50. As hereinbefore mentioned, a needle's slit 18 is formed at the pointed end of the curved needle 17 for passage of the thread 4, and the thread passes therethrough as shown in FIG. 2. As shown in FIGS. 6 and 7, the needle's slit 18 comprises two flaps 40 with a width slightly smaller than the external diameter, and the thread or the flaps 40 are elastically deformed by pressing the thread 4 into the needle's slit to let the thread 4 be housed in the engagement member 39.

Figure 8:
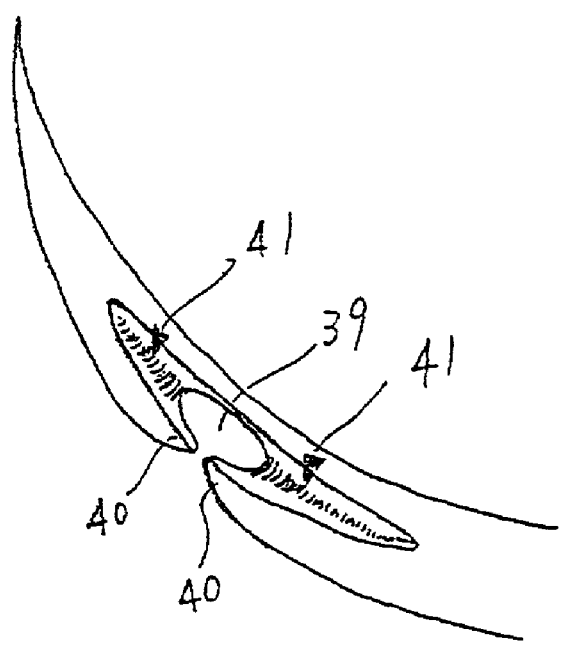

Therefore, the thread does not come out of the engagement member 39 unless a certain amount of force is applied. Since two flaps 40 enter inside the periphery of the curved needle 17, the curved needle 17 smoothly punctures the tissue without any hindrance by the flaps 40. As shown in FIG. 8, a groove 41 may be formed to allow the thread 4 to enter the curved needle 17 so as to lessen the puncture force. As long as the thread 4 is not withdrawn from the engagement member 39 during suturing even when the thread 4 is made not to be withdrawn from the engagement member 39 as in the first embodiment, the width of the needle's slit 18 may be larger than the external diameter of the thread 4.

The operator side of the thread 4 comes out of the body cavity via the instrument channel port 7 as shown in FIG. 1. A thread grasping/withdrawing means 69 is inserted in the instrument channel port 7 as shown in FIGS. 1 and 2 so that an end of the thread 4 may be grasped and led out to the outside of the body cavity after the curved needle 17 punctures the tissue. Although grasping forceps are used in this embodiment, any device may be used as long as it can perform the grasping and withdrawing procedure. The construction may be as shown in FIGS. 23 through 30 and FIG. 141.

Figure 23:
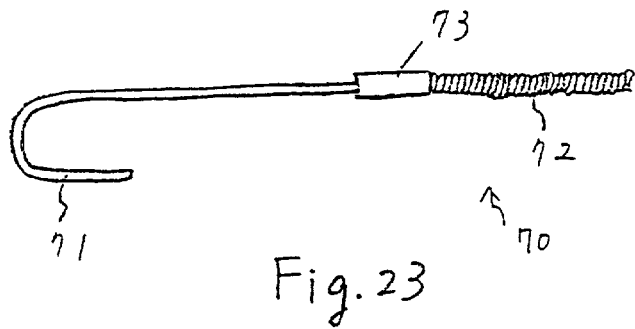
FIGS. 23 through 30 and FIG. 141 illustrate various thread grasping/withdrawing means which can be used in embodiments of the present invention.

A thread grasping/withdrawing means 70 shown in FIG. 23 comprises an elongate member 71 with U-shaped distal end and an elongate flexible tubular member 72, and the operator side of the elongate member 71 and the elongate flexible tubular member 72 are fixed by brazing or soldering via a tubular member 73.

Figure 32:
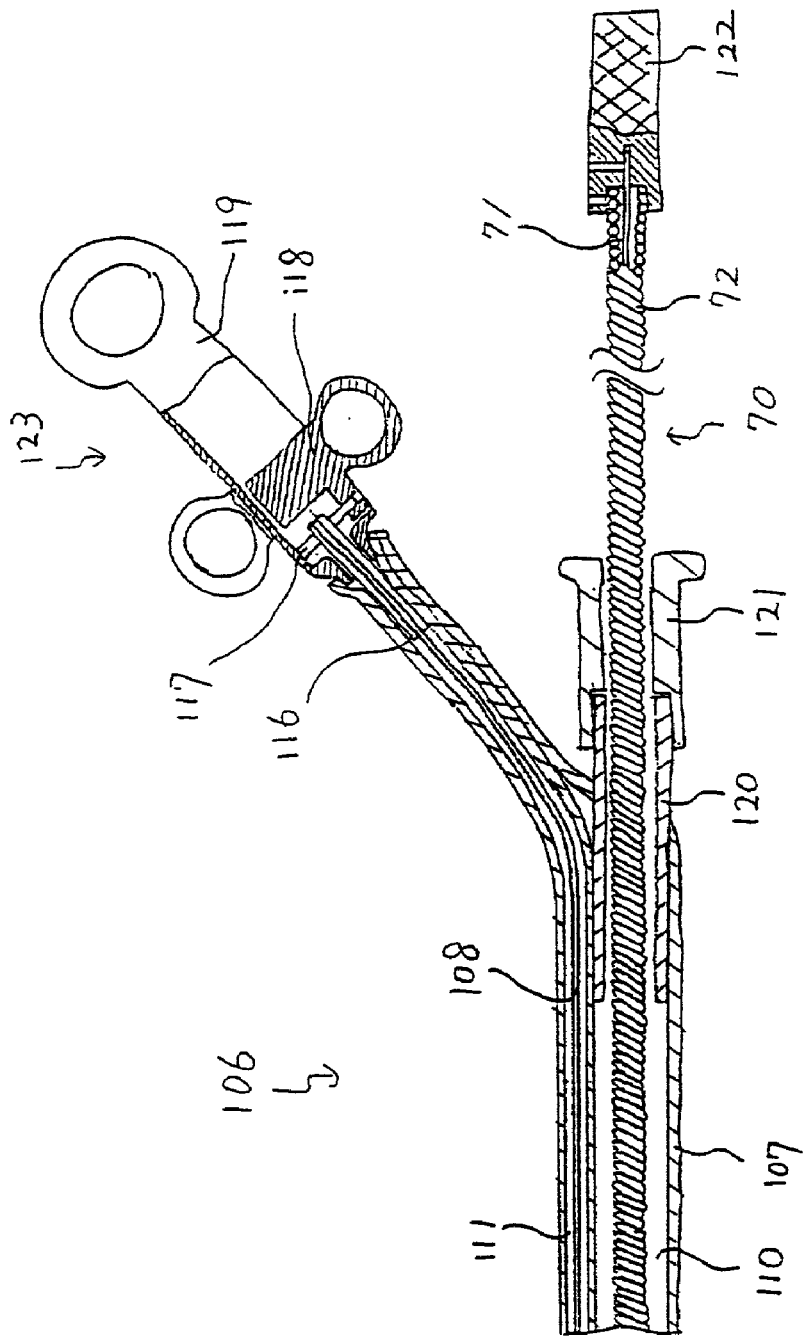

The elongate member 71 extends to the operator side of the elongate flexible tubular member 72 and is monolithically fixed to an operation unit 122 as shown in FIG. 32 by brazing or soldering so that any force on the elongate flexible tubular member 72 does not stretch the elongate member 71. Such a construction allows an end of the punctured thread 4 to be hooked by the thread grasping/withdrawing means 70 inserted via the instrument channel port 7 and withdrawn to the operator side of the instrument channel port 7. When the thread grasping/withdrawing means 70 is inserted via the instrument channel port 7, a tube, not shown in the figure, for covering at least the distal end of the elongate member 71 may be added to prevent the U-shaped part of the elongate member 71 from interfering with the inside of the instrument channel port 7.

Figure 24:
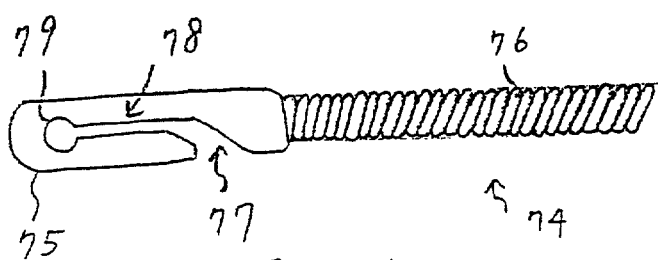

A thread grasping/withdrawing means 74 shown in FIG. 24 comprises a hook 75 further comprising a port 77 having a width for accepting the thread 4, a slit 78 slightly smaller than the external diameter of the thread 4, and a slit 79 larger than the external diameter of the thread 4, and an elongate flexible tubular member 76. The operator side of the elongate member 71 and the elongate flexible tubular member 72 are fixed by brazing or soldering. A stylet, which does not stretch under force to the elongate flexible tubular member 76 as in the thread grasping/withdrawing means 70 and not shown in the figure, is provided in the elongate flexible tubular member 76 and fixed at the distal end and the operator side of the elongate flexible tubular member 76, and an operation unit, similar to the thread grasping/withdrawing means 70 and not shown in the figure, is provided. Such a construction allows an end of the punctured thread 4 to be introduced from the port 77 by the thread grasping/withdrawing means 74, inserted in the instrument channel port 7, pushed to deform itself or the slit 78 and to enter the slit 79. It is hooked by the slit 79 to be withdrawn to the operator side. Since the slit 78 has a width smaller than the external diameter of the thread 4, the thread 4 does not come off from the hook 75.

Figure 25:
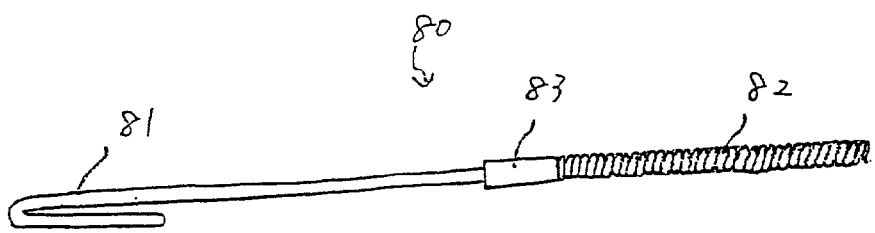

A thread grasping/withdrawing means 80 shown in FIG. 25 comprises an elongate member 81 with its distal end bent and made to have a width smaller than the external diameter of the thread 4 and an elongate flexible tubular member 82. The operator side of the elongate member 81 and the elongate flexible tubular member 82 are fixed by brazing or soldering via a tubular member 83. The elongate member 81 extends to the operator side of the elongate flexible tubular member 82 as in the thread grasping/withdrawing means 70 and is monolithically fixed to an operation unit not shown in the figure by brazing or soldering as the thread grasping/withdrawing means 70 so that any force on the elongate flexible tubular member 82 does not stretch the elongate member 81. Such a construction allows an end of the punctured thread 4 to be hooked by the thread grasping/withdrawing means 80 inserted via the instrument channel port 7 and withdrawn to the operator side of the instrument channel port 7. When the thread grasping/withdrawing means 80 is inserted via the instrument channel port 7, a tube, not shown in the figure, for covering at least the distal end of the elongate member 81 may be added to prevent the distal end of the elongate member 81 from interfering with the endoscope 12.

Figure 26:
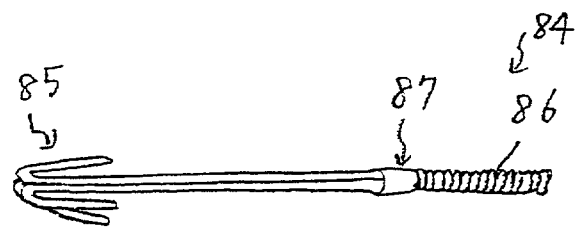

A thread grasping/withdrawing means 84 shown in FIG. 26 comprises a plurality of elongate members 81 of the thread grasping /withdrawing means 80 and may catch the thread 4 in multiple directions. When the thread grasping/withdrawing means 80 is inserted via the instrument channel port 7, a tube, not shown in the figure, for covering at least the distal end of the elongate member 81 may be added to prevent the distal end of the elongate member 81 from interfering with the endoscope 12.

Figure 27:
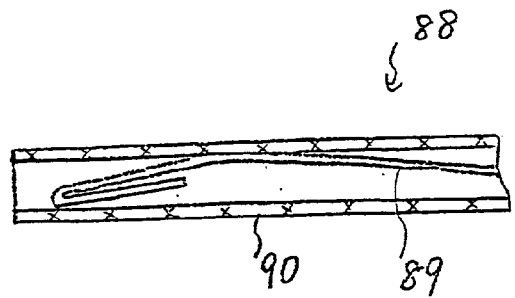
Figure 28:
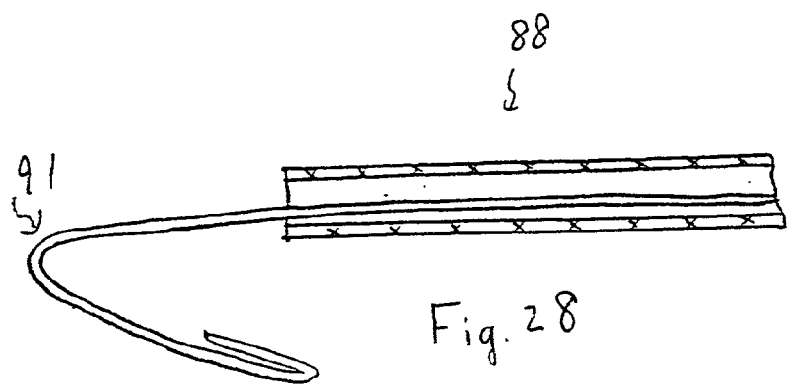

A thread grasping/withdrawing means 88 shown in FIGS. 27 and 28 has its distal end bent to have a width smaller than the external diameter of the thread 4, and comprises a folded portion 91, an elongate member 89 made of super-elastic material or the like, and an elongate flexible tubular member 90, and the elongate member 89 is movably disposed in the elongate flexible tubular member 90.

The thread grasping/withdrawing means 88 may be operated by an operation unit not shown in the figure between a position where the elongate member 89 is housed in the elongate flexible tubular member 90 as shown in FIG. 27 and another position where the distal end of the elongate member 89 faces the operator side as shown in FIG. 28. Such a construction allows an end of the punctured thread 4 to be approached from the distal end side to the operator side and hooked by the thread grasping/withdrawing means 88.

Figure 29:
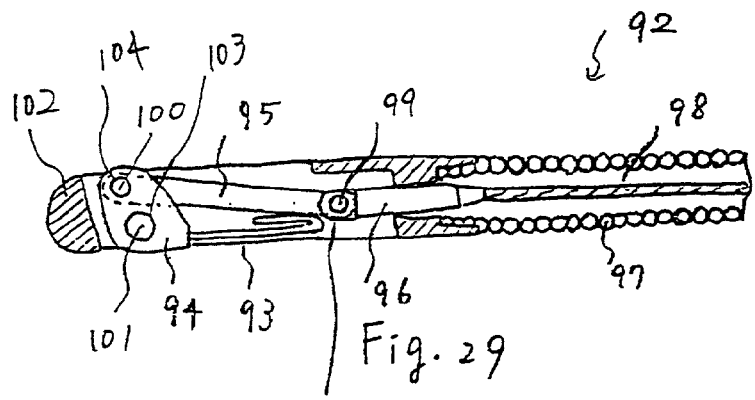
Figure 30:
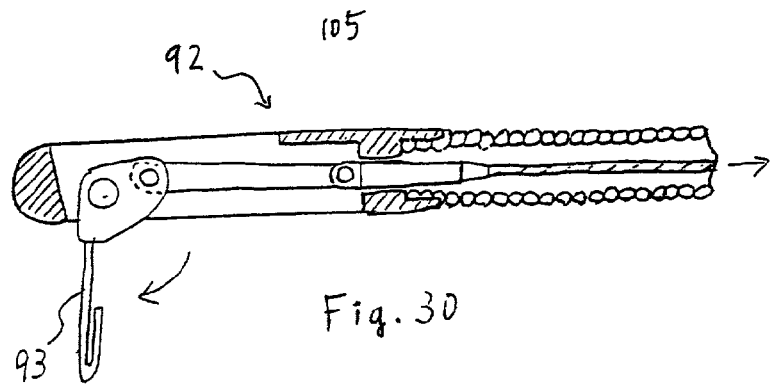

A thread grasping/withdrawing means 92 shown in FIGS. 29 and 30 comprises an elongate member 93 with its distal end folded to have a width smaller than the external diameter of the thread 4, a cam 94 fixed to the operator side of the elongate member 93, a pin 101 fitted in a hole 103 formed on the cam 94, a supporting member 102 for supporting the both ends of the pin 101, a link 95 rotatably engaged via the pin 100 with a hole formed at distance from the hole 103 on the cam 94, a rod 96 rotatably engaged with the link 95 via the pin 99, an operating wire 98 fixed to the rod 96 by brazing or soldering and connected to an operation unit provided on the operator side and not shown in the figure, and an elongate flexible tubular member 97 having an internal cavity in which the operating wire moves back and forth and is fixed to the operator side of the supporting member 102.

Such a construction enables an end of the thread 4 after tissue puncture to be approached from side against the axis of the thread grasping/withdrawing means 92, hooked by the elongate member 93, and withdrawn to the operator side. When the thread grasping/withdrawing means 92 is inserted via the instrument channel port 7, the elongate member 93 is housed in the supporting member 102 to prevent the distal end of the elongate member 93 from interfering with the inside of the instrument channel port 7. Although a single elongate member 93 is used in this embodiment, a plurality of the elongate members 93 may be fixed to the cam 94. In addition, the hook 75 shown in FIG. 24 may be fixed.

Multiple-thread coil may be used for 72, 76, 82, 86, and elongate flexible tubular member 97 to improve rotation.

Figure 31:
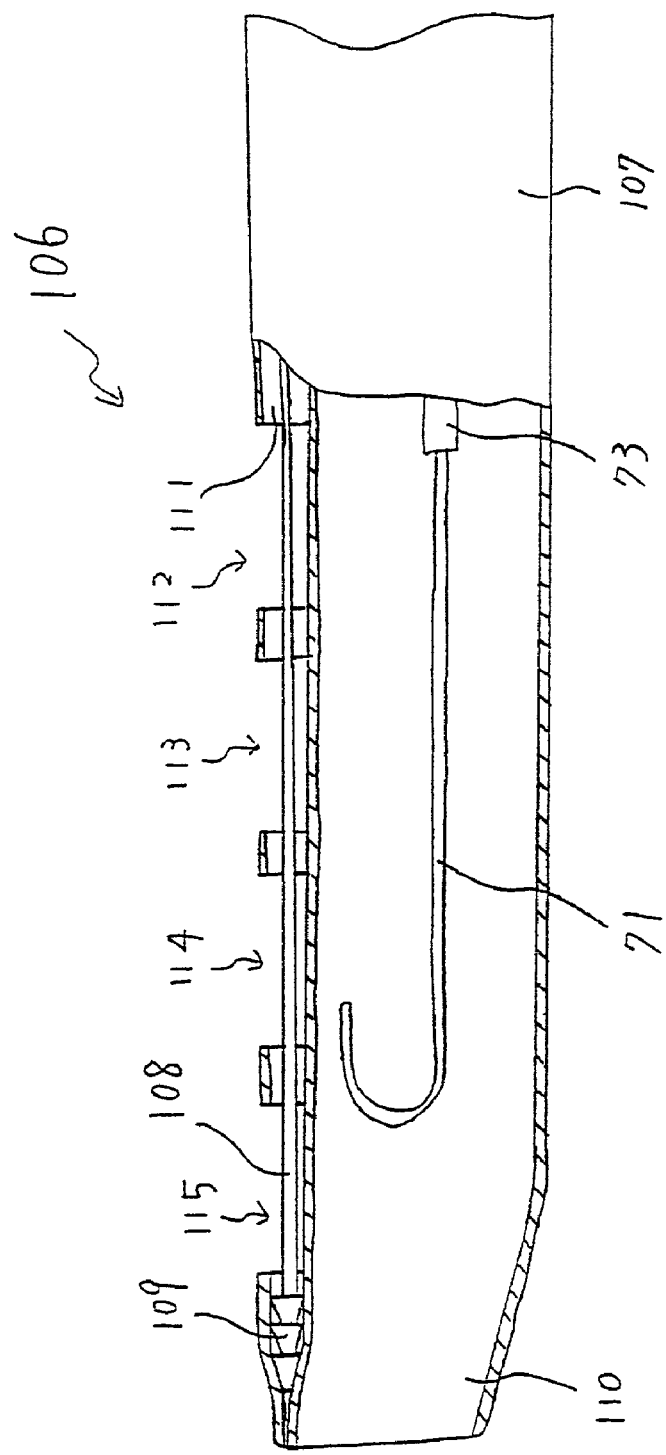
FIGS. 31 and 32 illustrate a manipulator.

The distal end of the thread grasping/withdrawing means 70, 74, 80, 84, 88, and 92 may be deflected by using a manipulator 106 shown in FIGS. 31 and 32. The manipulator 106 comprises a multi-lumen tube 107 having a lumen 110 to accept a thread grasping/withdrawing means and a lumen 111 for movably disposing an operating wire 108 for deflecting the distal end, and an operation unit 123 provided on the operator side for moving the operating wire 108 back and forth. The distal end of the operating wire 108 is fixed by brazing or soldering to a stopper 109 fixed on the distal end of the lumen 111 by press fitting or adhesion. Slits 112 through 115 are formed in the vicinity of the distal end of the lumen 111 to facilitate deflection of the multi-lumen tube 107. The operator side of the lumen 111 is fixed to a pipe 116 by brazing, soldering or calking, and the operator side of the pipe 116 is fixed to a fixing pin 117 by similar method as hereinbefore mentioned. The fixing pin 117 is fitted in a hole formed on a handle 118 and securely fixed.

Figure 33:
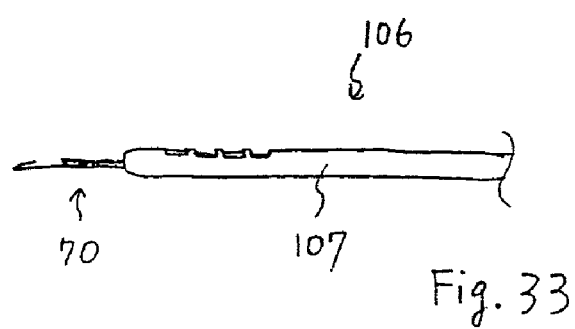
FIGS. 33 and 34 illustrate the distal end of the manipulator.
Figure 34:
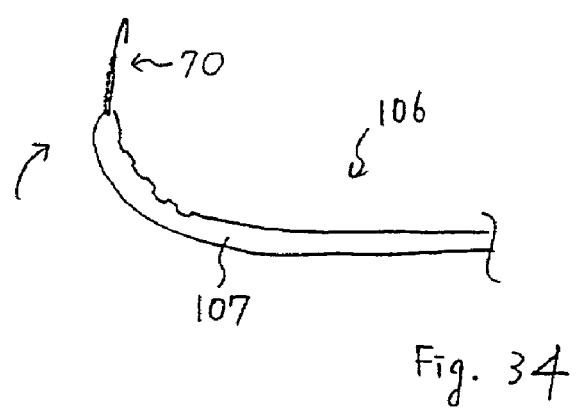

The handle 118 is slidable over the axis formed on a housing 119, and moving the handle 118 back and forth will deflect the distal end of the manipulator 106 as shown in FIGS. 33 and 34. A port 121 is fixed on the operator side of the lumen 110 via a cylindrical connecting member 120 so that the thread grasping/withdrawing means 70, 74, 80, 84, 88, or 92 may be inserted or disposed.

Figure 141:
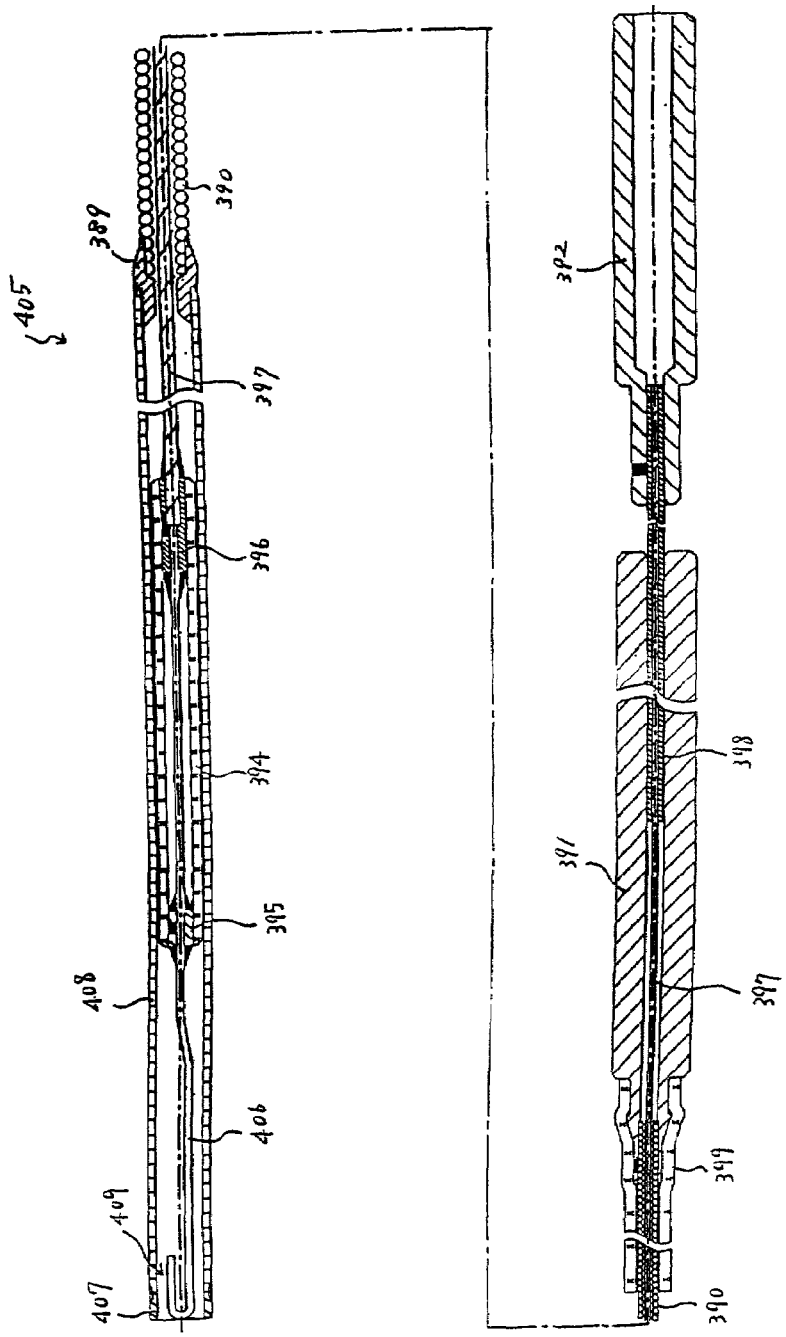

A thread grasping/withdrawing means 405 shown in FIG. 141 comprises a tube tip 407, a coil sheath 408 fixed to the near end of 407, a connecting member 389 which connects 408 and a multicoil 390, a handle 391 fixed to the near end of 390, thin member 406 with a U-shape hook 409 on tip end in which a thread can swing, a connecting member 396 which connects 406 and torque wire 387, a pipe 398 fixed to the near end of 397, and a handle 392 fixed to 398. Such structure of 405 enables one to grasp a thread freely by rotating 392 that sequentially rotates 406 and moving 392 back and forth sequentially pushes 406 out of 407. Moreover, 406 has a centering member 394 fixed to the guide member 394 and the connecting member 396 to keep 406 on the center of axis.

A procedure to build the suturing device 3 into the endoscope system is described below by referring to FIGS. 1 through 3.

As shown in FIG. 2, insert the suturing device from the instrument channel port 6 at the distal end of the flexible portion 16 and pull out the arm 32 from the operator side of the instrument channel port 6 as shown in FIG. 35. At this stage, a transparent tube 124 as shown in FIG. 36 may be inserted into the instrument channel port 6 to facilitate insertion of the stoppers 37 and 38 so that the operating wires 29 and stoppers 37 and 38 are not stuck at branch in the instrument channel port 6.

When the stoppers 37 and 38 come out of the instrument channel port 6, remove the transparent tube 124 as shown in FIG. 37.

Attach the operation unit 42, which is to be mounted on the operator side of the suturing device 3, on the suturing device 3 in the hereinbefore-mentioned method.

Use grasping forceps such as the thread grasping/withdrawing means 69 the thread 4 introduced in the instrument channel port 7 on the needle's slit 18 shown in FIG. 2. Although the thread 4 is inserted in the instrument channel port 7, it may be set along the outside of the flexible portion 16.

Mount the tissue protective member 5 at the distal end of the flexible portion 16 as shown in FIG. 2.

Insert the thread grasping/withdrawing means 69 from the operator side of the instrument channel port 7 as shown in FIG. 1, and lead an end of the thread 4 out of it for grasp as shown in FIG. 2.

The suturing procedure is described below by referring to FIGS. 1, 2, 19, and 38 through 44.

Insert the distal end of the flexible portion 16 set as shown in FIG. 2 to the suturing target site in the body cavity.

Figure 38:
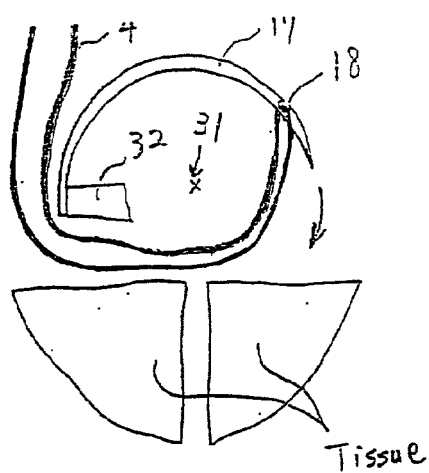

Rotate the handle 50 clockwise shown in FIG. 19 to move the curved needle 17 to the position shown in FIG. 38. Then press the tissue protective member shown in FIG. 2 against the tissue, press the suturing device 3 toward the distal end to puncture the tissue with the fixing needle 23, and securely fix the suturing device 3 to the suturing target site. The tissue will not be dislocated during puncture by the curved needle 17 by fixing the suturing device 3 to the suturing target site.

Figure 39:
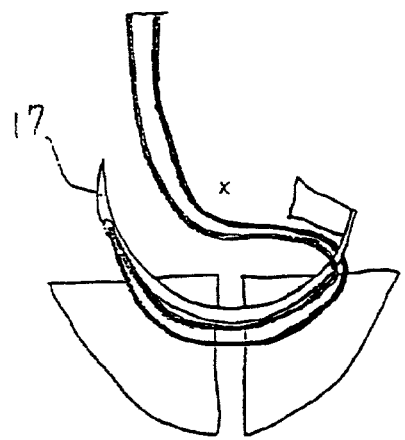
Figure 40:
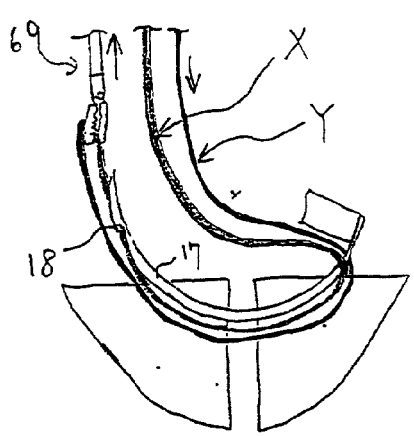

Rotate the handle 50 counterclockwise to urge the curved needle 17 to puncture the suturing target site as shown in FIG. 39. Grasp an end of the thread 4 coming out of the tissue with the thread grasping/withdrawing means 69 inserted via the instrument channel port 7 as shown in FIG. 40 to bring the end out of the body cavity.

Figure 41:
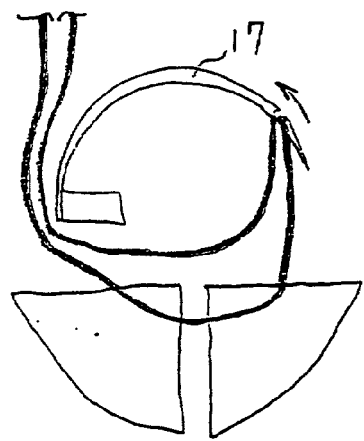

Rotate the handle 50 clockwise as shown in FIG. 41, and remove the curved needle 17 from the tissue.

Figure 42:
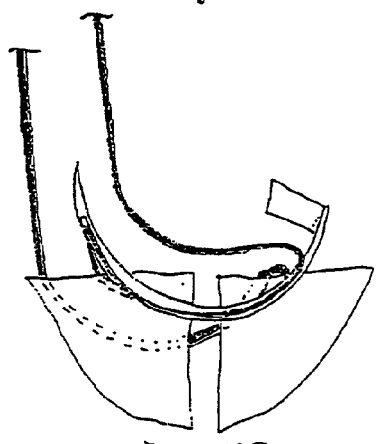
Figure 43:
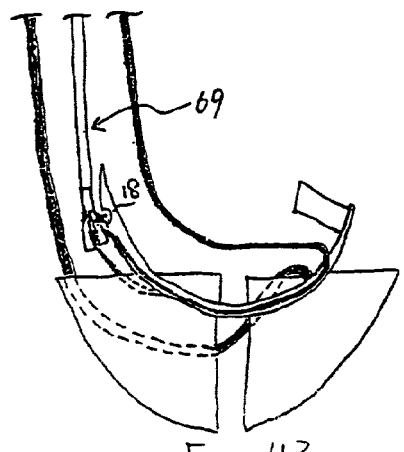
Figure 44:
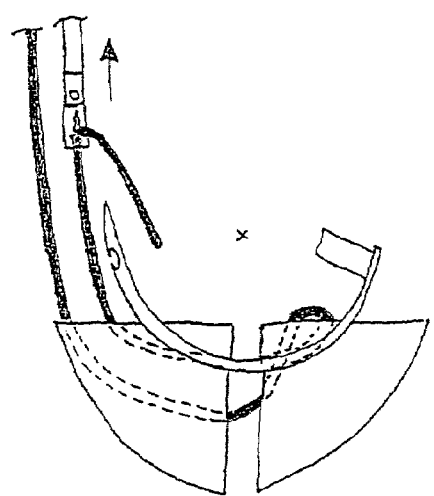

Adjust the angle of the endoscope to puncture the tissue slightly away from the previous puncture as shown in FIG. 42. Grasp the thread 4 with the thread grasping/withdrawing means 69 as shown in FIG. 43 to remove the thread 4 from the needle's slit 18, and lead the other end of the thread 4 as shown in FIG. 44 while retaining sutured thread in place.

Figure 45:
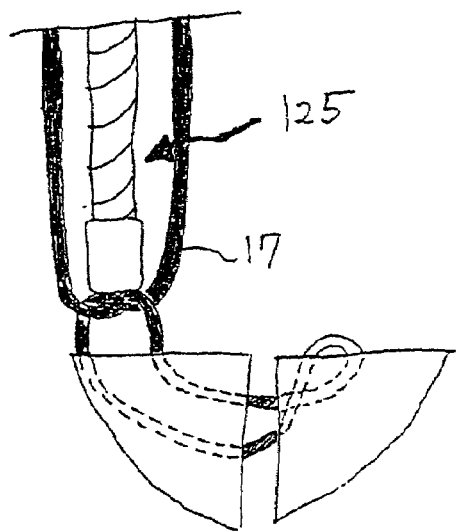

Use the two ends of the thread 4 out of the body cavity to make a knot as shown in FIG. 45, and push the knot by a knot pusher 125 inserted in the instrument channel port 7 to the suturing site. Repeat this step for several times to securely tighten the knot to complete the suturing procedure.

Although the area A shown in FIG. 2 is sutured in this embodiment, the area B may also be sutured in the same manner with this construction. When the thread grasping/withdrawing means 69 is set in the lumen 110 of the manipulator 106 shown in FIGS. 31 and 32 to freely deflect the distal end of the thread grasping/withdrawing means 69, the thread 4 may be further easily grasped. Although the manipulator 106 shown in FIGS. 31 and 32 only deflects in one direction, it should be readily understood that three mechanisms including the operating wire 108 may be placed on three locations at 90-degree intervals to enable four-direction deflection.

The advantage obtained with this procedure will now be explained. Since the puncture force is efficiently conveyed to the curved needle even in any bending state of the endoscope, the puncture force may be efficiently conveyed to the curved needle to attain a deep puncture into the tissue.

Since the curved needle 17 may be rotated both in the normal and reverse directions simply by rotating the handle 50, the puncture position may be repeatedly corrected.

Since the fixing needles 22 and 23 which may be urged into the tissue for fixing the tissue, and the protective portion 19 having a slit with a width to allow the passage of the curved needle 17, the puncture site may be securely fixed, and the curved needle 17 may attain deep puncture, thus attaining safe and reliable suturing.

Since the instrument channel port of the endoscope may be used, the suturing procedure may be employed even in a narrow body cavity.

Since a general-purpose endoscope may be used, cost may be reduced.

The independent structure of the suturing device enables washing, disinfection, and sterilization as in conventional instruments.

Embodiment 2

Figure 46:
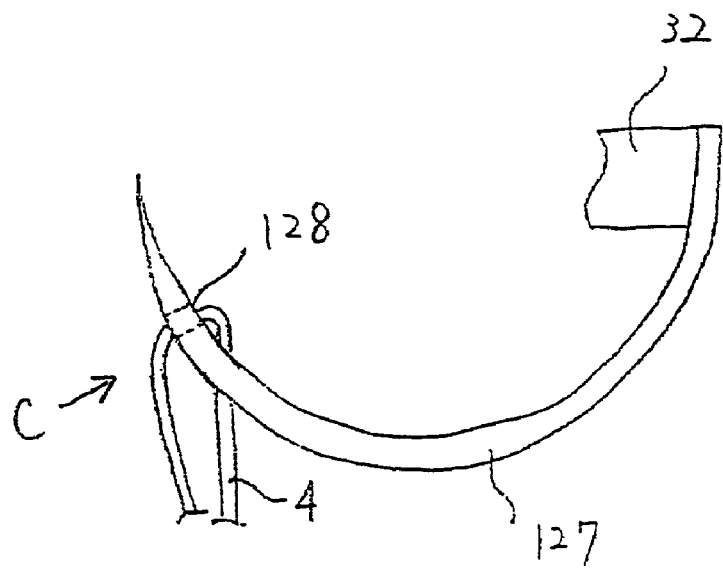
FIG. 46 shows a third embodiment of the suturing device wherein the curved needle shown in FIGS. 3 and 4 is replaced by a different curved needle.
Figure 47:
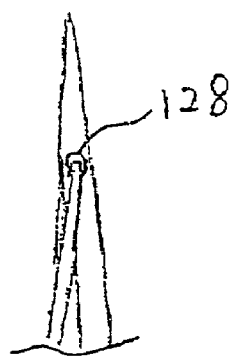
FIG. 47 is a figure viewed from the arrow C in FIG. 46.

A second embodiment of the present invention is shown in FIGS. 46 and 47.

The second embodiment has the same construction as the first embodiment, except that the curved needle 17 is replaced by the curved needle 127; therefore only the construction of the curved needle 127 is described.

FIG. 46 shows the suturing device 3 wherein the curved needle 17 shown in FIGS. 3 and 4 is replaced by the curved needle 127. FIG. 47 is a figure viewed from the arrow C in FIG. 46. As shown in FIGS. 46 and 47, a hole 128 in the rotation axial direction of the curved needle 127 is provided at the distal end of the curved needle 127.

The assembly method of the second embodiment is same as that of first except that the thread 4 is inserted through the hole 128, not hooked to the needle's slit 18. The suturing procedure is the same as that of the first embodiment except that the thread 4 is withdrawn from the hole 128, instead of being removed from the needle's slit 18.

In addition to the advantages of the first embodiment, since the hole 128 is located parallel to the rotational trajectory of the curved needle 127, the orientation of the hole 128 becomes almost the same as that of the axes of the thread grasping/withdrawing means 69 and the instrument channel port 7 after tissue puncture by the curved needle 127, thus facilitating removal of the thread 4 from the hole 128 in grasping and withdrawing of the thread 4 and decreasing the time for grasping and withdrawing the tread 4.

Embodiment 3

The third embodiment is shown in FIGS. 48 through 50. The third embodiment has the same construction as the first, except that the curved needle 17 is replaced by the curved needle 129; therefore only the construction of the curved needle 129 is described in the following.

FIG. 48 shows the suturing device 3 wherein the curved needle 17 shown in FIGS. 3 and 4 is replaced by the curved needle 129. FIG. 49 is a figure viewed from the arrow A in FIG. 48. FIG. 50 is a cross sectional view taken from the line BB of FIG. 49. As shown in FIGS. 48 through 50, a hole 130 oblique to the rotational trajectory of the curved needle 129 is provided at the distal end of the curved needle 129. As shown in FIG. 50, the angle θ between the rotational trajectory plane and the hole 130 may be of any angle but is desirably 45 degrees.

The assembly and suturing methods of the third embodiment are same as the assembly method of second embodiment.

In addition to the advantages of first and second embodiments, since the hole 130 is located oblique to the rotational trajectory of the curved needle 129, the orientation of the hole 130 has the angle of 45 degrees with respect to the axes of the thread grasping/withdrawing means 69 and the instrument channel port 7 after tissue puncture by the hole 130, thus facilitating insertion of the thread grasping/withdrawing means 70, 74, 80, or 84 shown in FIGS. 23 through 26 into the space 131 shown in FIG. 49, catching of the thread 4, and removal of the thread 4 from the hole 130 in withdrawing. Thus the time required for grasping and withdrawing the thread may be further reduced.

Figure 51:
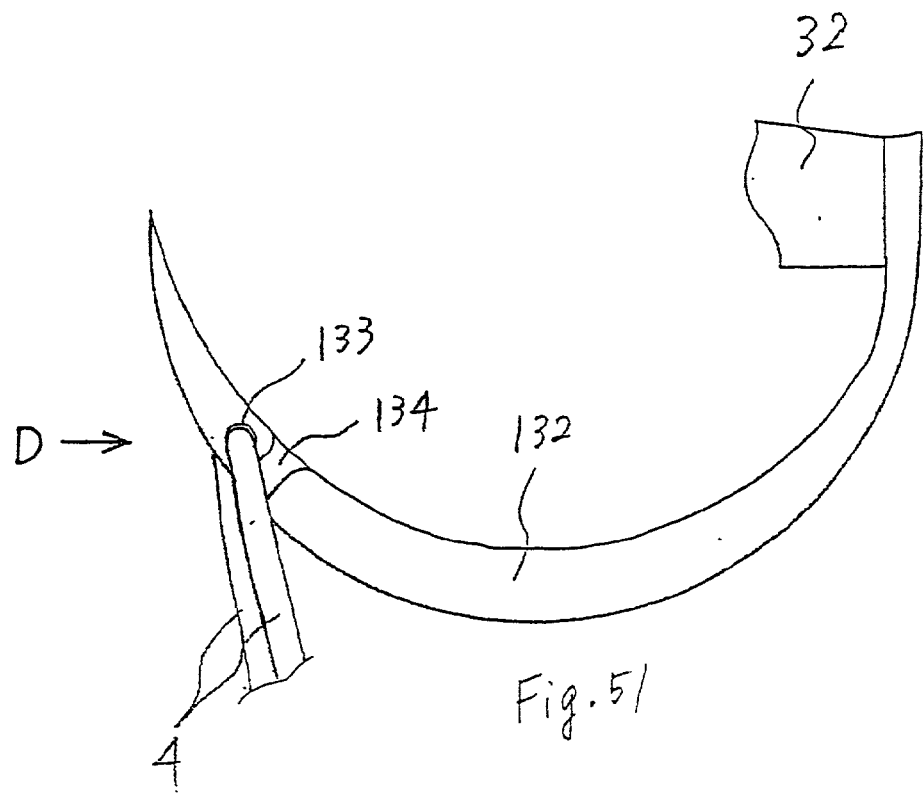
FIGS. 51 and 52 illustrate a variation of the third embodiment.
Figure 52:
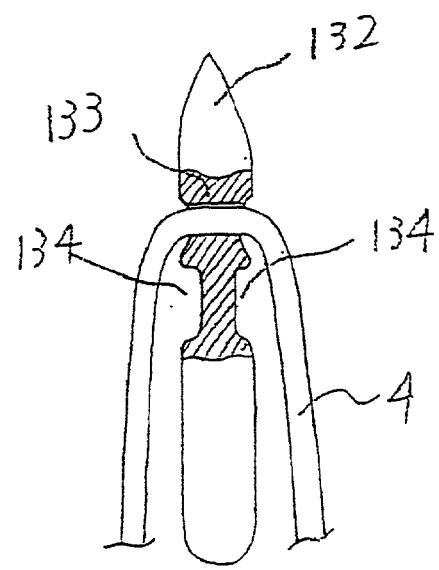

A variation of the third embodiment is shown in FIGS. 51 and 52. This variation has the same construction as the first embodiment except that the curved needle 17 is replaced by the curved needle 132; therefore only the construction of the curved needle 132 is described in the following.

FIG. 51 shows the suturing device 3 wherein the curved needle 17 shown in FIGS. 3 and 4 is replaced by the curved needle 132. FIG. 52 is a figure viewed from the arrow D in FIG. 51.

As shown in FIGS. 51 and 52, a hole 133 to allow passage of the thread 4 is provided at the distal end of the curved needle 132, and a slot 134 is formed in the vicinity of the hole 133.

The assembly and suturing methods this variation are same as in the third embodiment.

In addition to the advantages obtained with the first and second embodiments, the presence of the slot 134 facilitates insertion of the thread grasping/withdrawing means 70, 74, 80, or 84 shown in FIGS. 23 through 26 and catching of the thread 4. Thus the time required for grasping and withdrawing the thread may be further reduced.

Embodiment 4

Figure 53:
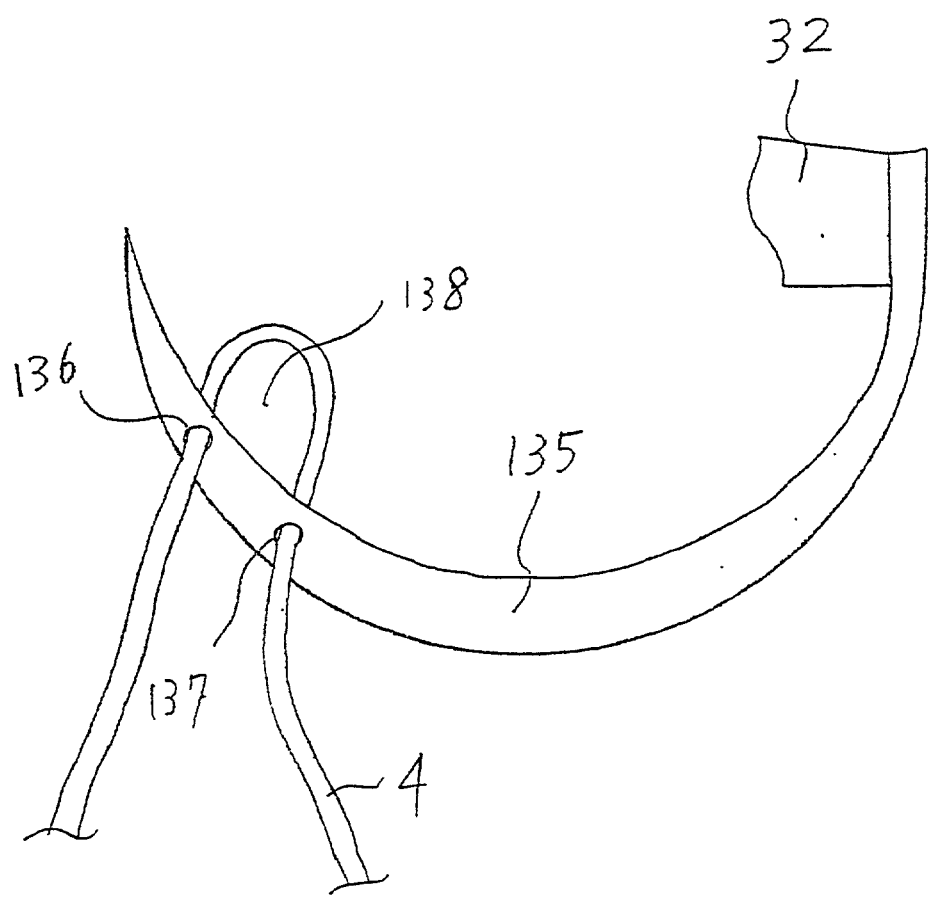
FIG. 53 illustrates a fourth embodiment of the present invention.

A fourth embodiment is shown in FIG. 53. This embodiment has the same construction as the first embodiment except that the curved needle 17 is replaced by the curved needle 135; therefore only the construction of the curved needle 135 is described in the following.

FIG. 53 shows the suturing device 3 wherein the curved needle 17 shown in FIGS. 3 and 4 is replaced by the curved needle 135. As shown in FIG. 53, two holes 136 and 137 are formed at specified interval at the distal end of the curved needle 135. The thread 4 passes through the holes 136 and 137 to form a space 138.

The assembly method of the fourth embodiment is same as that of the second embodiment.

The suturing method is almost the same as that of the first embodiment, in that it is changed to the procedure which one of the jaws of the thread grasping/withdrawing means 69 is inserted to the space 138 to grasp the thread 4 when the thread 4 shown in FIG. 40 is grasped and withdrawn by the thread grasping/withdrawing means 69. The hole 137 does not have slit shape as does the needle's slit 18 in the step of FIG. 43 of the first embodiment. Thus, this step is replaced by removal of the thread 4 from the hole 137 with the thread grasping/withdrawing means 69.

In addition to the advantages of the first embodiment, since the space 138 as shown in FIG. 53 is formed with the holes 136 and 137 to facilitate insertion of the thread grasping/withdrawing means 69, 70, 74, 80, or 84 shown in FIGS. 23 through 26 into the space 131 shown in FIG. 49, the thread 4 becomes easily caught. Thus the time required for grasping and withdrawing the thread may be further reduced.

Embodiment 5

Figure 54:
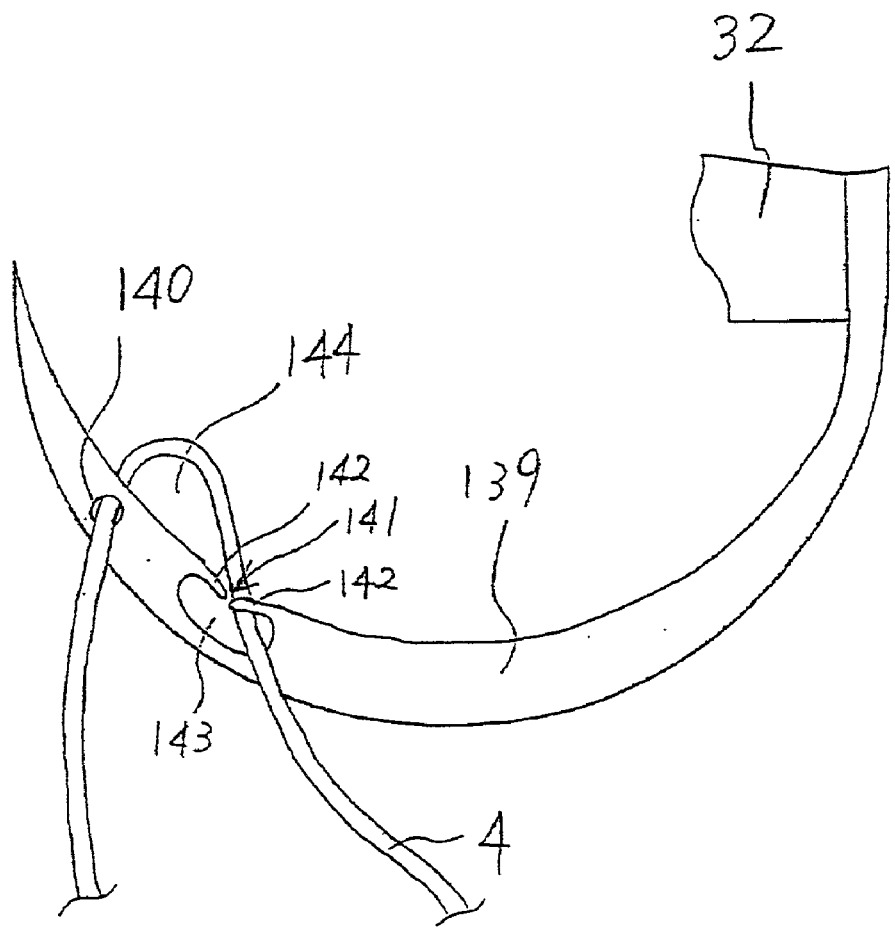
FIG. 54 illustrates a fifth embodiment of the present invention.

A fifth embodiment is shown in FIG. 54. This embodiment has the same construction as the first embodiment except that the curved needle 17 is replaced by the curved needle 139; therefore only the construction of the curved needle 139 will be described.

FIG. 54 shows the suturing device 3 wherein the curved needle 17 shown in FIGS. 3 and 4 is replaced by the curved needle 139. As shown in FIG. 54, a hole 140 and a needle's slit 141 are formed at specified interval at the distal end of the curved needle 139. The needle's slit 141 is formed with two flaps 142 to have a width slightly smaller than the external diameter of the thread 4, and the thread 4 is pressed into the needle's slit 141 to elastically deform the thread 4 or the flaps 142 and to accommodate the thread 4 in the engagement member 143. Therefore, a certain degree of force is required to remove the thread 4 from the engagement member 143. The thread 4 passes through the hole 140 and engagement member 143 to form a space 144. As long as the thread 4 is not withdrawn during suturing as in the first embodiment, the width of the needle's slit 141 may be larger than the external diameter of the thread 4.

The assembly method of the fifth embodiment is same as that of the second embodiment.

The suturing method is almost the same as that of the first embodiment in that it is changed to the procedure which one of the jaws of the thread grasping/withdrawing means 69 is inserted to the space 144 to grasp the thread 4 when the thread 4 shown in FIG. 40 is grasped and withdrawn by the thread grasping/withdrawing means 69. Since the slit 141 is formed, the thread may be removed as in the procedure of FIG. 43.

In addition to the advantages of the first embodiment, the hole 140 and the engagement member 143 as shown in FIG. 54 form the space 144, thus facilitating insertion of the thread grasping/withdrawing means 69, 70, 74, 80, or 84, and catching of the thread 4. Since the needle's slit 141 is formed, the thread may be readily removed at the second stitch as shown in FIG. 43, thus further reducing the time required for grasping and withdrawing the thread.

Embodiment 6

Figure 55:
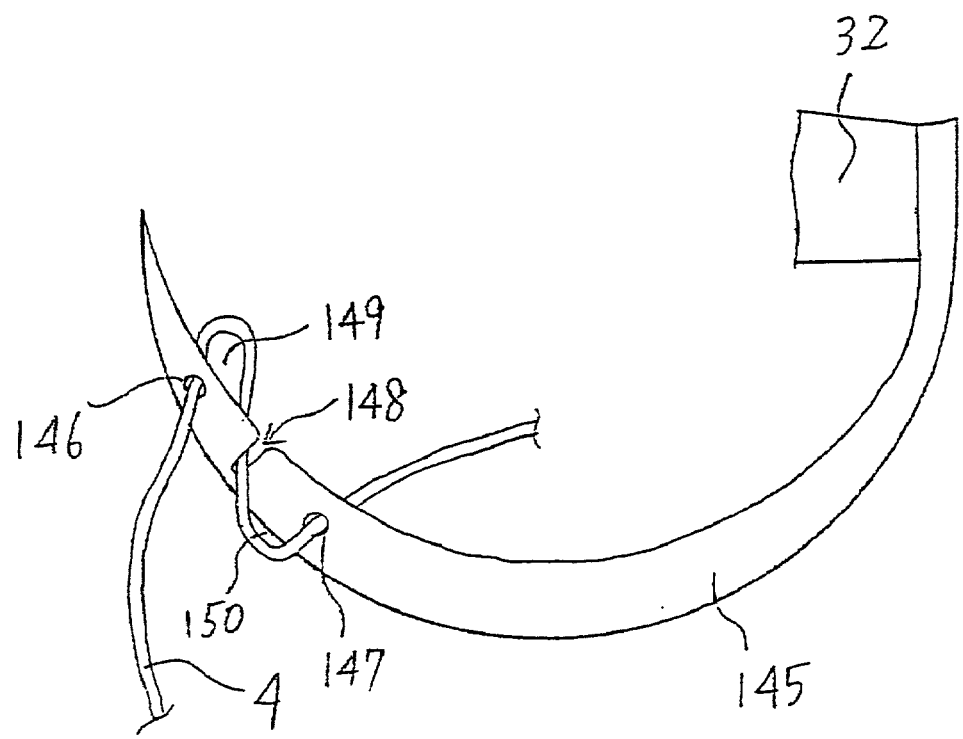
FIG. 55 illustrates a sixth embodiment of the present invention

A sixth embodiment is shown in FIG. 55. It has the same construction as the first embodiment 1 except that the curved needle 17 is replaced by the curved needle 145; therefore only the construction of the curved needle 145 will be described. FIG. 55 shows the suturing device 3 wherein the curved needle 17 shown in FIGS. 3 and 4 is replaced by the curved needle 145.

As shown in FIG. 55, two holes 146 and 147 are formed at specified interval at the distal end of the curved needle 145 to form the needle's slit 148 between the holes 146 and 147. The thread 4 passes through the holes 146 and 147 and the needle's slit 148 to form a space 149 and another space 150. The needle's slit 148 may have the same construction as the needle's slit 141 in FIG. 54.

The assembly method of the sixth embodiment is same as that of the second embodiment.

The suturing method is described below by referring to FIGS. 56 through 63.

Figure 56:
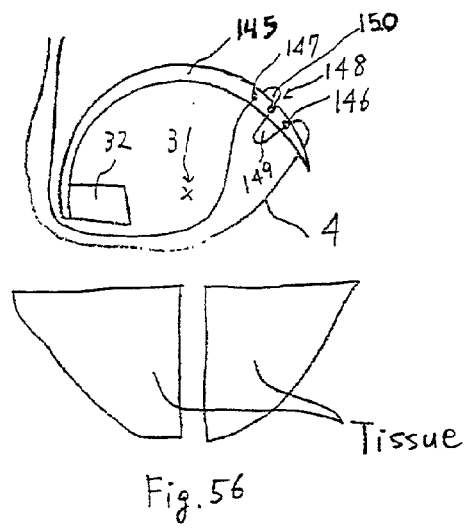
FIGS. 56 through 63 show the suturing method carried in the sixth embodiment.

Insert the distal end of the flexible portion 16 set as shown in FIG. 56 to the suturing target site in the body cavity.

Rotate the handle 50 clockwise shown in FIG. 19 to move the curved needle 145 to the position shown in FIG. 56. Then press the tissue protective member 5 shown in FIG. 2 against the suturing site, and force the suturing device 3 in the distal end direction to urge the fixing needle 23 into the tissue. Then securely fix the suturing device 3 at the suturing target site. By fixing it, the tissue is not dislocated during puncture of the curved needle 145.

Figure 57:
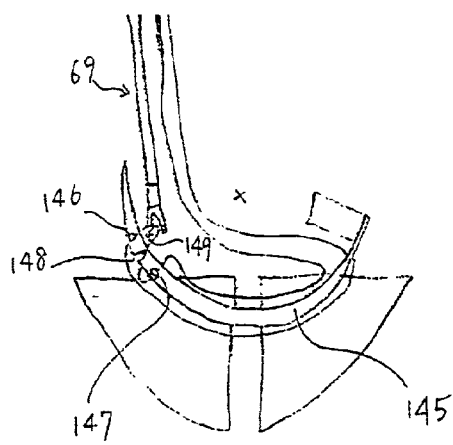
Figure 58:
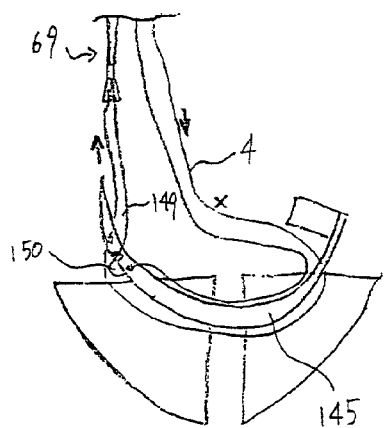
Figure 59:
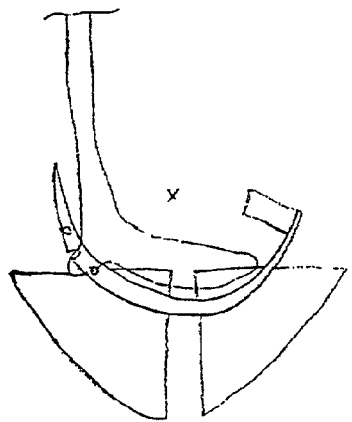

Rotate the handle 50 counterclockwise to force the curved needle 145 to puncture across the suturing target site as shown in FIG. 57, push the one of the jaws of the thread grasping/withdrawing means 69 inserted via the instrument channel port into the space 149 projecting from the tissue as shown in FIG. 57, and lead an end of the thread 4 out of the body cavity as shown in FIGS. 58 and 59.

Figure 60:
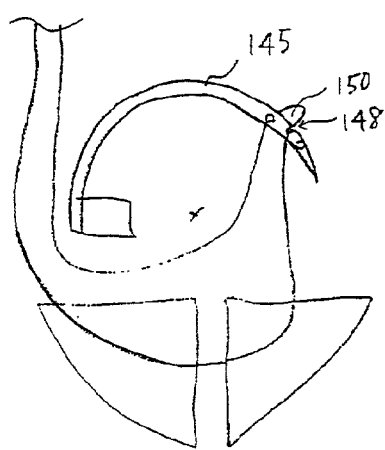

Then rotate the handle 50 clockwise as shown in FIG. 60 to remove the curved needle 145 from the tissue.

Figure 61:
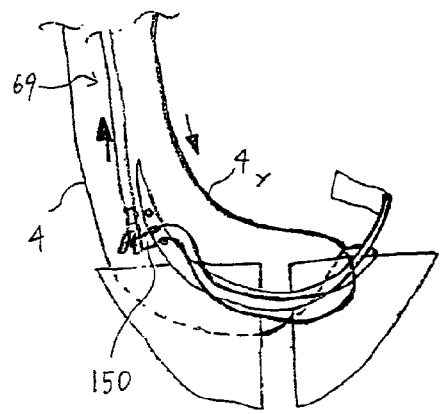
Figure 62:
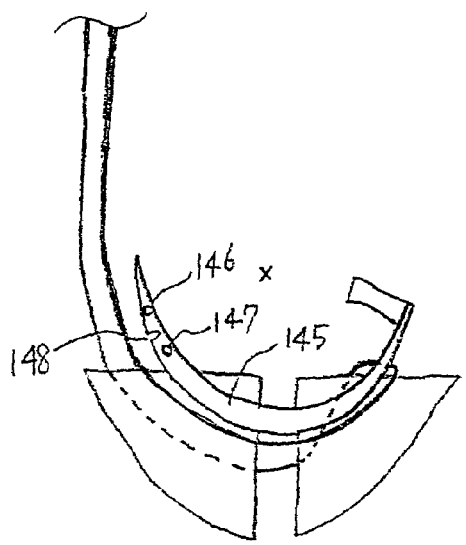

Change the angle of the endoscope as shown in FIG. 61 to puncture slightly away from the previous puncture, hold the thread 4 so as to advance one of the jaw of the thread grasping/withdrawing means 69 into the space 150, remove the thread 4 from the needle's slit 148, and lead the other end of the thread 4 out of the body cavity as shown in 62 while keeping the already sutured thread in place.

Figure 63:
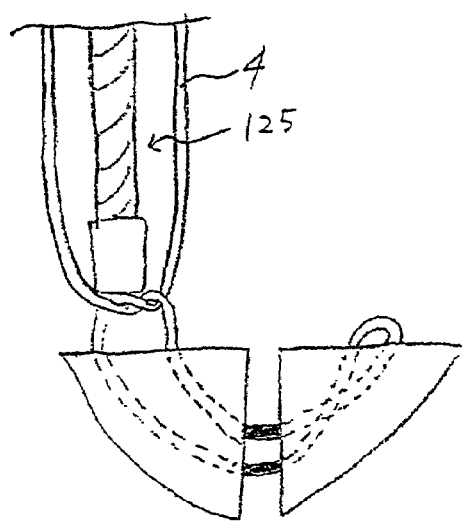

Tie the ends of the thread 4 out of the body cavity as shown in FIG. 63, and push the knot to the suturing site with the knot pusher 125 inserted in the instrument channel port 7. Repeat the step several times to ensure secure tightening of the knot and complete the suturing.

In addition to the advantages of the first embodiment, since the holes 146 and 147 and the needle's slit 148 form the spaces 149 and 150 as shown in FIG. 54 to facilitate insertion of the thread grasping/withdrawing means 69, 70, 74, 80, or 84, the thread is readily caught both at the first and second stitches. Since the needle's slit 148 is formed, the thread may be readily removed at the second stitch, thus further reducing the time required for grasping and withdrawing the thread.

Embodiment 7

Figure 64:
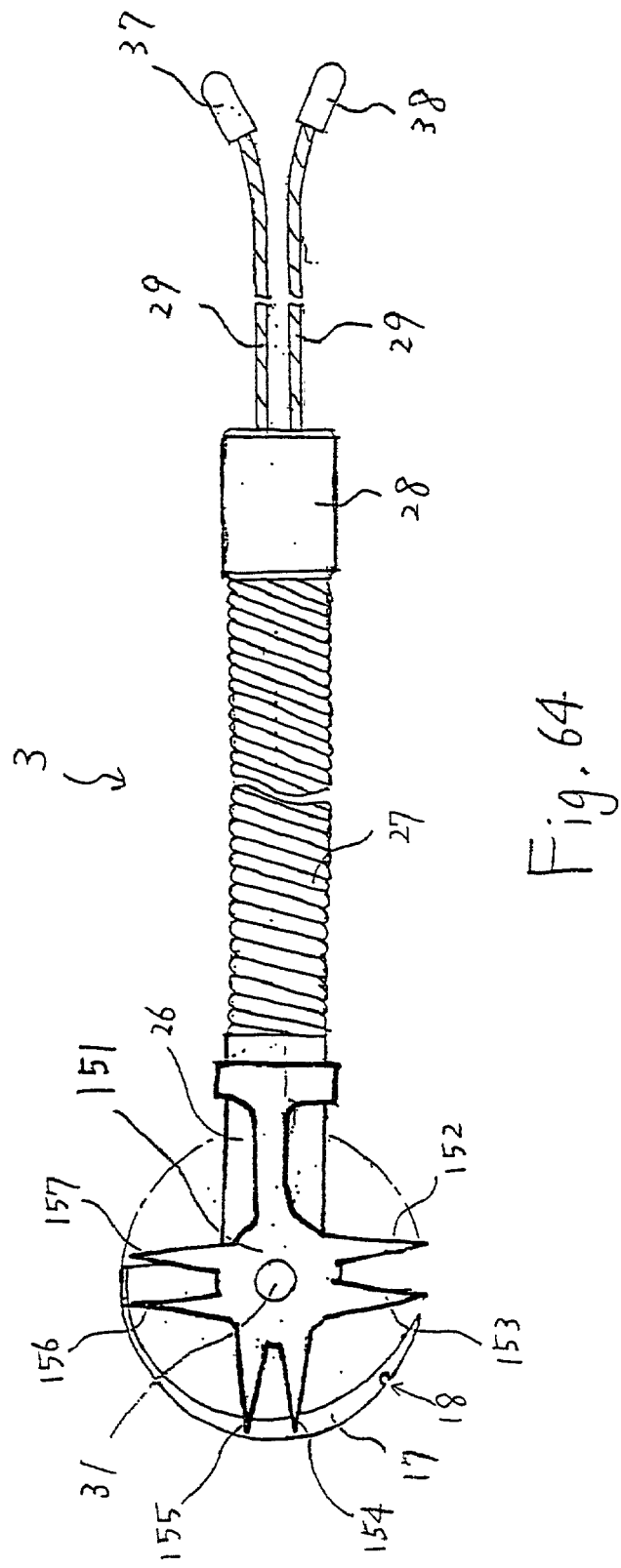
FIG. 64 illustrates a seventh embodiment of the present invention.

The seventh embodiment, which is shown in FIG. 64, has the same construction as the first embodiment, except that the tissue fixing member 25 of the first embodiment 1 shown in FIG. 3 is replaced by tissue fixing member 151 as shown in FIG. 64; therefore only the construction of the tissue fixing member 151 is described.

As shown in FIG. 64, fixing needles 152 through 157 are formed on the tissue fixing member 151. The needles 152 and 153, 154 and 155, and 156 and 157 are formed at specified intervals to make pairs respectively, and each pair is formed at 90-degree intervals.

Figure 65:
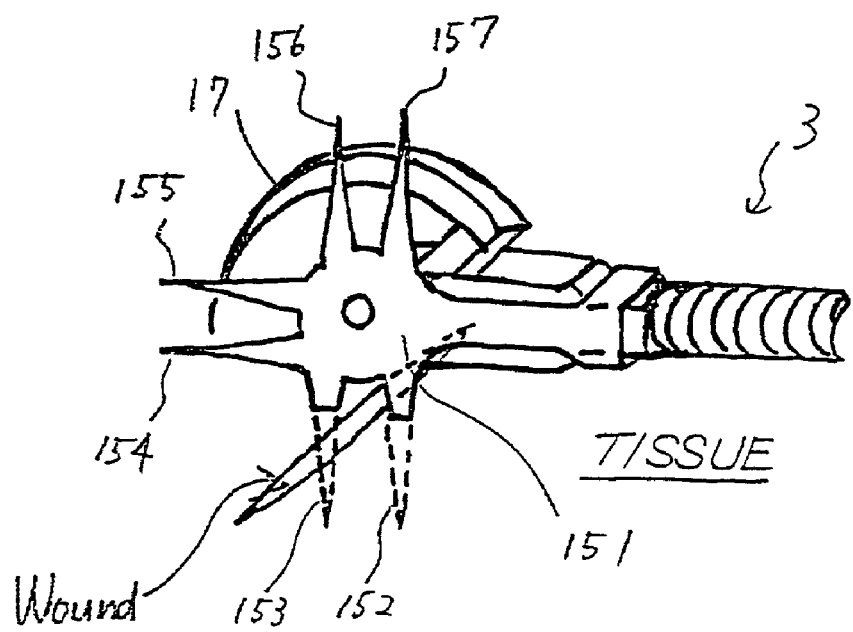
FIG. 65 is a diagram helpful in understanding the suturing method of the seventh embodiment.

The assembly method of the seventh embodiment 7 is same as that of the first embodiment. The suturing method is same as the one shown in FIGS. 38 through 45 in relation to first embodiment except that the suturing device 3 is fixed as in FIG. 38 of the first embodiment, but the wound is located between the fixing needles 152 and 153 as shown in FIG. 65. Other procedures are same as in the first embodiment and will not be further described.

In addition to the advantages of the first embodiment, since the suturing device 3 is fixed with the fixing needles which lie across the wound, and the tissue is not dislocated during puncture, the curved needle 17 readily punctures the tissue.

Embodiment 8

Figure 66:
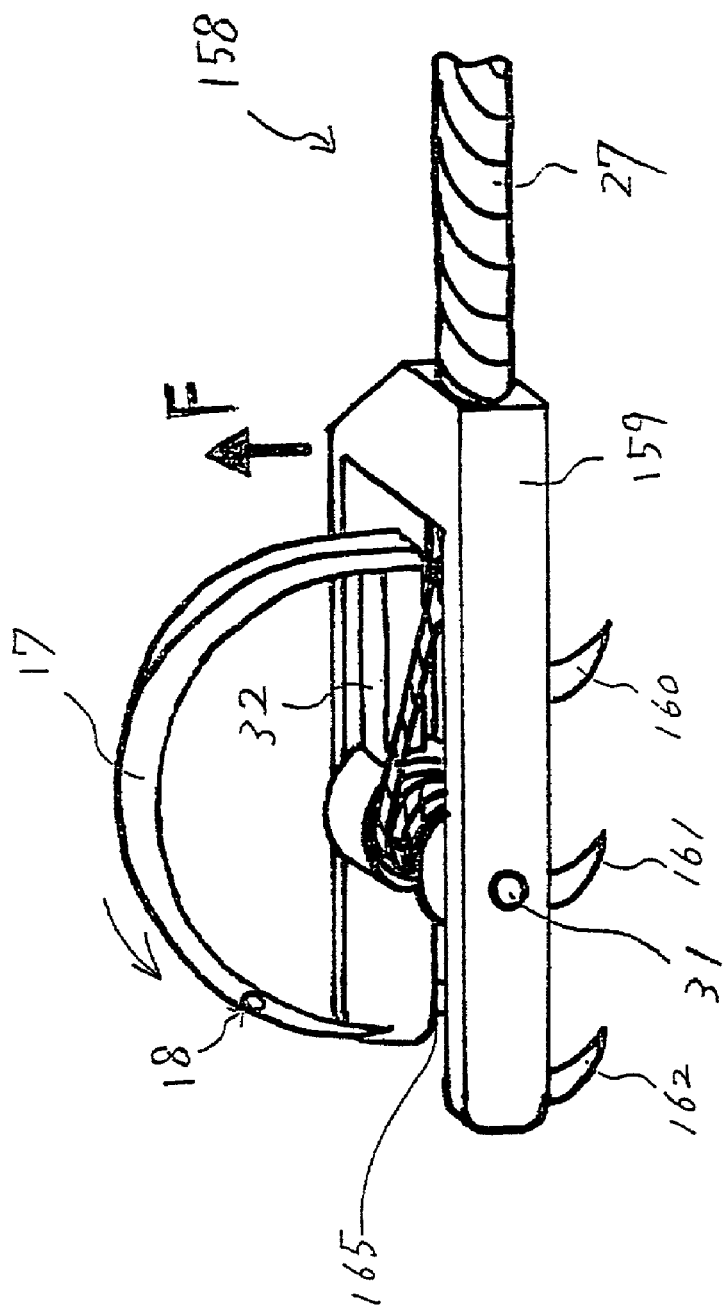
FIGS. 66 through 68 illustrate an eighth embodiment of the present invention.
Figure 67:
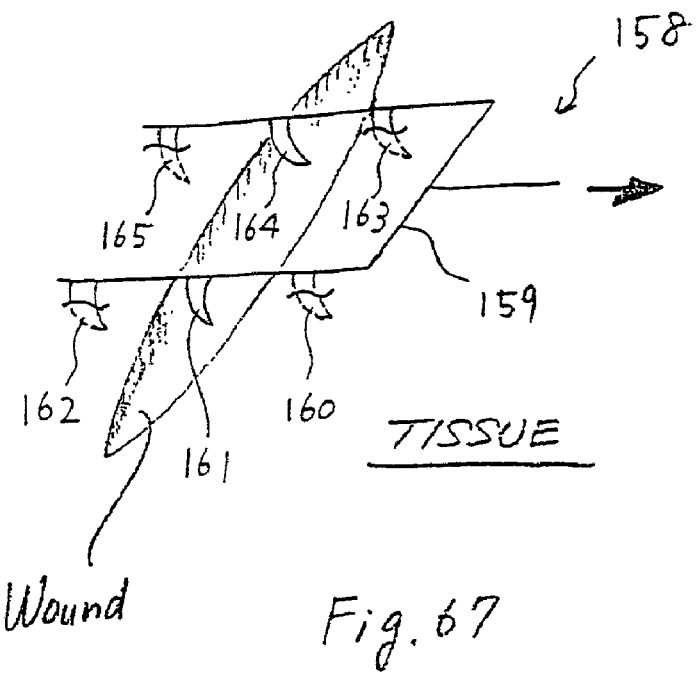
Figure 68:
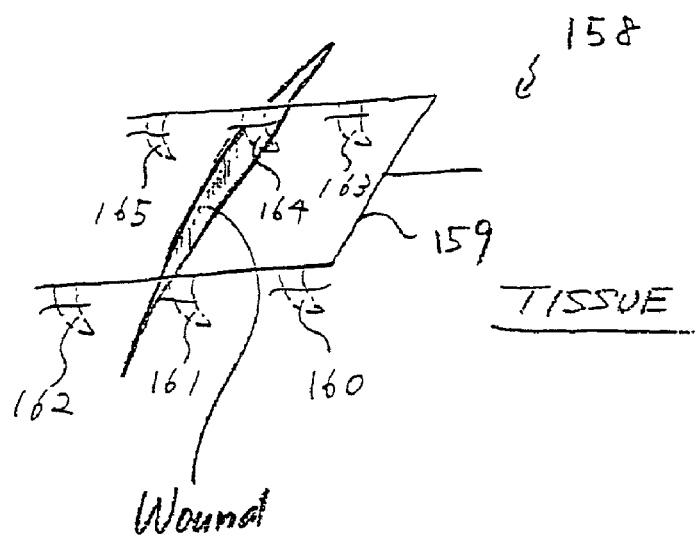

An eighth embodiment is shown in FIGS. 66 through 68. As shown in FIG. 66, this embodiment has the same construction as the first embodiment, except that the fixing curved needles 160 through 165 are fixed to the supporting member 159 instead of the tissue fixing member 25.

Although six fixing curved needles are provided in this embodiment, the number of the fixing curved needles may be any number as long as it is one or more. As for the fixing curved needles shown in FIG. 67, in particular, two of them 162 and 165 may be sufficient. The fixing curved needles may be detachable from the supporting member 159. The fixing curved needles may be straight in some cases, not curved.

The fixing curved needles 160 through 165 are fixed so that the pointed end faces the operator side of the suturing device 158 as shown in FIG. 66, and the size of the wound may be minimized by pulling the suturing device 158 toward the operator side as shown in FIG. 68 after the suturing device is pressed against the sound. Since the fixing curved needles 160 through 165 are curved, the upward force F to separate the suturing device 158 from the tissue as shown in FIG. 66 when the curved needle 17 punctures the tissue, thus attaining a deep suture into the tissue.

The operation is same as in the first embodiment and will not be described again. In addition to the advantages of the first embodiment, since the suturing device 158 may be fixed in the tissue against the reaction caused in puncture by the curved needle 17, a reliable suture may be ensured.

Embodiment 9

Figure 69:
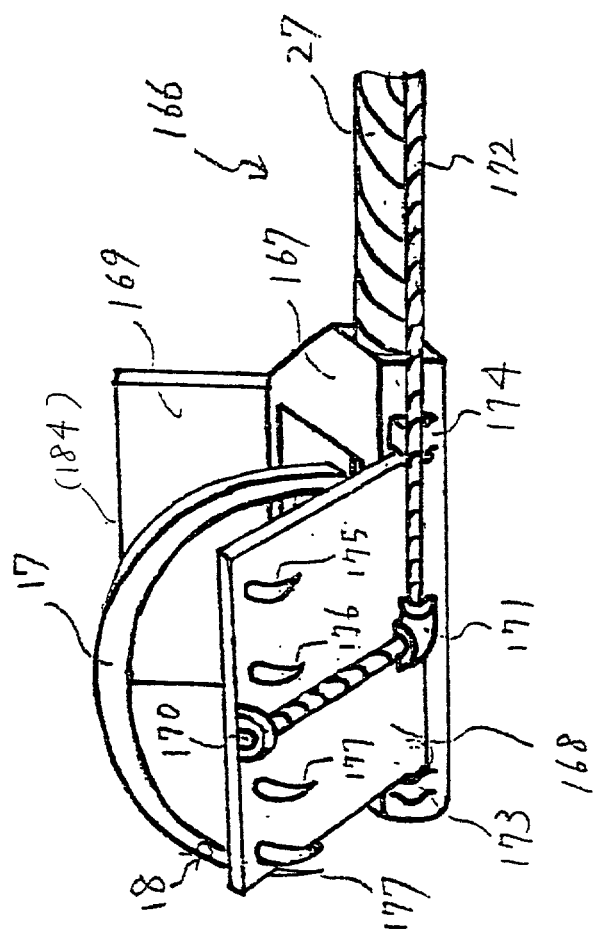
FIGS. 69 through 71 illustrate a ninth embodiment of the present invention.
Figure 70:
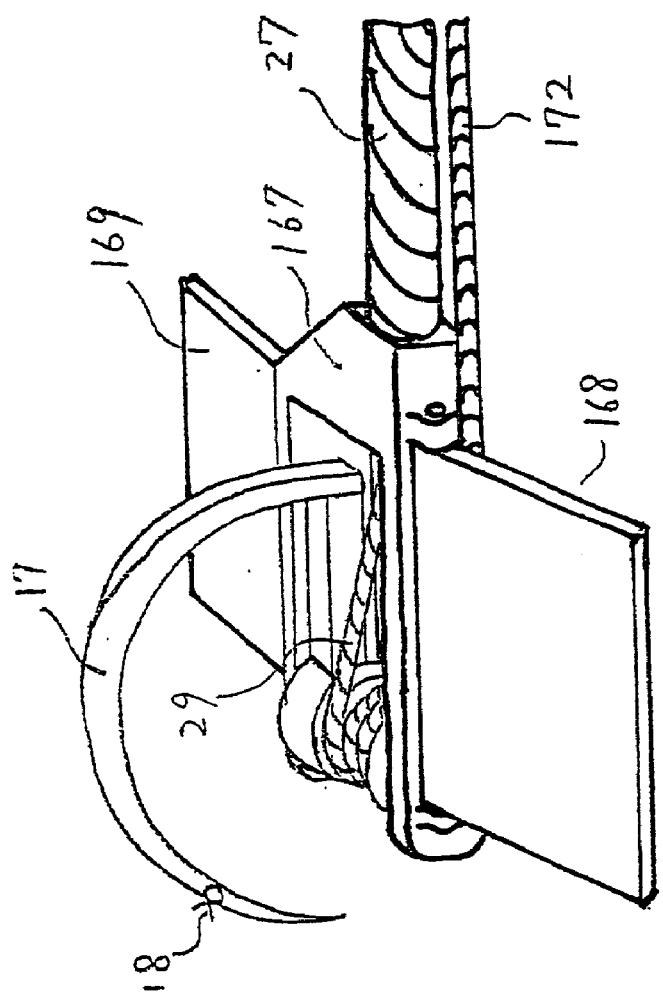
Figure 71:
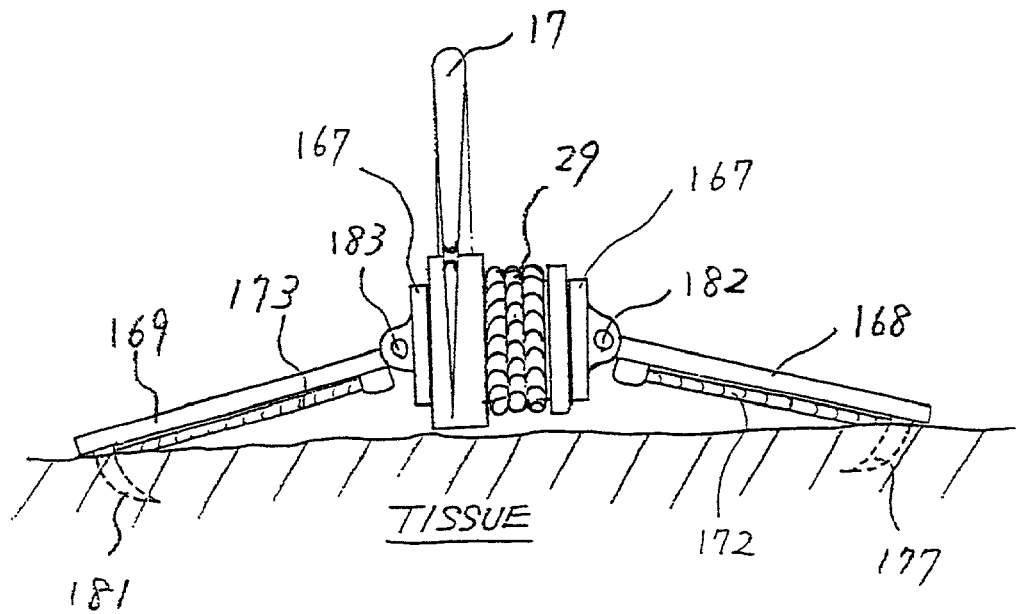

FIGS. 69 through 71 illustrate a ninth embodiment which has the same construction as the first embodiment, except that the tissue fixing member 25 of the first embodiment is replaced by flaps 168 and 169 movably provided on the supporting member 167 via the shafts 182 and 183 and fixing curved needles 175 through 181 are respectively provided on the flaps 168 and 169. The fixing curved needles 179 and 180 are fixed to the flap 169 although not shown in the figure. The flaps 168 and 169 are movable by pushing or pulling the operating wires 172 and 173, whose ends are respectively fixed to the stopper members 170 and 184 on the flaps 168 and 169 and which are connected to the operation unit on the operator side not shown in the figure via the guide members 171 and 185. Although the stopper member 184 and the guide member 185 are not shown in the figure, they have structure symmetric to those on the flap 168. The fixing curved needles may be detachable from the flap 168. The fixing curved needles may be straight in some cases, not curved.

While the suturing device 3 is fixed against the tissue by the tissue fixing member 25 in the first embodiment, in this embodiment the fixing curved needles 175 through 181, fixed on two flaps, or by four on each flap, are securely fixed against the tissue by manipulating the operating wires 172 and 173 as shown in FIG. 71. Otherwise the suturing method is the same as in the first embodiment and will not be again described.

In addition to the advantages of the first embodiment, 166 may be securely fixed against the tissue by manipulating the operating wires 172 and 173 not by pressing 166 or the scope against the tissue.

Embodiment 10

Figure 72:
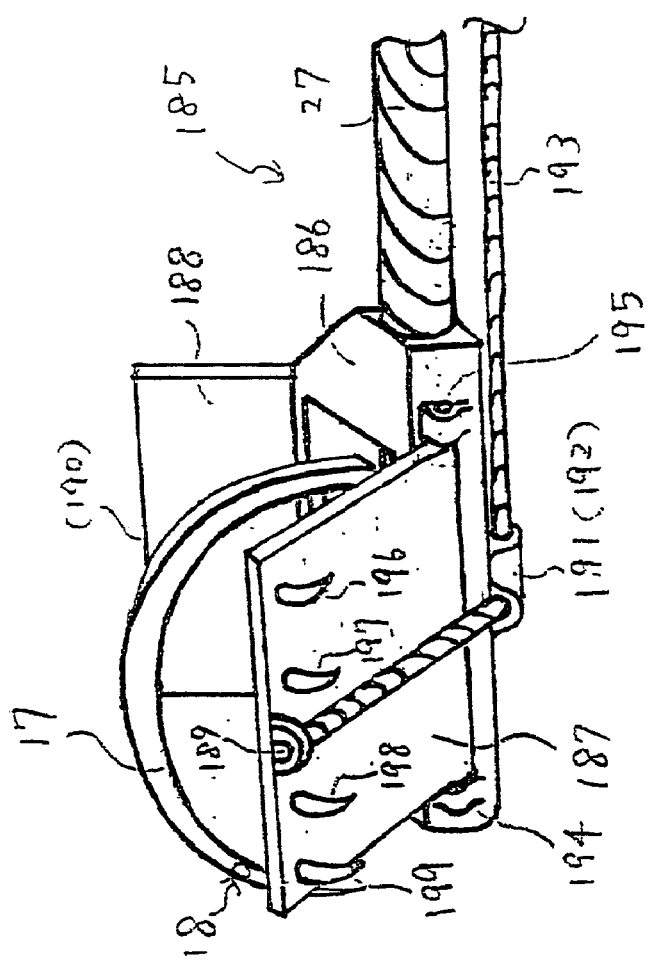
FIGS. 72 through 74 illustrate a tenth embodiment of the present invention.
Figure 73:
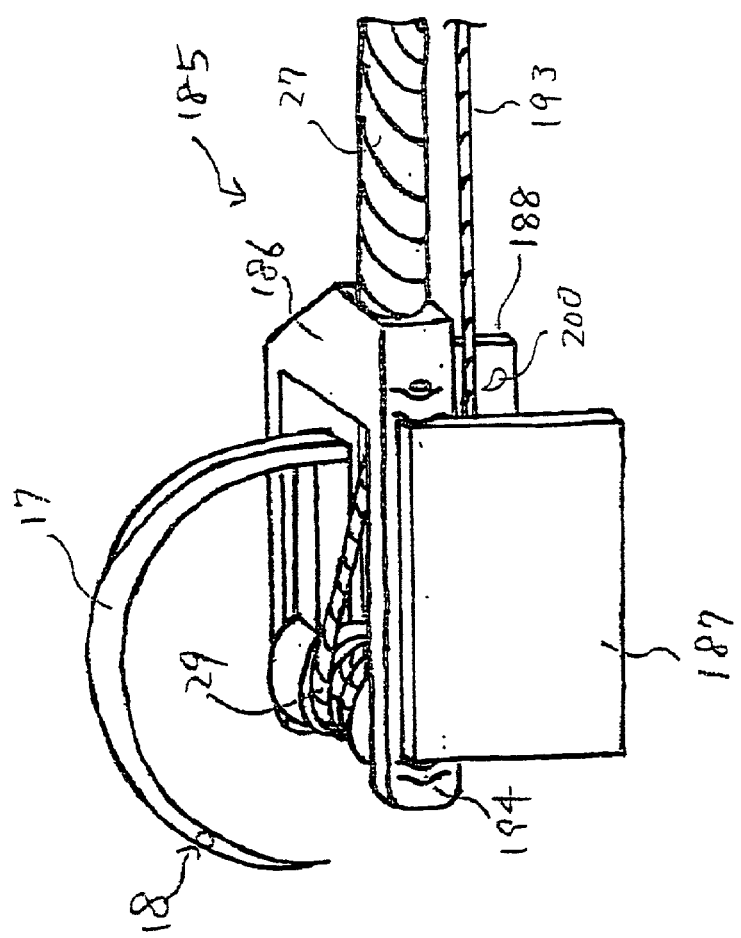
Figure 74:
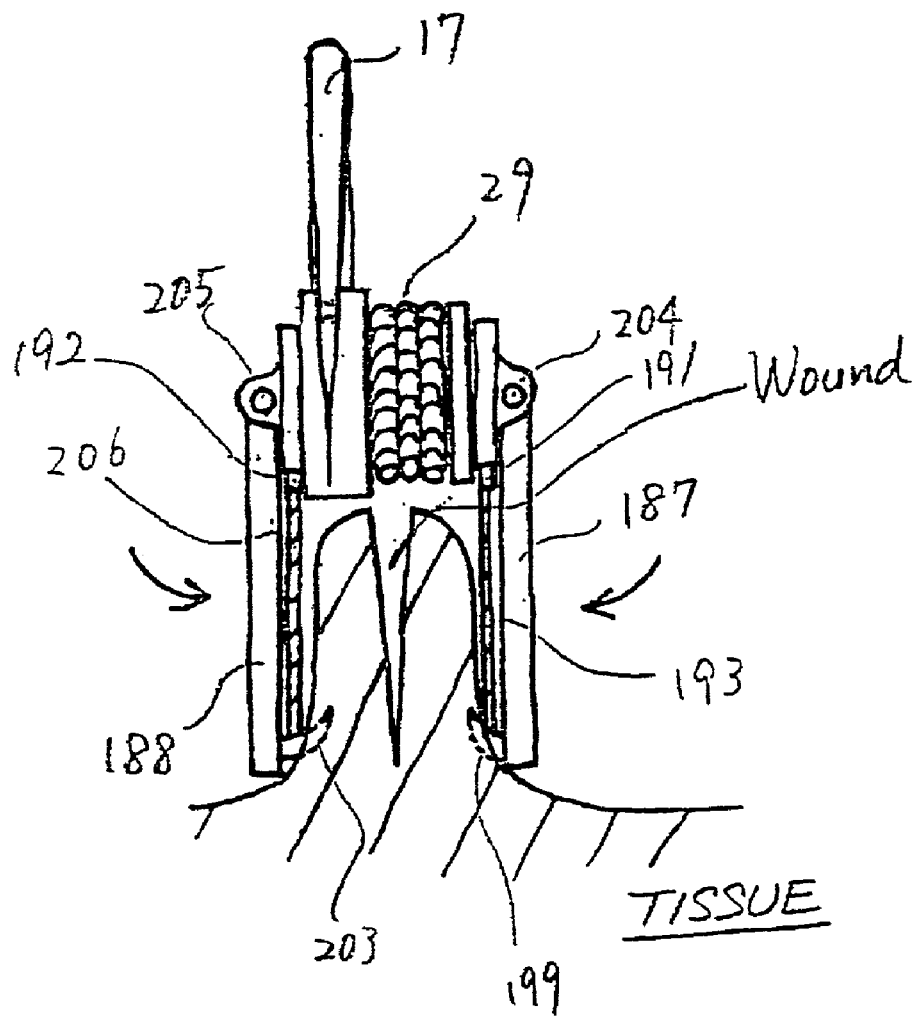

The tenth embodiment is shown in FIGS. 72 through 74. This embodiment has the same construction as the first embodiment except that the tissue fixing member 25 of the first embodiment is replaced by flaps 187 and 188 movably provided on the supporting member 186 via the shafts 204 and 205 and fixing curved needles 196 through 203 are respectively provided on the flaps 187 and 188. The fixing curved needles 201 and 202 are fixed to the flap 188 although not shown in the figure. The flaps 187 and 188 are movable by pushing or pulling the operating wires 193 and 206, whose ends are respectively fixed to the stopper members 189 and 190 on 193 and 206 and which are connected to the operation unit on the operator side not shown in the figure via the guide members 191 and 192. Although the stopper member 190 and the guide member 192 are not shown in the figure, they have structure symmetric to those on the flap 187.

While the tenth embodiment has almost the same structure as the ninth embodiment, the movable envelope of the flaps 187 and 188 are made larger as shown in FIG. 74. Otherwise, the suturing method is same as in the first embodiment and not further described.

In addition to the advantages of the first and ninth embodiments, the large movable envelope of the flaps attains smaller wound and secure fixation on the tissue.

Embodiment 11

Figure 75:
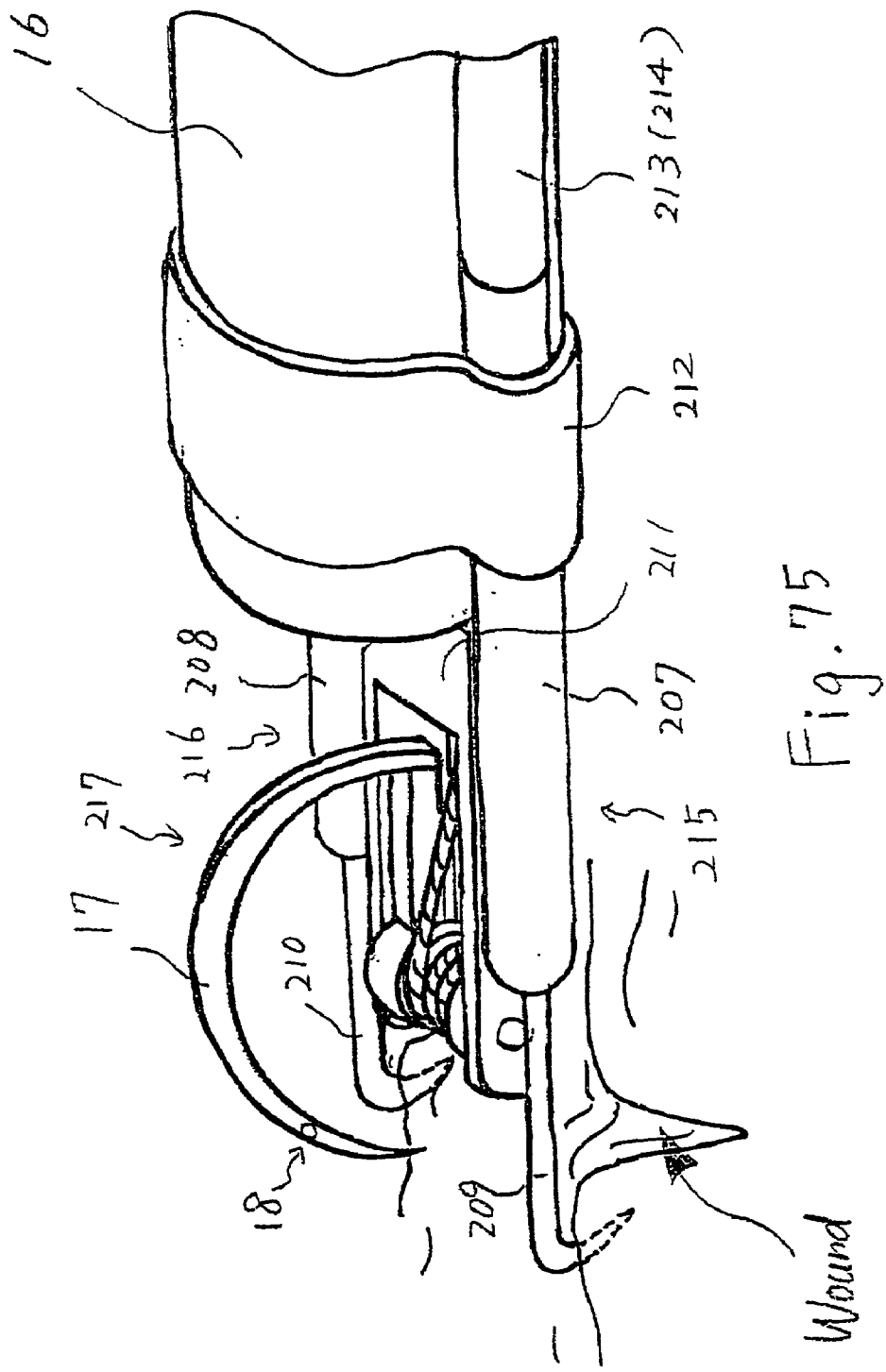
FIG. 75 illustrates an eleventh embodiment of the present invention
Figure 76:
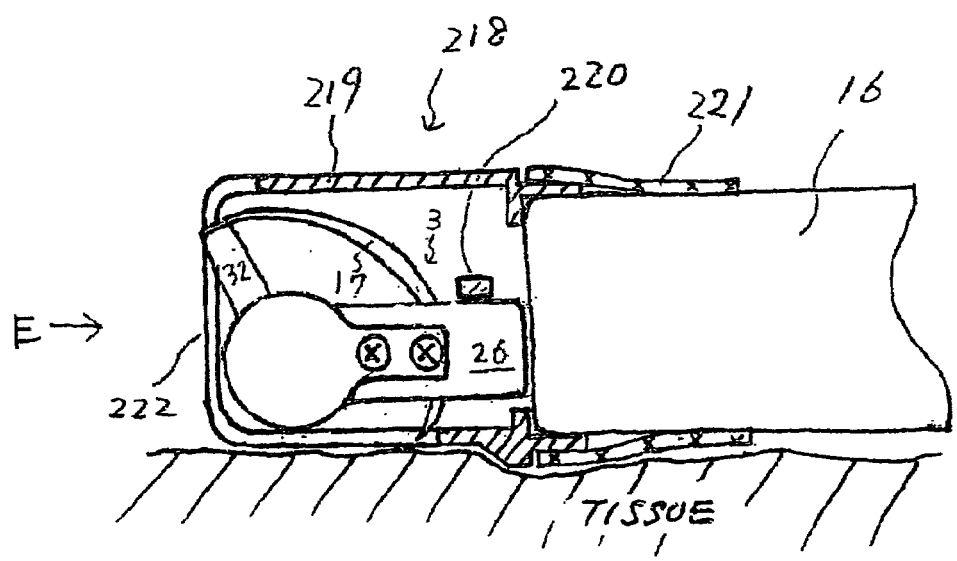
FIGS. 76 through 81 illustrate a twelfth embodiment of the present invention.
Figure 77:
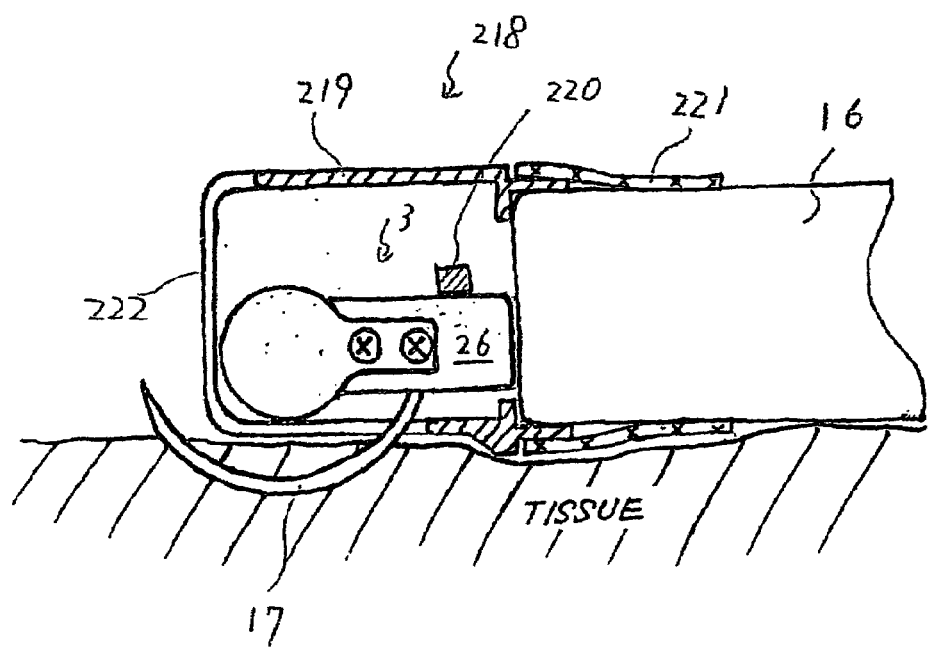
Figure 78:
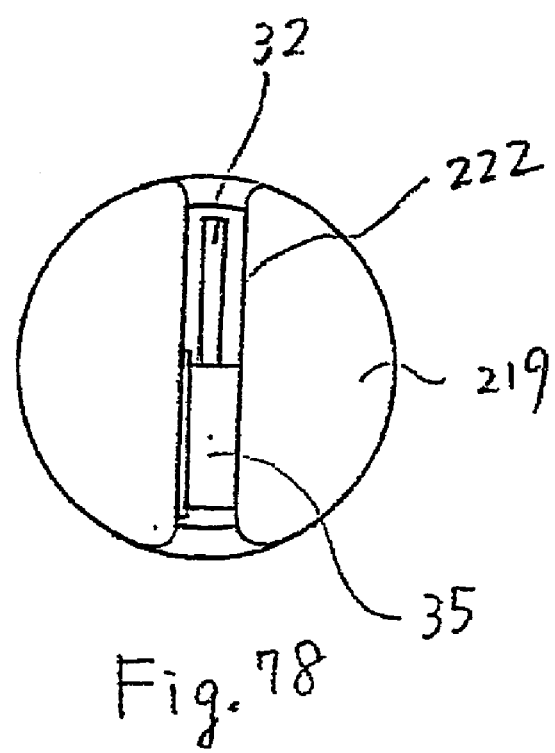

FIG. 75 illustrates an eleventh embodiment of the present invention, which has a structure in which tissue fixing members 215 and 216 are fixed to the flexible portion 16 using a band 212 in the construction of the first embodiment. Although the tissue protective member 5 with the protective member's slit 21 as shown in FIG. 2 is not shown in FIG. 75, a tissue protective member as shown in the first embodiment having a slit to allow the tissue fixing members 215 and 216 to pass through may be provided. In the tissue fixing member 215, a pipe 207 and a flexible tubular member 213 are connected, and a hook 209 is movably disposed in their inner cavities. The operator side of the hook 209 is fixed to the operation unit not shown in the figure. The distal end of the hook 209 is bent at least once, and the distal end is pointed. The tissue fixing member 216 has the same structure as the tissue fixing member 215. Although the pointed end of the hook 209 is bent slightly toward the operator side in this embodiment, it may be bent perpendicularly to the axis.

In accordance with the eleventh embodiment, the pointed ends of the hooks 209 and 210 puncture the tissue by advancing or withdrawing the operation unit on the operator side not shown in the figure and are pulled toward the operator side as shown in FIG. 75 to close the wound so that the suturing device 217 may be securely fixed against the tissue. Although the tissue fixing members 215 and 216 are fixed on the flexible portion 16 with the band 212 in this embodiment, the tissue fixing members 215 and 216 may be fixed on the part 211 on the suturing device 217.

In addition to the advantages of the first, ninth and tenth embodiments, the eleventh embodiment is characterized by its simple construction to reduce the cost. Since the movable envelopes of the hooks 209 and 210 may be made large, a large wound may be closed.

Embodiment 12

FIGS. 76 through 81 illustrate a twelfth embodiment of the present invention in which, the tissue fixing member 25 is removed from the first embodiment, and the tissue protective member 5 is replaced by a tissue protective member 218. The tissue protective member 218, similar to the first embodiment, comprises a protective member 219 and a fixing member 221, and a protective member's slit 222 is formed on the protective member 219. The protective member's slit 222 has a width at least to allow the curved needle 17 to pass. A stopper 220 is provided to hold the suturing device 3 in the protective member 219 during puncture.

Figure 79:
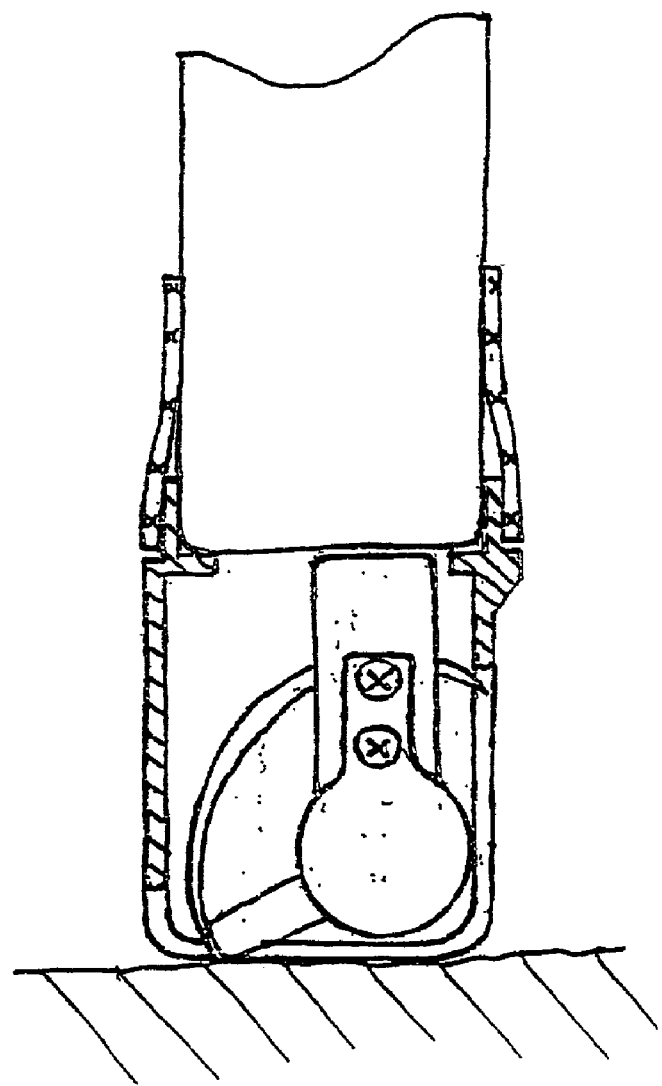
Figure 80:
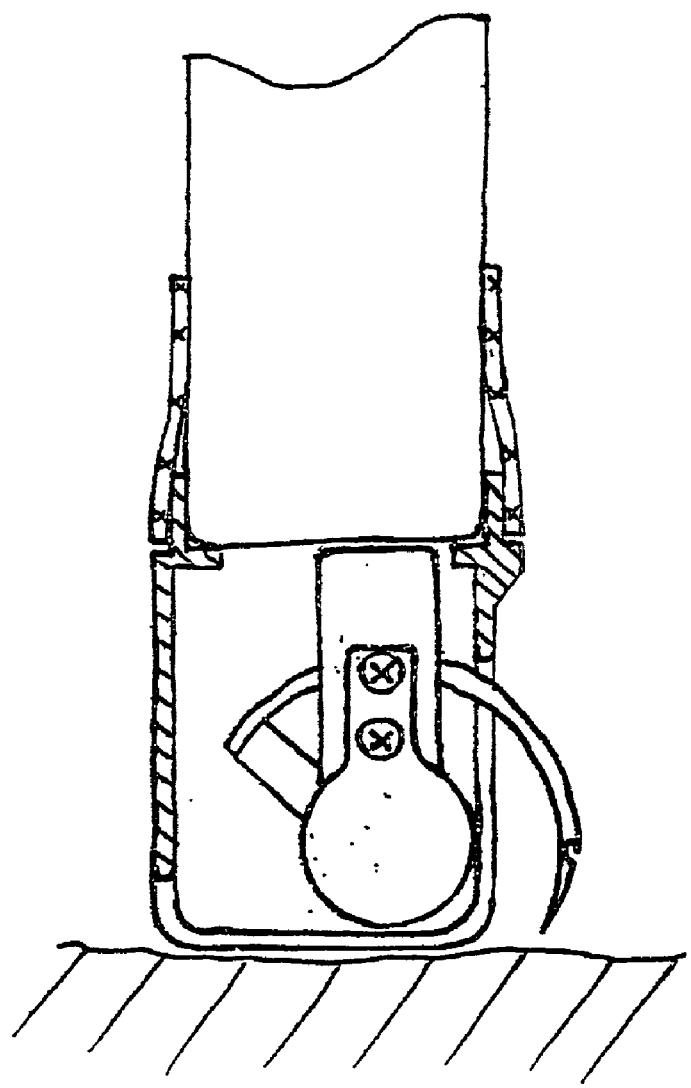
Figure 81:
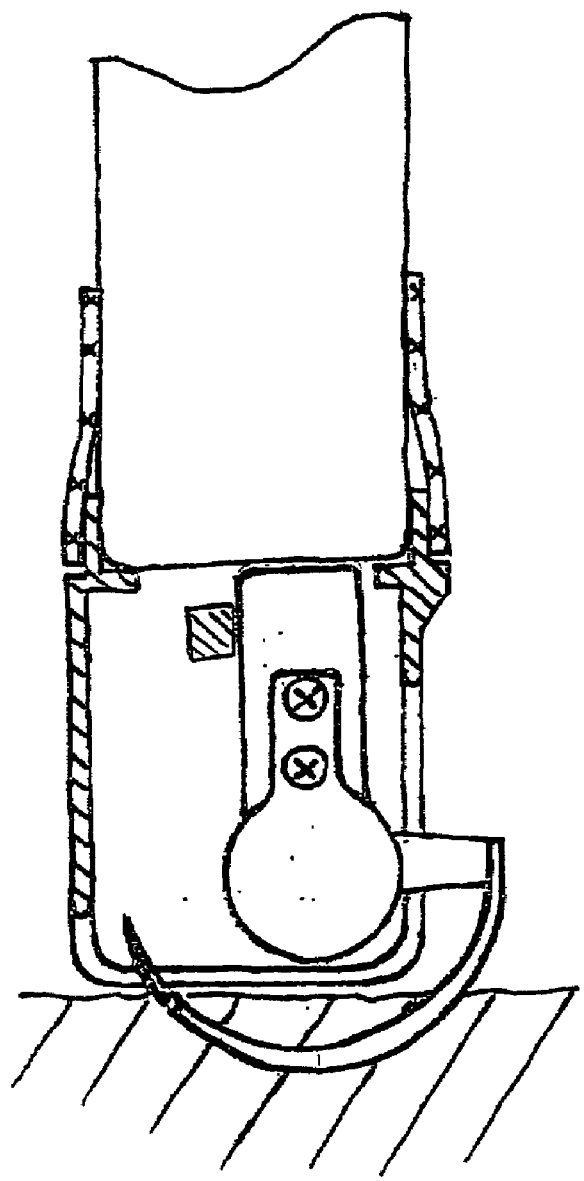
Figure 82:
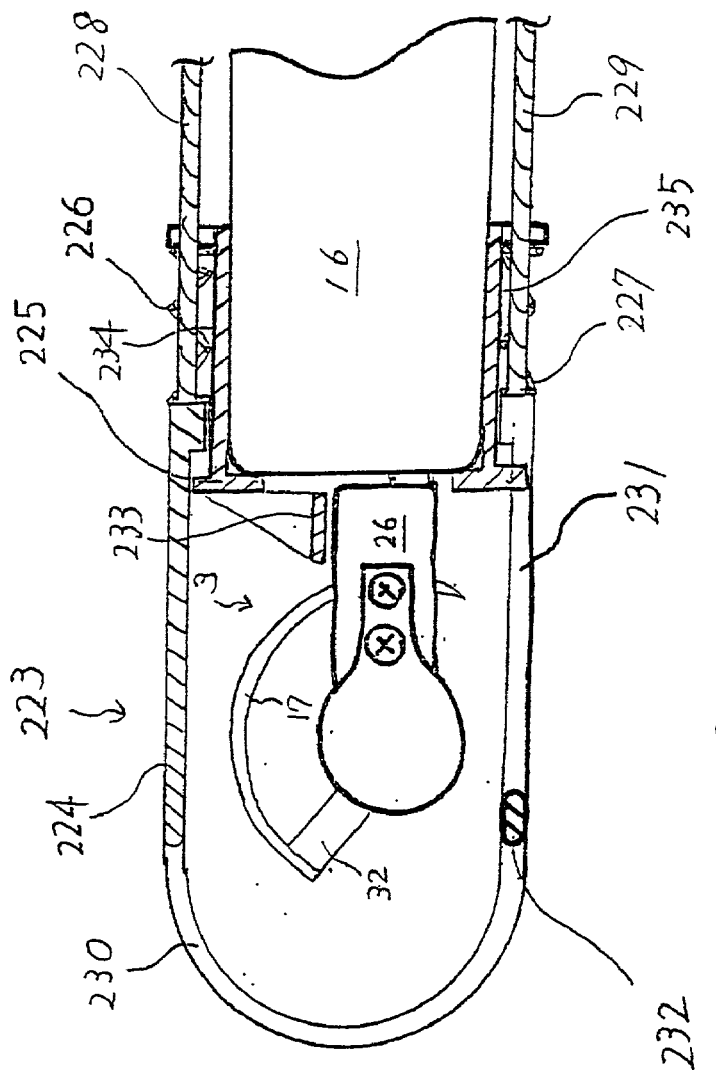
FIGS. 82 through 86 illustrate a thirteenth embodiment of the present invention.

As shown in FIGS. 76, 77 and 79 through 81, twelfth embodiment may fix the tissue by pressing the tissue protective member 218 against the suturing site by adjusting the angle of the scope. The twelfth embodiment attains puncture in the tangential direction shown in FIGS. 76 and 77 and sutures in the forward direction as shown in FIGS. 79 through 81.

The suturing procedure is same as in the first embodiment.

In addition to the advantages of the first embodiment, the twelfth embodiment is characterized by its simple construction to reduce the cost.

Embodiment 13

FIGS. 82 through 86 illustrate a thirteenth embodiment of the present invention having the tissue fixing member 223 at the distal end of the flexible portion 16 of first embodiment. The tissue fixing member 223 comprises a fixing portion 225 shaped in cylinder to be fitted and fixed to the distal end of the flexible portion 16, a movable portion 224 which is slidable along grooves 234 and 235 of the fixing portion 225, springs 226 and 227 for constantly urging the movable portion 224 toward the distal end, and operating wires 228 and 229 fixed at its end to the movable portion 224. The operating wires 228 and 229 are fixed to the operation unit not shown in the figure and may advance or withdraw by advancing or withdrawing the operation unit. Slits 230 and 231 are formed on the movable portion 224, and a presser member 232 is formed between the slits 230 and 231. A stopper 233 is provided at the distal end of the fixing portion 225 to hold the suturing device 3 against upward tendency due to puncture resistance during puncture.

Figure 83:
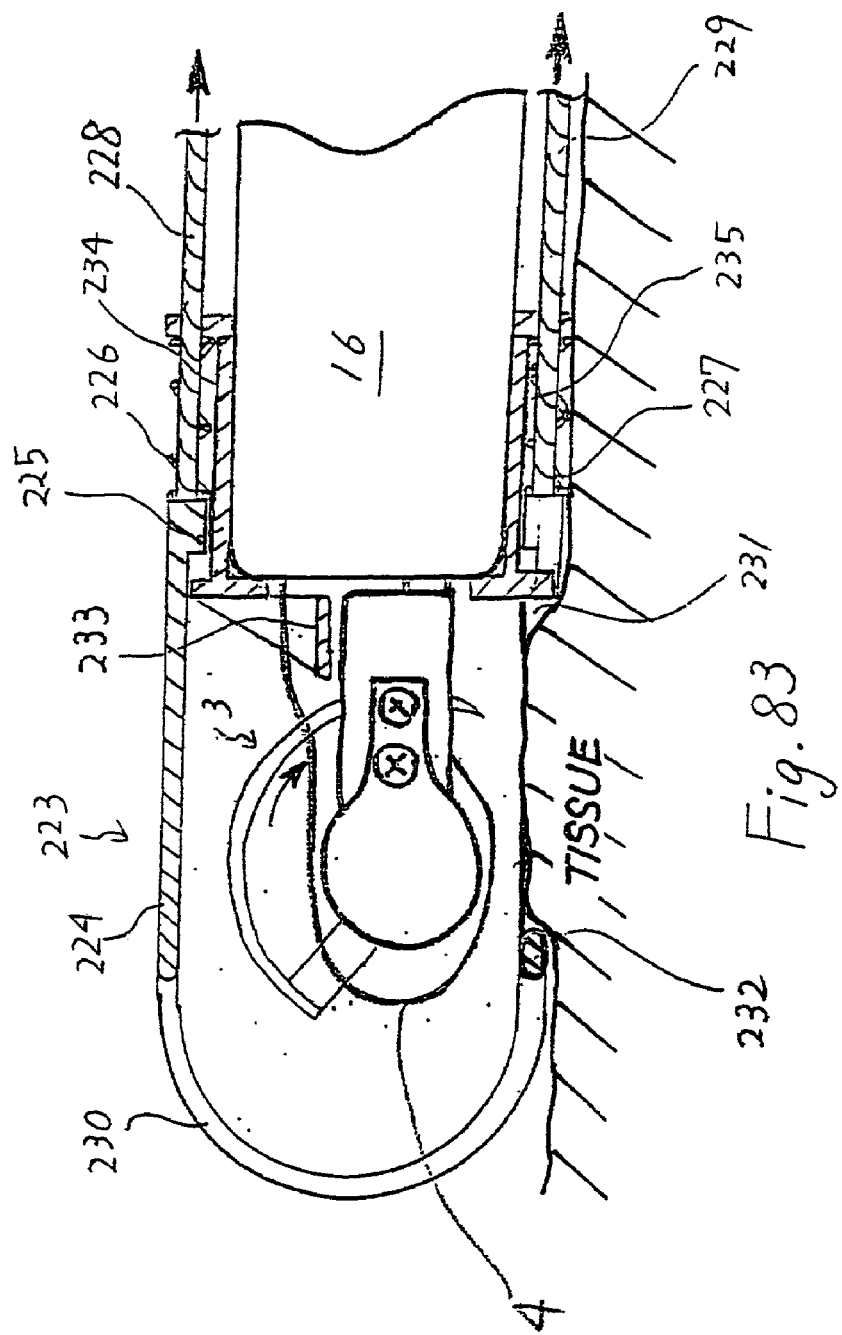
Figure 84:
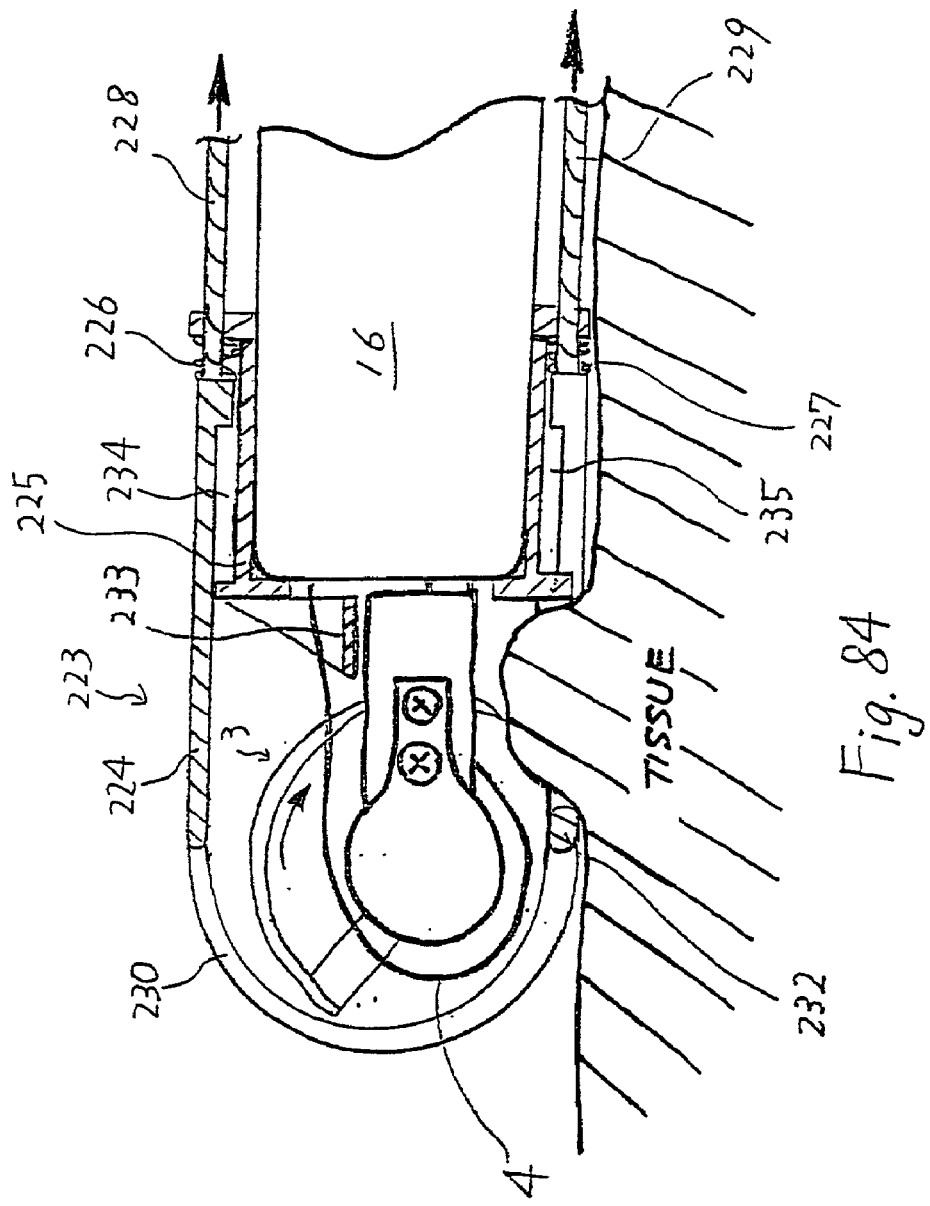
Figure 85:
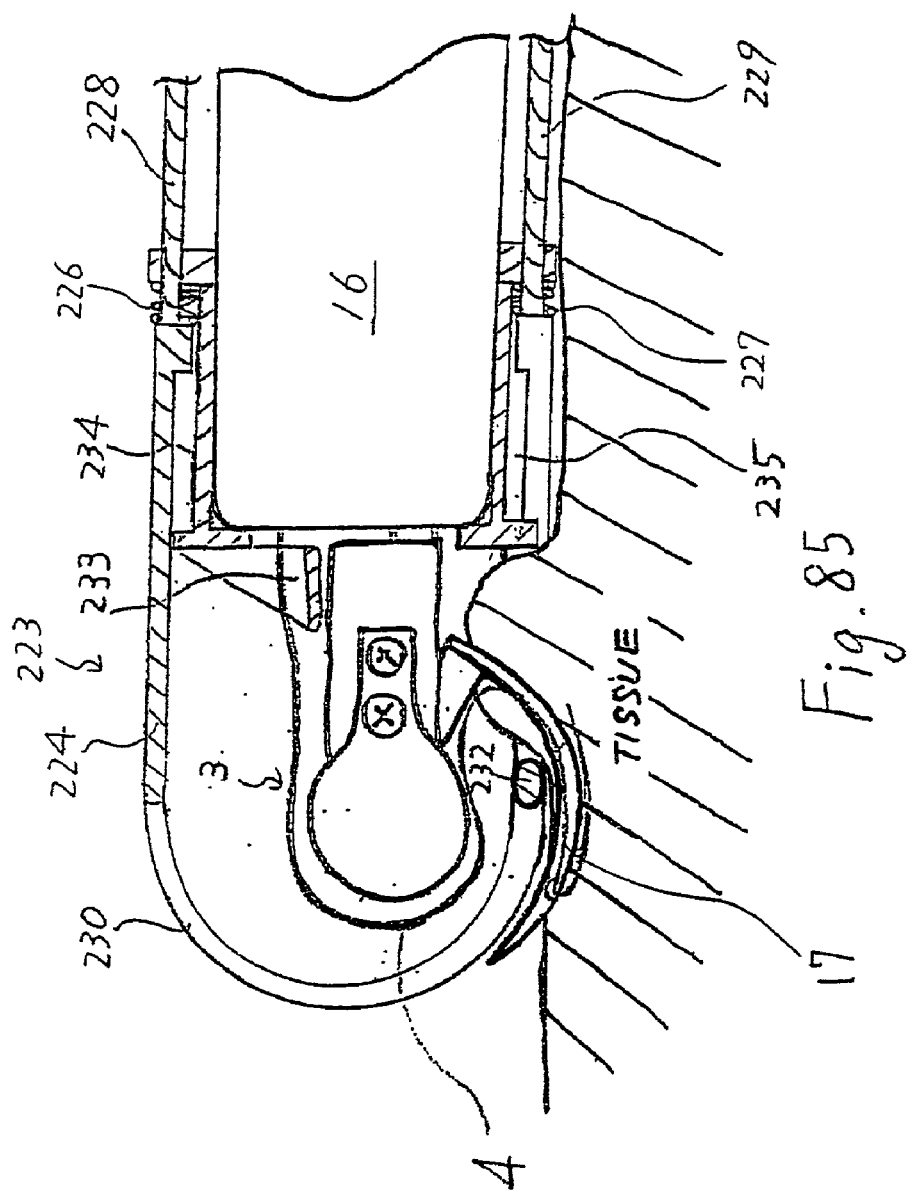
Figure 86:
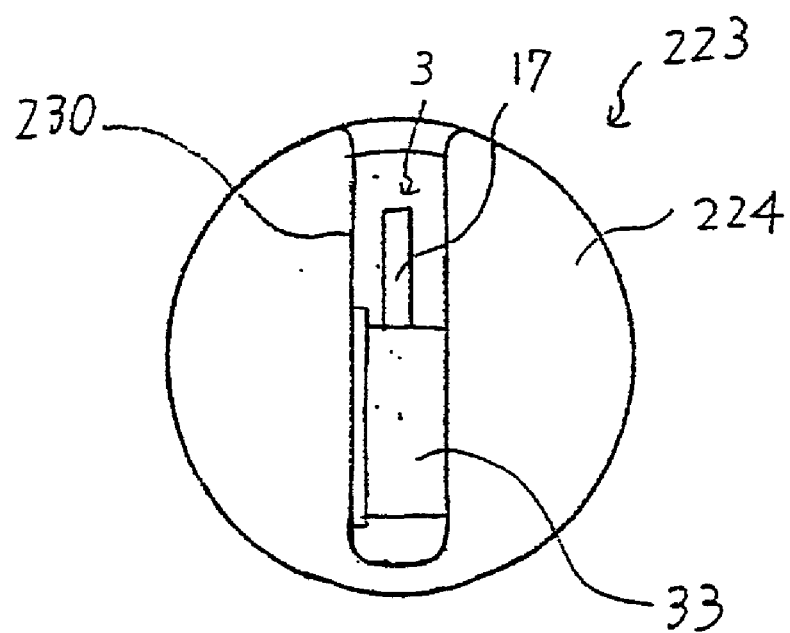
Figure 87:
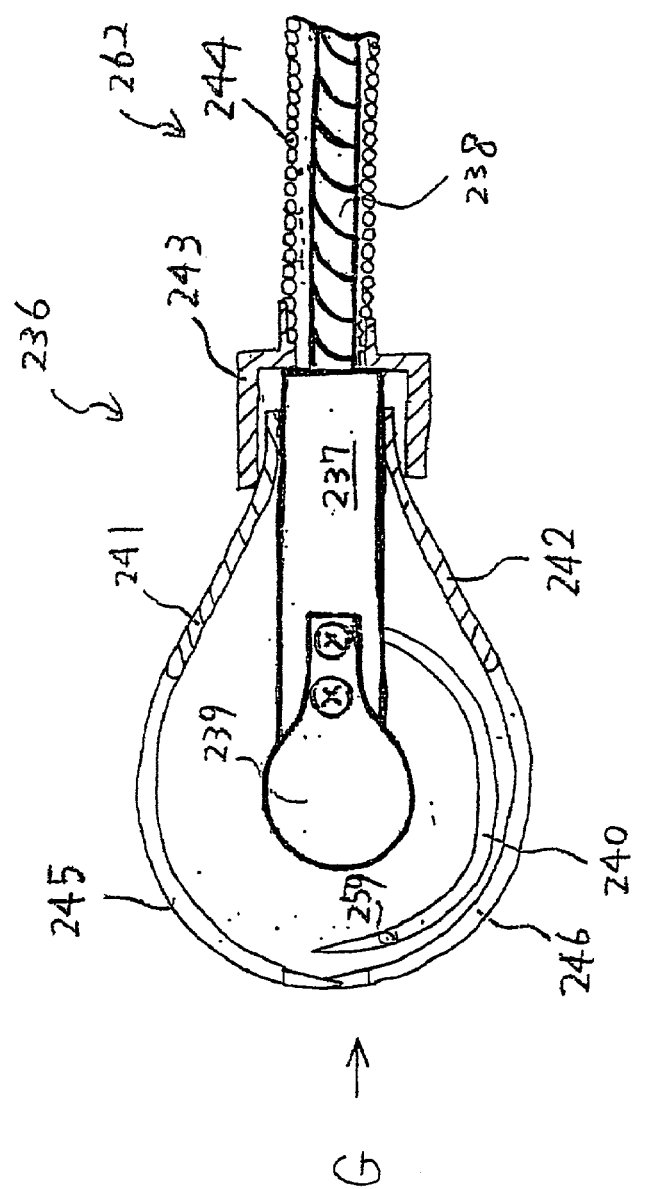
FIGS. 87 through 91 illustrate a fourteenth embodiment of the present invention.
Figure 88:
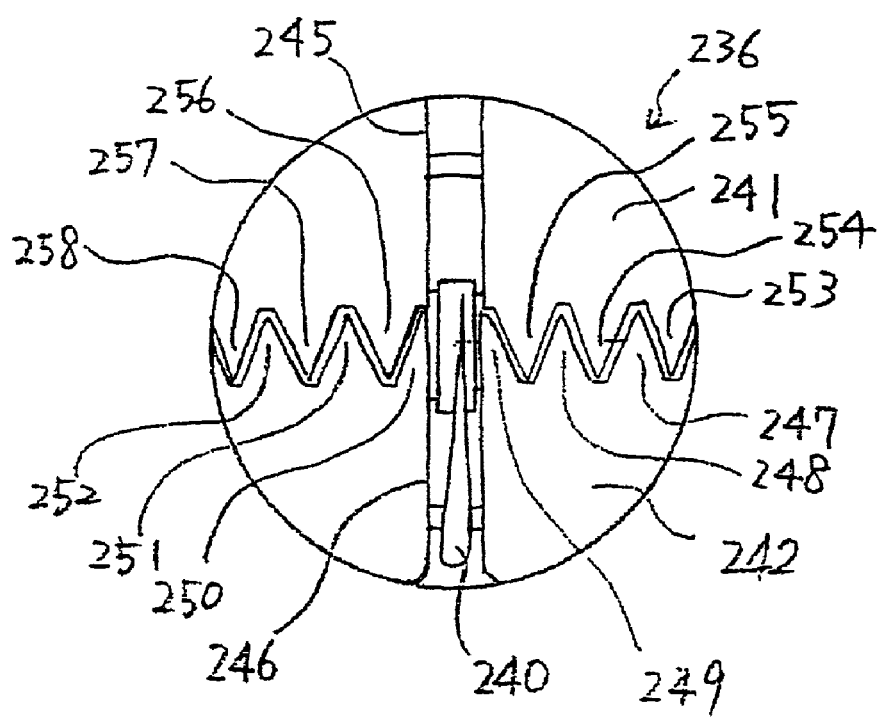

The operation of the thirteenth embodiment is described below by referring to FIGS. 83 through 85. When the distal end of the flexible portion 16 assembled as shown in FIG. 83 is pressed against the suturing site, tissue enters the slit 231. Then as shown in FIG. 84, the operating wires 228 and 229 are pulled toward the operator side using the operation unit not shown in the figure to fix the tissue with the presser portion 232 and the fixing member 225. The handle 50 shown in FIG. 19 is rotated in normal direction to rotate the curved needle 17 to urge the curved needle 17 into the tissue as shown in FIG. 85.

The grasping and withdrawing procedure of thread 4 after the puncture and the suturing procedure thereafter are same as in the first embodiment and is not reexplained. When no force is applied to the operating wires 228 and 229 by the action of the springs 226 and 227, the movable portion 224 may automatically return toward the distal end. Although the suture is made in the tangential direction against the sutured tissue in this embodiment, suturing of the forward direction or Area A in FIG. 2 may be also possible.

In addition to the advantages of the first embodiment, collapse of the tissue may be lessened when the suturing device is fixed against the tissue since no fixing needle is used as in the first embodiment. Since the tissue is pinched and the suturing site bulges as shown in FIG. 85, a deeper suture is made possible.

Embodiment 14

FIGS. 87 through 91 are directed to a fourteenth embodiment. As shown in FIGS. 87, 88, 1, and 2, in this embodiment, the tissue protective member 5 is removed from the first embodiment and the suturing device 3 is replaced by the suturing device 236 to pass through the instrument channel port 6. The suturing device 236 is fixed on the operator side of a supporting member 237, and comprises a pair of tissue grasping members 245 and 246 having at least their operator side formed of elastic member, a flexible coil 238 with its distal end fixed to the supporting member 237 and having an operating wire for rotating a curved needle 240 in the inner port, the operating wire being adopted in the similar manner to the first embodiment, a second flexible coil 244 capable of covering the majority of the flexible coil 238, and a pusher 262 comprising an opening/closing member 243 fixed at the distal end of the second flexible coil 244. An operation unit not shown in the figure is provided on the operator side of the pusher 262 to advance or withdraw the pusher 262. Teeth 247 through 252 and 253 through 258 are respectively formed on the distal ends of 241 and 242, and slits 245 and 246 are also provided to allow the curved needle to pass through. The slits 245 and 246 are at least partially transparent to ensure the field of view during puncture by the curved needle 240.

The curved needle 240 may be rotated in the same mechanism as in the first embodiment, and the description is herein omitted. A hole 259 is formed at the distal end of the curved needle 240 for the passage of the thread 4.

The operation of the fourteenth embodiment is described below by referring to FIGS. 89 through 91.

Figure 89:
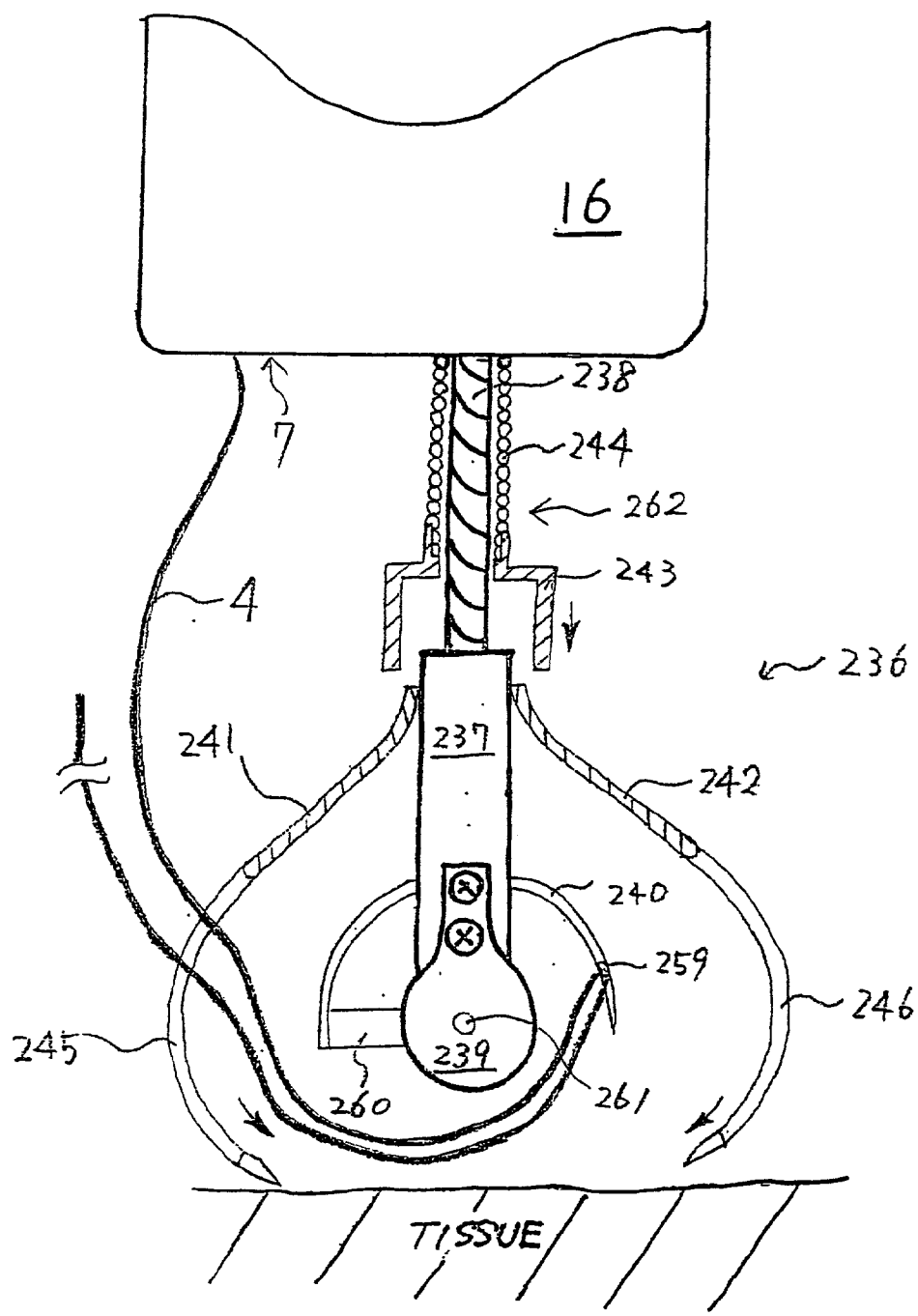

The distal end of the flexible portion 16 assembled as shown in FIG. 89 is pressed against the suturing site. At this stage, the pusher 262 is pulled toward the operator side, and 2441 and 242 are left to open. The thread 4 passes through the hole 259, the tissue grasping member 245 and the instrument channel port 7 to come out of the operator side of the instrument channel port 7.

Figure 90:
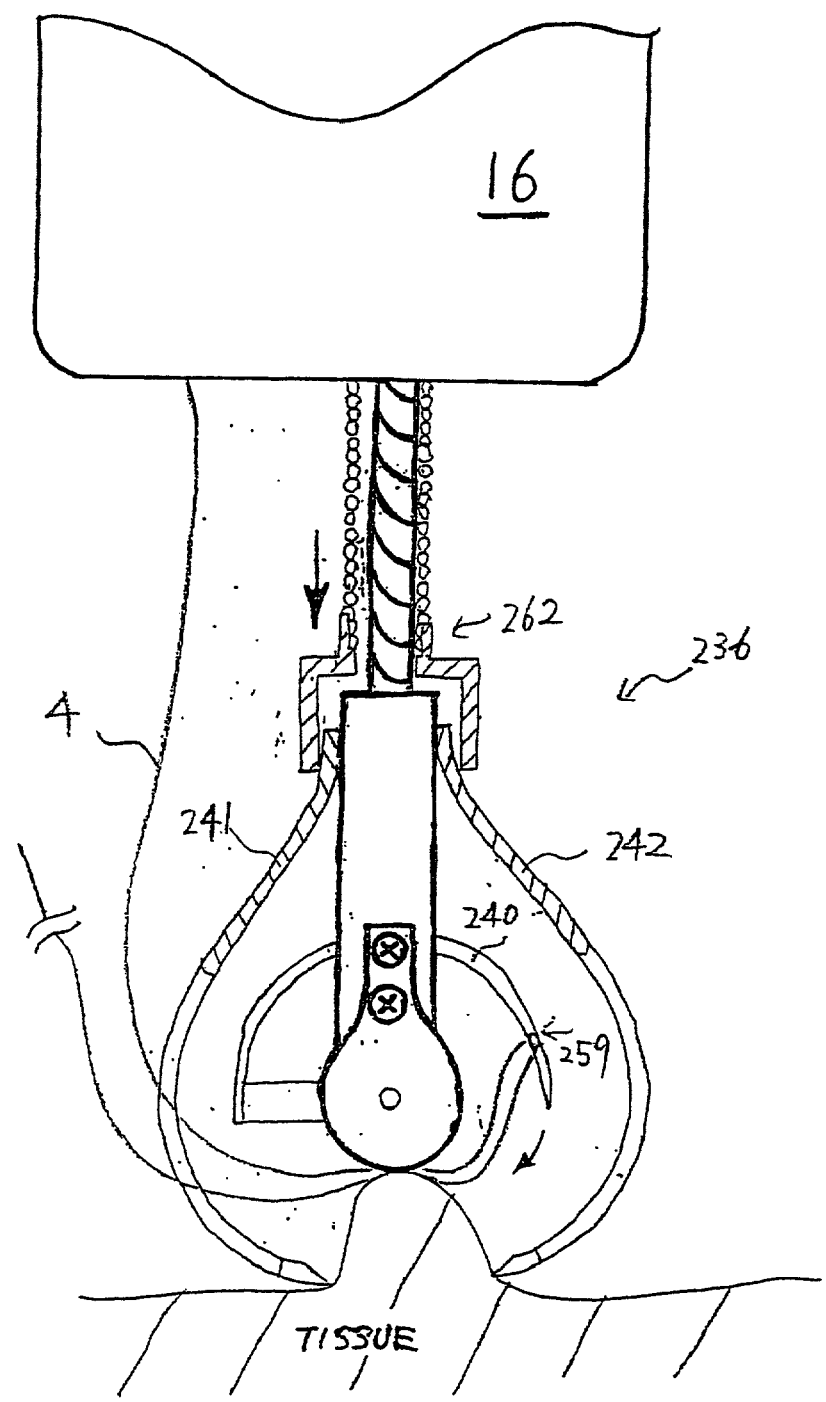

As shown in FIG. 90, the pusher is then slid toward the distal end by manipulating the operation unit not shown in the figure to close 241 and 242 and grasp the tissue at the suturing site.

Figure 91:
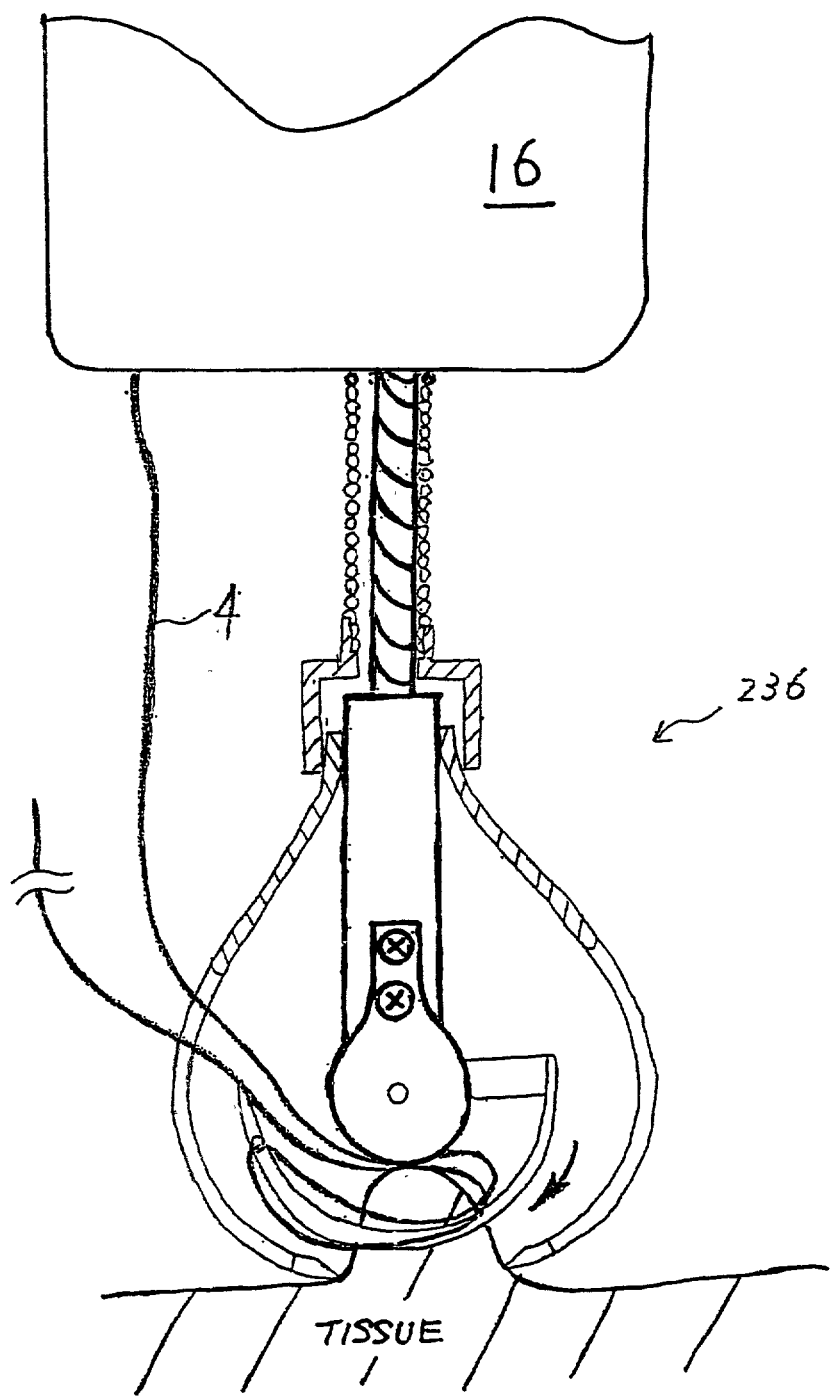

The handle shown in FIG. 19 is rotated in normal direction to rotate the curved needle 17 to urge the curved needle 17 into the tissue as shown in FIG. 91.

The grasping and withdrawing procedure of thread 4 after the puncture and the suturing procedure thereafter are performed by using the thread grasping/withdrawing means similar to that in the first embodiment and will not be again described.

In addition to the advantages of the first embodiment, collapse of the tissue may be lessened when the suturing device is fixed against the tissue since no fixing needle is used as in the first embodiment. Since the tissue is pinched and the suturing site bulges as shown in FIGS. 90 and 91, a deeper suture is made possible.

Embodiment 15

Figure 92:
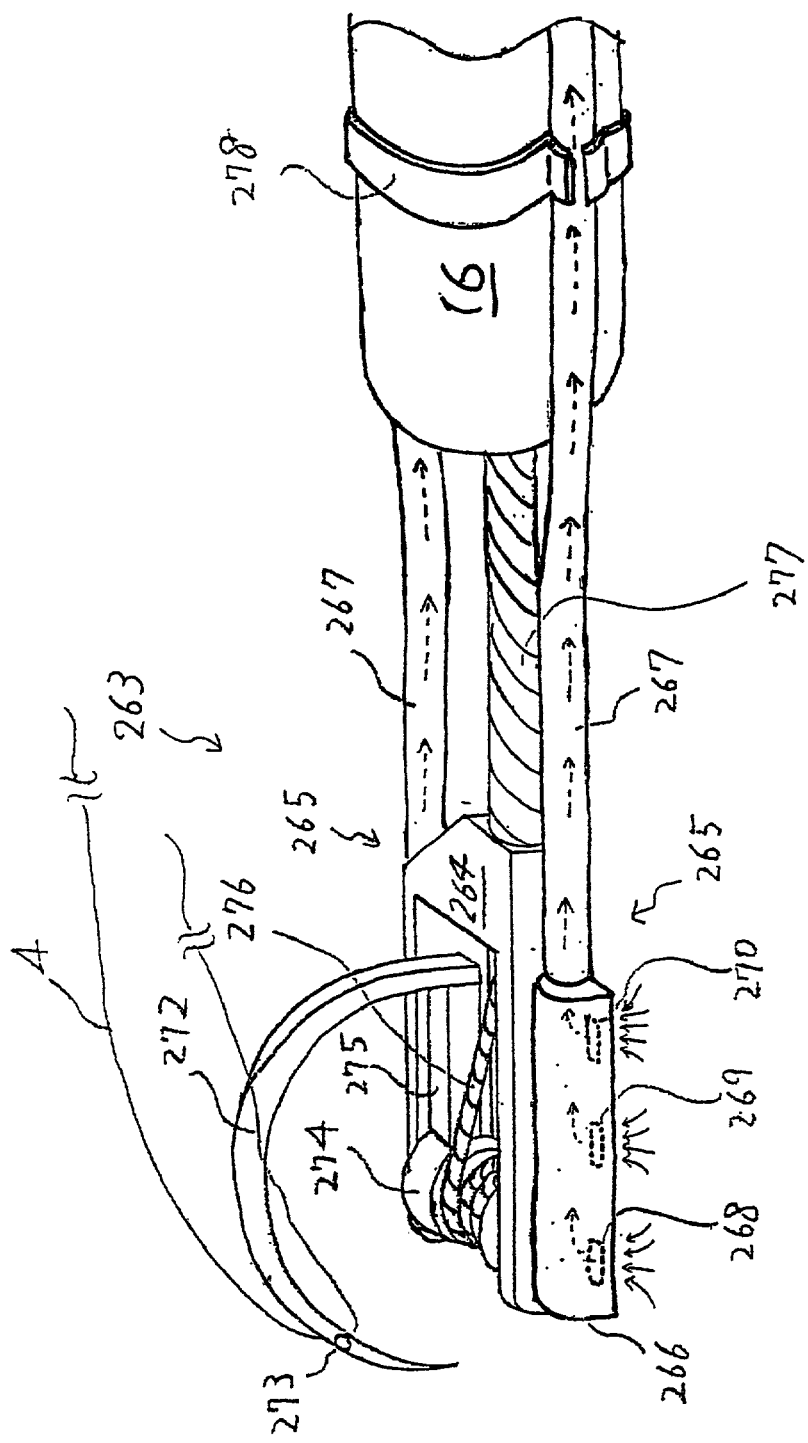
FIG. 92 illustrates a fifteenth embodiment of the present invention.

As shown in FIG. 92, in the fifteenth embodiment, the tissue protective member 5 is removed from the first embodiment and the suturing device 3 is replaced by the suturing device 263 to pass through the instrument channel port 6. The suturing device 263 is almost the same as the suturing device 3 in the first embodiment except that:

(1) no tissue fixing member 25 is provided, and
(2) a pair of suction fixing members 265 are fixed on a supporting member 264.

The suction fixing members 265 comprise a suction member 266 having openings 268, 269, and 270 and an internal cavity in communication with the openings, and a tube being in communication with the operator side of the suction member 266 and having an internal cavity from the distal end to the operator side. The operator side of the tube 267 is connected to a suction unit not shown in the figure. The tube 267 is slidably fixed to the flexible portion 16 with at least a point by a guide member 278.

The curved needle 272 may be rotated in the same mechanism as in the first embodiment, and the description is herein omitted. A hole 273 is formed at the distal end of the curved needle 272 for the passage of the thread 4.

The operation of the fifteenth embodiment is described below by referring to FIG. 92. The distal end of the flexible portion 16 assembled as shown in FIG. 92 is pressed against the suturing site, and tissue is sucked in from the openings 268 through 270 and via the tube 267 by operating the suction unit disposed on the operator side to fix the suturing device 263 against the tissue.

The grasping and withdrawing procedure of thread 4 after the puncture and the suturing procedure thereafter are performed by using the thread grasping/withdrawing means similar to that in the first embodiment and herein omitted.

In addition to the advantages of the first embodiment, collapse of the tissue may be lessened by using suction to fix the tissue.

Embodiment 16

Figure 93:
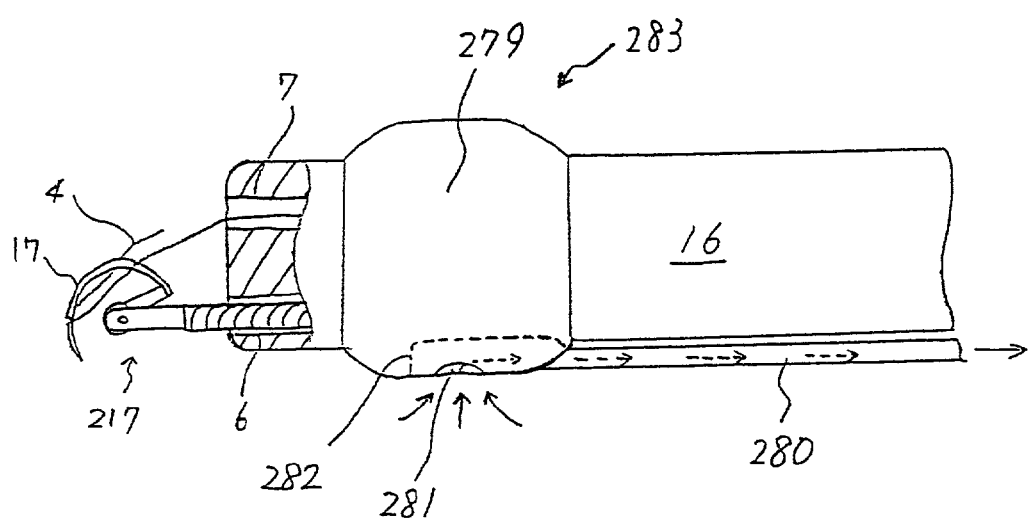
FIG. 93 illustrates a sixteenth embodiment of the present invention.

As shown in FIG. 93, a scope fixing member 283 is disposed in the vicinity of the distal end of the flexible portion 16 in a sixteenth embodiment The scope fixing member 283 comprises a fixing member 279 having at least an opening 281 and a flexible tube 280 being in communication with an internal cavity 282 which is in turn in communication with the opening 281, and the operator side of the flexible tube 280 is connected to a suction unit not shown in the figure. The shape of the opening 281 may be circular, oval, or polygonal.

The flexible portion 16 has the same construction as the first embodiment, and the suturing device 3 of the first embodiment and the suturing device 217 of the eleventh embodiment may be inserted to the instrument channel port 6 shown in FIG. 2. As in FIG. 2, the thread grasping/withdrawing means 69 and the thread 4 are disposed in the instrument channel port 7, and the tissue protective member 5 may be attached to the most distal part of the instrument channel port 6.

The operation of the sixteenth embodiment is described below by referring to FIG. 93.

As shown in FIG. 93, tissue is sucked in by the suction unit on the operator side to fix the distal end of the flexible portion 16 against the tissue. The grasping and withdrawing procedure of thread 4 after the puncture and the suturing procedure thereafter are performed by using the thread grasping/withdrawing means similar to that in the first embodiment and not again explained.

In addition to the advantages of the first embodiment, collapse of the tissue may be lessened by using suction to fix the tissue.

Embodiment 17

Figure 94:
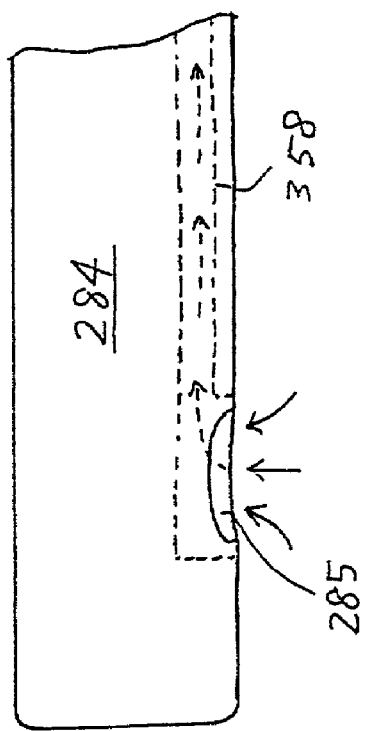
FIG. 94 illustrates a seventeenth embodiment of the present invention.

As shown in FIG. 94, the seventeenth embodiment is obtained by replacing the flexible portion 16 of the sixteenth embodiment by a flexible portion 284. The flexible portion 284 has the function of the scope fixing member 283 of the sixteenth embodiment therein. Therefore, the flexible portion 284 comprises an opening 285 at its distal end and an internal cavity 358 being in communication with the opening 285, and the operator side of the internal cavity 358 is connected to a suction unit not shown in the figure as in the sixteenth embodiment As in the sixteenth embodiment, the flexible portion 284 has the same construction as the first embodiment, and the suturing device 3 of the first embodiment and the suturing device 217 of the eleventh embodiment may be inserted to the instrument channel port 6 shown in FIG. 2. As in FIG. 2, the thread grasping/withdrawing means 69 and the thread 4 are disposed in the instrument channel port 7, and the tissue protective member 5 may be attached to the most distal part of the instrument channel port 6. The shape of the opening 285 may be circular, oval, or polygonal.

The operation of the seventeenth embodiment is described below by referring to FIG. 94 As shown in FIG. 94, tissue is sucked into the opening 285 by the suction unit on the operator side to fix the distal end of the flexible portion 16 against the tissue. The grasping and withdrawing procedure of thread 4 after the puncture and the suturing procedure thereafter are performed by using the thread grasping/ withdrawing means similar to that in the first embodiment and not repeated.

In addition to the advantages of the first embodiment, collapse of the tissue may be lessened by using suction to fix the tissue.

Embodiment 18

Figure 95:
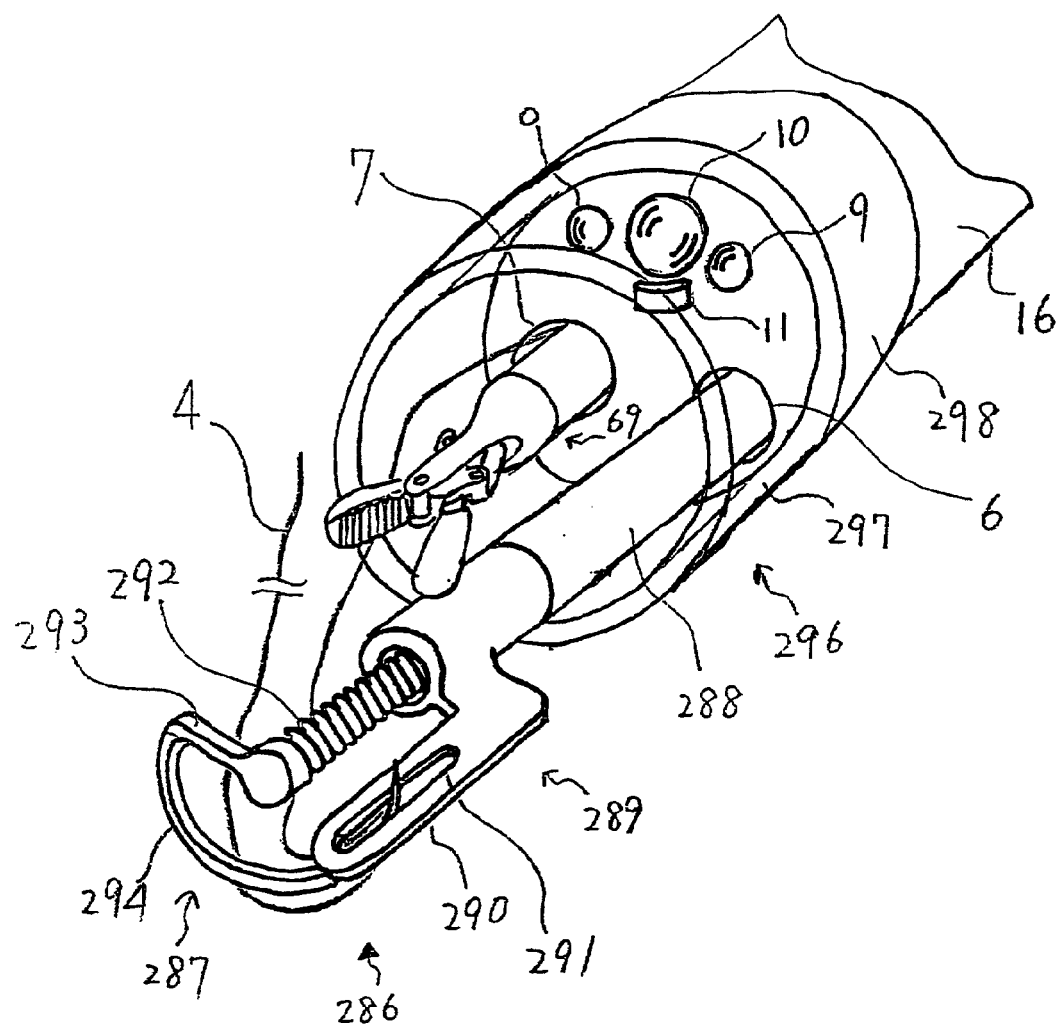
FIGS. 95 through 98 illustrate an eighteenth embodiment of the present invention.

An eighteenth embodiment is shown in FIGS. 95 through 98. As shown in FIG. 95, a suturing device 286 shown as the eighteenth embodiment is rotatably disposed in the instrument channel port 6 of the endoscope with at least a part of the flexible portion 16 of the first embodiment covered with a transparent cap 296.

The suturing device 286, at least partially formed of flexible material, comprises a sheath 288 having an internal cavity, a tissue fixing member 289 disposed at the distal end of the sheath 288 and having an internal cavity in communication with the internal cavity, a coil 292 rotatably inserted into the internal cavity and made from multicoil of superior torque transmission, an arm 293 for connecting and fixing the coil 292 with a curved needle 294, and an operation unit provided on the operator side of the coil 292 and not shown in the figure. On the tissue fixing member 289, an axially extending arm 290 and a slit 291 having a width allowing the passage of the curved needle 294 are formed. The tissue fixing member 289 may have a U-shaped slit as a tissue fixing member 299 shown in FIG. 98.

In the suturing device 286 of the foregoing construction, the curved needle 294 may be rotated via the coil 292 by rotating the operation unit on the operator side and not shown in the figure. The coil 292 may move back and forth in the sheath 288 so as to move the curved needle 294 to any given position in the slit 291. The thread grasping/withdrawing means 69 and the thread 4 are also disposed in the instrument channel port 7 as in the first embodiment.

Figure 97:
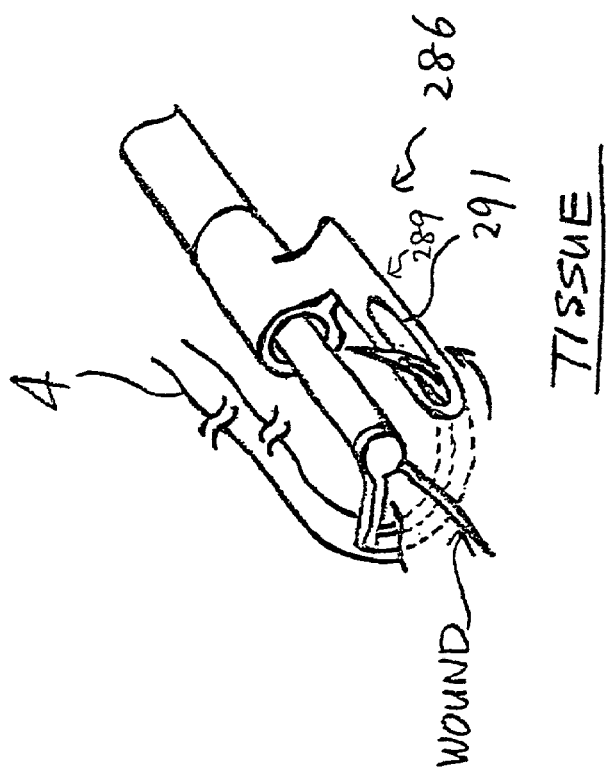

The operation of the eighteenth embodiment is described below by referring to FIGS. 95 through 97.

Insert the flexible portion 16 to the suturing site with the suturing device 286 set as shown in FIG. 95 and housed in the transparent cap 296.

Figure 96:
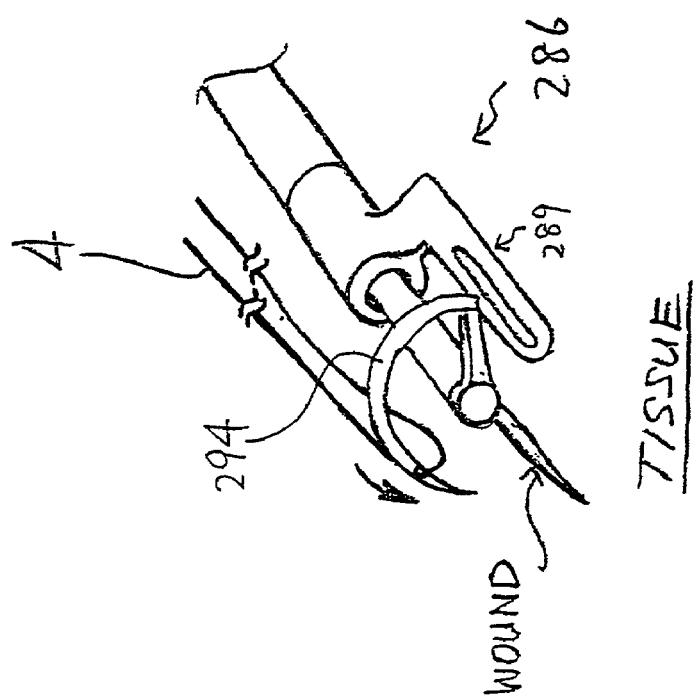
Figure 98:
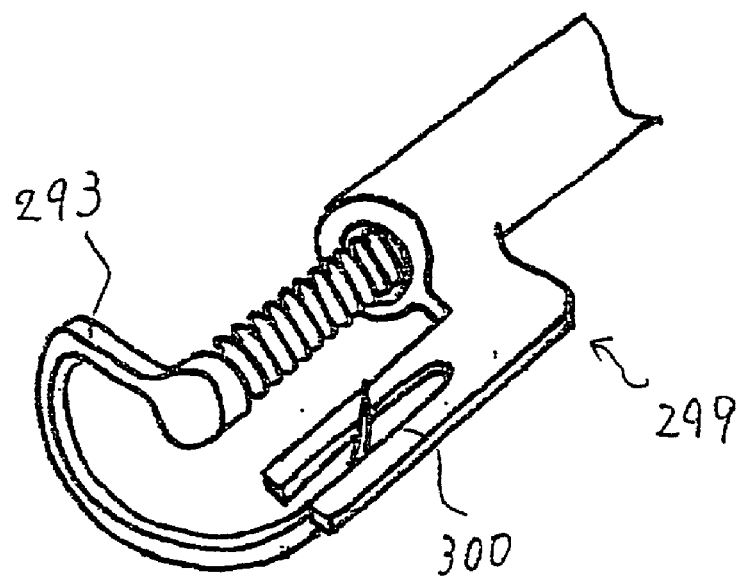

After the distal end of the flexible portion 16 reaches the suturing site, push the operation unit provided on the operator side of the suturing device 286 to push the suturing device 286 out of the transparent cap 296, and rotate the curved needle 294 to the position shown in FIG. 96 by using the operation unit on the operator side.

Adjust the angle of the endoscope to press the suturing device 286 against the suturing site, and rotate the operation unit of the suturing device 286 to urge the curved needle 294 into the suturing site. The position of the slit 291 shall be adjusted in advance so that the rotational trajectory of the curved needle 294 enters the slit 291. Securely fix the tissue fixing member 289 on the operator side to prevent the tissue fixing member 289 from rotating along with the passage of the curved needle 294 in the slit 291.

The grasping and withdrawing procedure of thread 4 after the puncture and the suturing procedure thereafter are performed by using the thread grasping/withdrawing means similar to that in the first embodiment and not repeated.

The coil with superior torque transmission may efficiently transmits the puncture force to the curved needle even in any winding state of the endoscope, thus enhancing the puncture force and attaining deeper puncture of the curved needle into the tissue.

Since the rotation axis of the curved needle is parallel to the scope's axis, the point where the curved needle enters the tissue and the point where the curved needle comes out of the tissue may always be checked, and clear field of view may be ensured during suturing.

Since the operation unit disposed on the operator side of the coil 292 may be rotated both in normal and reverse directions, puncture position may be repeatedly corrected.

The grasping/withdrawing means for easily and reliably catching the thread 4 and withdrawing to the operator side contribute to reduction in treatment time. In addition, the tissue fixing member 289 for preventing the tissue from extending during puncture enables the pointed end of the curved needle to come out of the tissue easily, thus reducing the treatment time and attaining deeper puncture of the curved needle for safe and reliable suturing. Furthermore, use of the instrument channel ports of the endoscope enables easy suturing even in a narrow body cavity. Also, general-purpose endoscopes may be utilized for treatment to reduce the cost.

In addition, since the suturing device is independent in structure, washing, disinfection, and sterilization may be possible as in conventional instruments.

Embodiment 19

Figure 99:
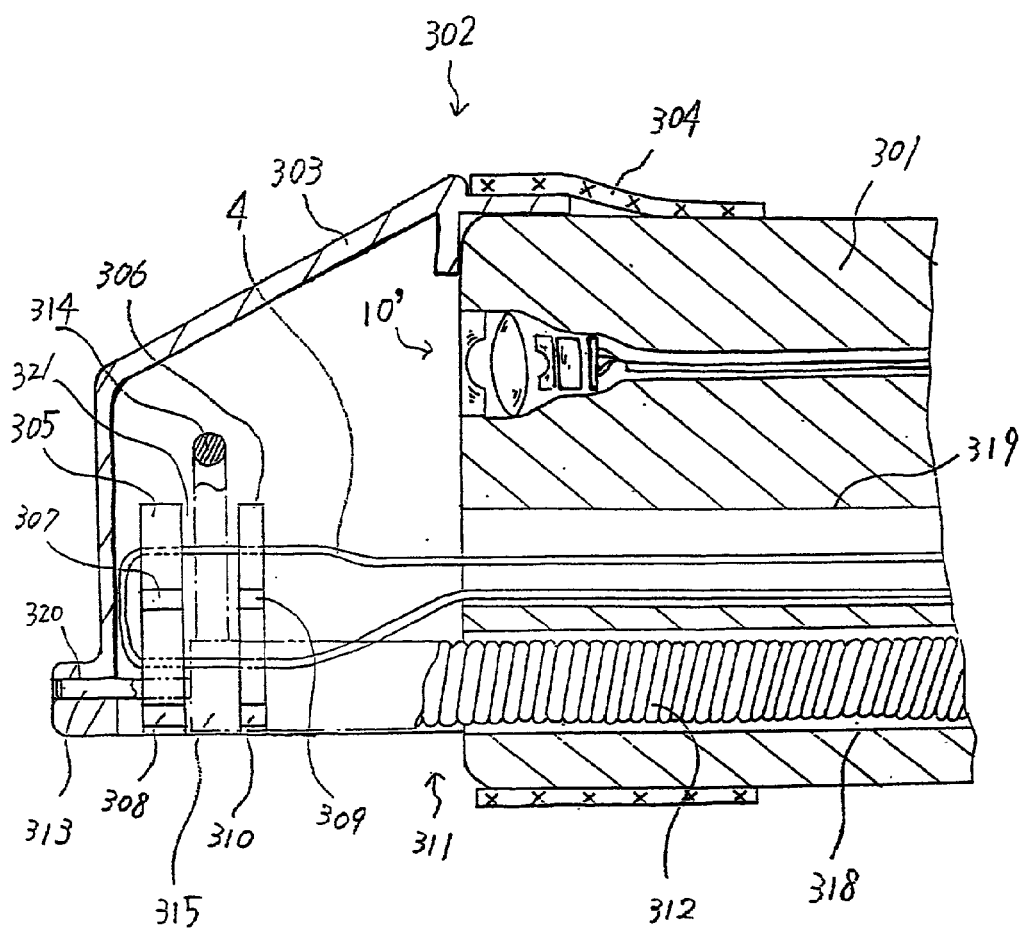
FIGS. 99 through 102 illustrate an nineteenth embodiment of the present invention.
Figure 100:
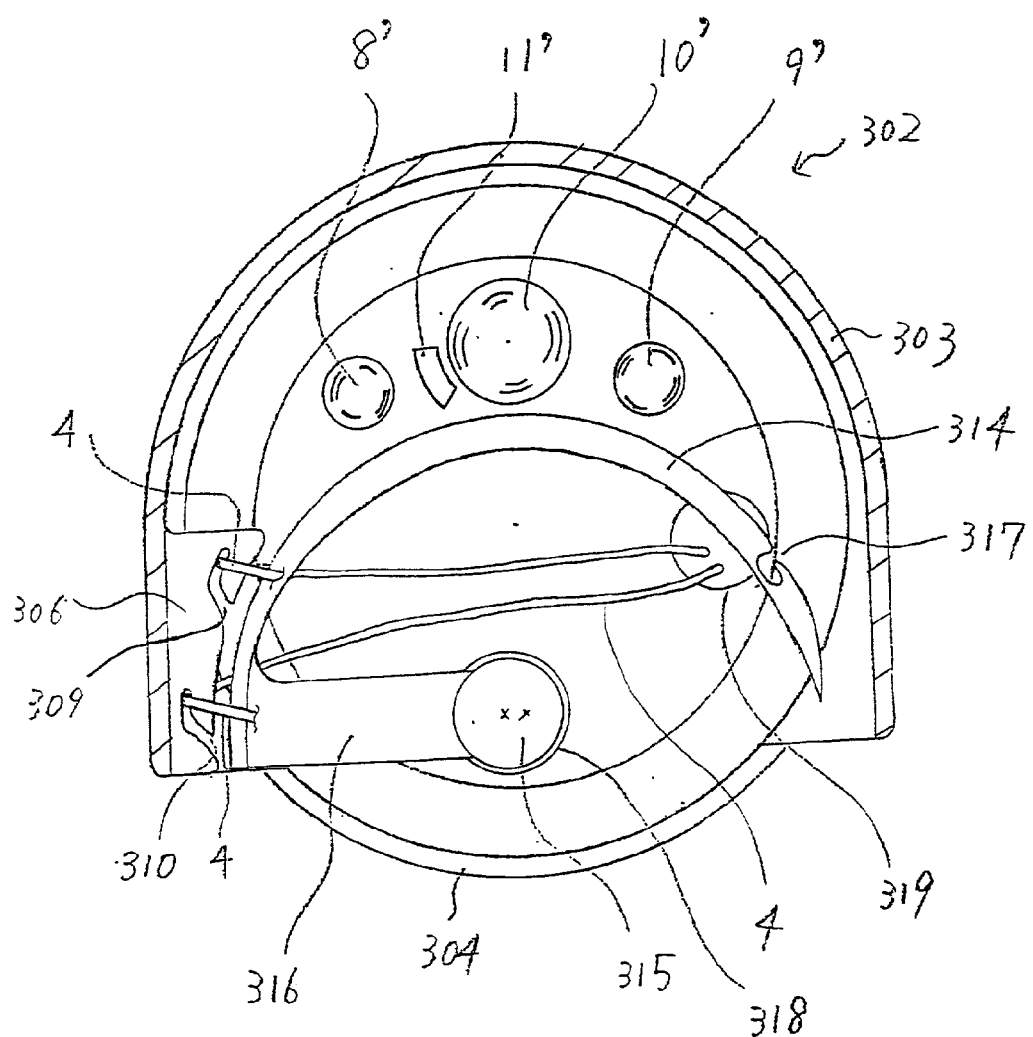

A nineteenth embodiment is illustrated in FIGS. 99 through 102. As shown in FIGS. 99 and 100, in this embodiment, a tissue protective member 302 is detachably mounted on the distal end of a flexible portion 301, on which a CCD camera 10', light guides 8' and 9', instrument channel ports 318 and 319, and a nozzle 11' for washing the lens of the CCD camera. The tissue protective member 302 comprises a at least partially transparent protective member 303 and a fixing member 304 and is fixed by pressing the fixing member 304 into the distal end of the flexible portion 301. The protective member 303 is partially made from a transparent member to ensure clear field of endoscopic view, and suture holders 305 and 306 are formed thereon respectively having the slits 307 and 308 and the slits 309 and 310 for holding the thread 4. A suturing device 311 comprises a coil 312 made from multiple-thread coil or the like, which can rotate in the instrument channel and has superior torque transmission, a tip 315 fixed at the distal end of the coil 312, an arm for connecting the tip 315 and the curved needle 314, and an operation unit provided on the operator side of the coil 312 and not shown in the figure. A needle's slit 317 having the same structure as the needle's slit 18 of the first embodiment is provided on the curved needle 314. A groove 41 shown in FIG. 8 of the first embodiment may be formed on the needle's slit 317. An axis 313 formed coaxially with the coil 312 and fixed on the tip 315 is rotatably fitted with the hole 320 formed on the protective member 303. Therefore, the suturing device 311 may rotate on the axes of the axis 313 and the instrument channel port 318, and the curved needle 314 may pass through a slit 321 formed between the suture holder 305 and the fixing member 304. At this stage, since the thread 4 detachably held by the suture holder 305 and the fixing member 304 is disposed on the rotational trajectory of the curved needle 314, the thread 4 may be hooked in the needle's slit 317 formed on the curved needle 314. Since the width of the needle's slit 317 is formed at least larger than the external diameter of the thread 4, the needle's slit easily hooks the thread 4. The needle's slit may hook the thread 4 twice separately.

Although the center of curvature of the curved needle 314 is almost identical to the center of rotation in this embodiment, the centers may be intentionally deviated if it is easier to hook the thread 4.

The operation of the nineteenth embodiment is described below by referring to its FIGS. 99 through 102.

Insert the flexible portion 301 set as shown in FIGS. 99 and 100 to the suturing site in the body cavity.

With the curved needle 314 set at the position shown in FIG. 100 by angulation of the endoscope, press the flexible portion 301 against the suturing site.

Figure 101:
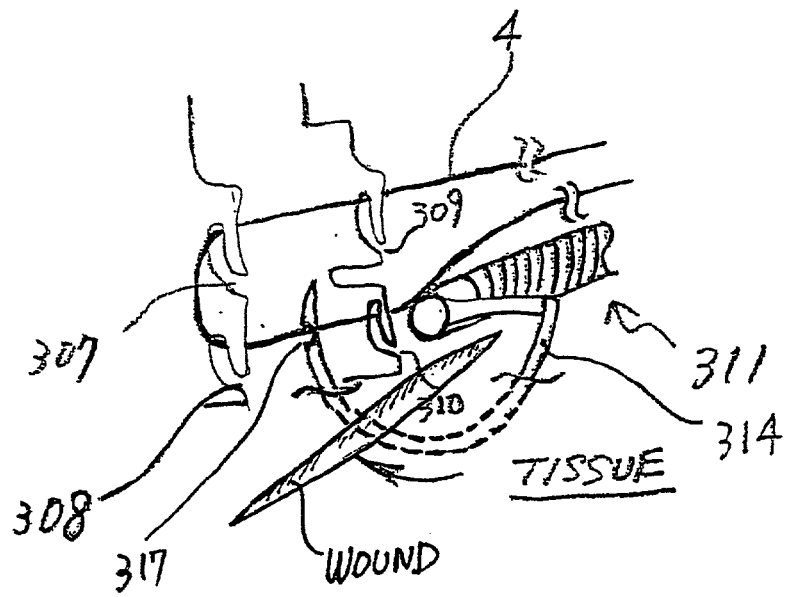
Figure 102:
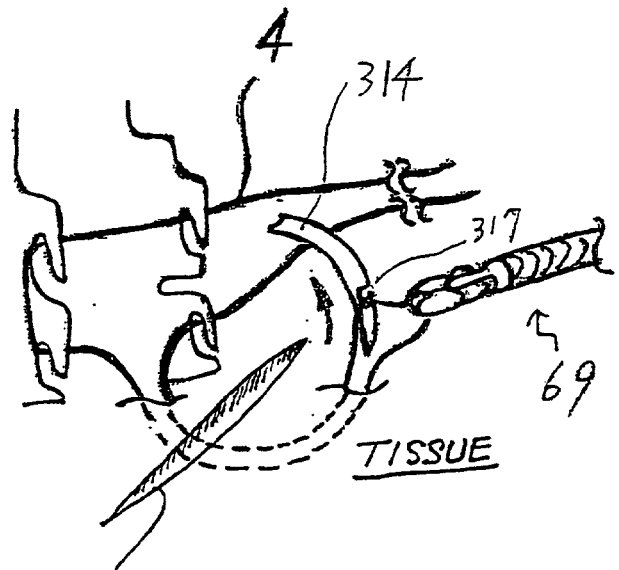

Rotate the curved needle 314 clockwise as shown in FIG. 101 by operating the operation unit on the operator side not shown in the figure to urge the curved needle 314 into the suturing site, and hook the thread held by the slits 308 and 310 into the needle's slit 317. Then rotate the curved needle 314 counterclockwise as shown in FIG. 102 to let the thread 4 come out of the tissue, pull out the thread to the operator side by using the thread grasping/withdrawing means inserted via the instrument channel 319, and adjust the angle of the endoscope to remove the thread from the slits 308 and 310 to complete the first stitch.

Similarly press the flexible portion 301 against the tissue slightly away from the first stitch, and repeat the steps (3) and (4). At this stage, the thread to be hooked to the needle's slit 317 is the portion held by the slits 307 and 309.

As in FIG. 45 of the first embodiment, make a knot on the thread 4 on the operator side, and push the knot by the knot pusher 125 inserted in the instrument channel 319 to complete the suturing procedure. If the knot is insufficient, repeat the step (6) for several times.

In addition to the advantages of the eighteenth embodiment, the thread does not accompany the curved needle at the first puncture, thus reducing resistance by the thread during puncture and enhancing the puncture capability.

Embodiment 20

The twentieth embodiment is illustrated in FIGS. 99, 103 through 107 and 112. This embodiment is an improved version of the nineteenth embodiment. The twentieth embodiment has the same construction as nineteenth embodiment, except that the suturing device 311 of nineteenth embodiment is replaced by a suturing device 322 and that the width of the slit 321 of nineteenth embodiment is increased.

Figure 112:
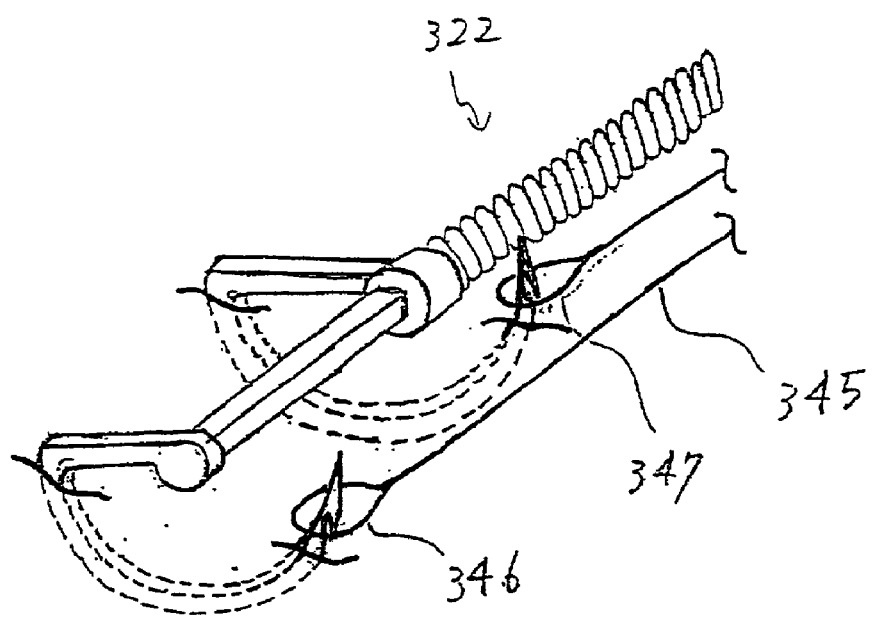

The suturing device 322 comprises a coil 323 which may be rotate in the instrument channel port 318 and is made from multiple-thread coil of superior torque transmission, a tip A 329 fixed at the distal end of the coil 312 and having an internal cavity with rectangular cross section, an arm 331 for connecting the tip A 329 and the curved needle 326, an operation unit (1) provided on the operator side of the coil 323 and not shown in the figure, a shaft 324 which is connected at its operator side to the operation unit (2) not shown in the figure, at least partially has a rectangular cross section, a shaft 324 fitted in the rectangular internal cavity in the tip A 329, a tip B 330 fixed at the distal end of the shaft 324, and an arm 332 for connecting the tip B 330 and a curved needle 325. A shaft 333 located coaxial to the coil 323 and the shaft 324 and fixed to the tip B 330 is rotatably fitted to a hole 320 formed in the transparent member 303 shown in FIG. 99. Therefore, the suturing device 322 may rotate on the axes of the coil 323 and the shaft 324, and the curved needles 325 and 326 may pass through the slit 321 formed between the suture holder 305 and fixing member 304 and may constantly rotate in the same direction. Needle's slits 327 and 328 are provided on the curved needles 325 and 326 as in nineteenth embodiment, but the needle's slit 328 is closer to the distal end of the curved needle than the needle's slit 327. The distance between the curved needles 325 and 326 may be freely adjusted by moving the shaft 324. The method to hook the thread with the needle's slits 327 and 328 is same as in nineteenth embodiment. Since the twentieth embodiment has a structure in which the direction of the attachment of the curved needle is horizontally opposite to that of nineteenth embodiment, FIG. 100 is viewed symmetry for the twentieth embodiment. A thread 345 having loops 346 and 347 on the both ends as shown in FIG. 112 may be used instead of the thread 4.

The operation of the twentieth embodiment is described below by referring to FIGS. 103 through 107.

Figure 103:
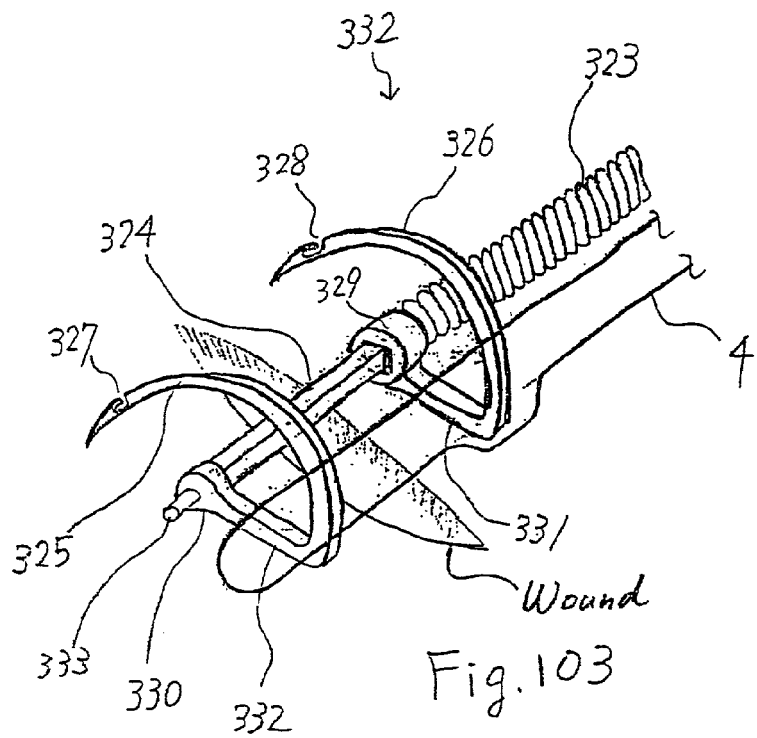
FIGS. 103 through 107 and 112 illustrate a twentieth embodiment of the present invention.

Insert the flexible portion 301 set as shown in FIG. 103 to the suturing target site in the body cavity as in the nineteenth embodiment, and press the flexible portion 301 against the tissue so that the suturing site comes between the curved needles 325 and 326.

Figure 104:
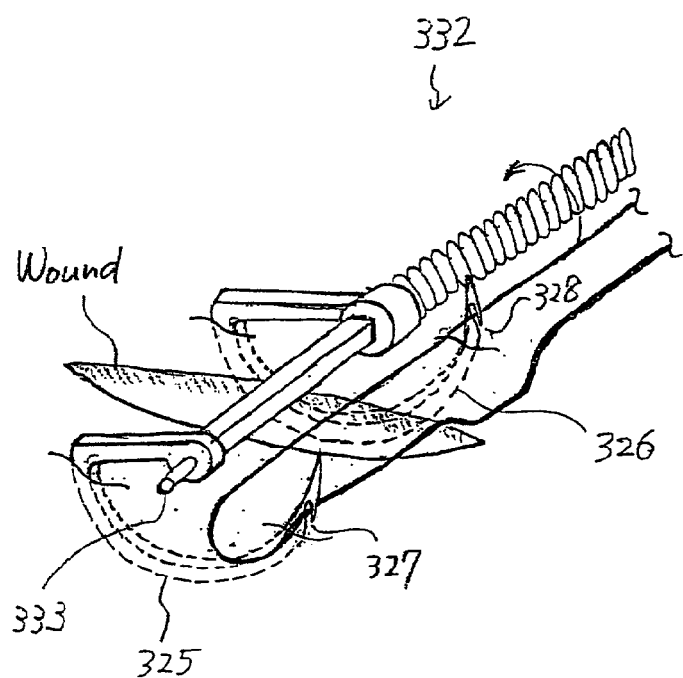

As shown in FIG. 104, rotate the curved needles 325 and 326 counterclockwise by using the operation units (1) and (2) not shown in the figure to urge both the curved needles 325 and 326 into the suturing site substantially simultaneously, and hook the thread 4 held by the slits 308 and 310 and the thread 4 held by the slits 307 and 309 to the needle's slit 327 on the curved needle 325 and the needle's slit 328 on the curved needle 326.

Figure 105:
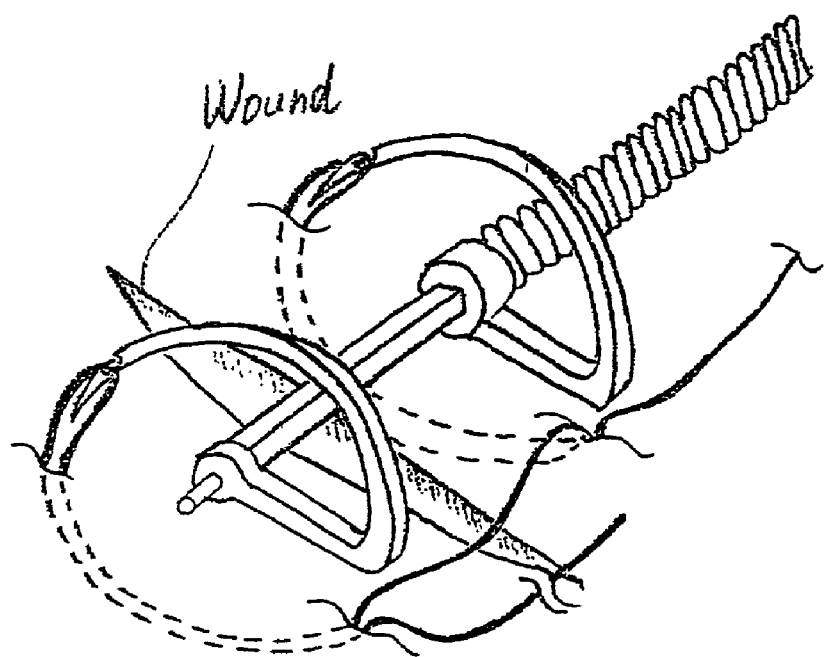
Figure 106:
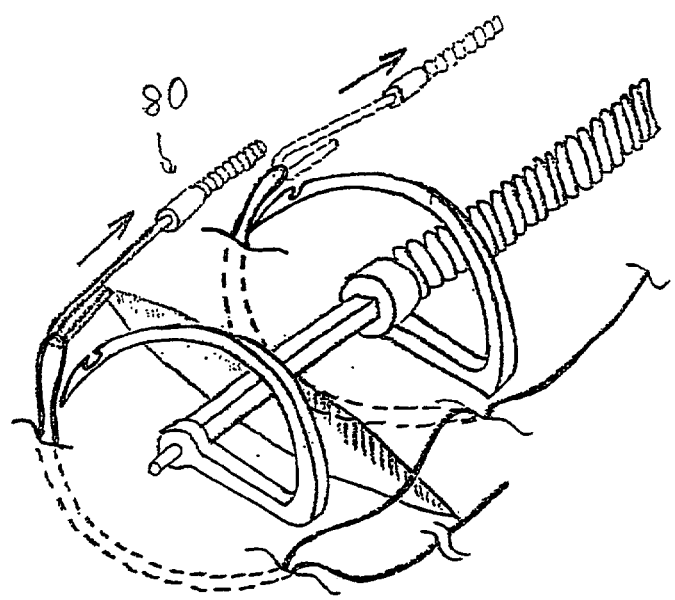

Then rotate the coil 323 and the shaft 324 clockwise as shown in FIGS. 105 and 106 to allow the threads 4 to come out of the tissue, and pull the threads 4 using the thread grasping/withdrawing means 80 inserted via the instrument channel 319.

Figure 107:
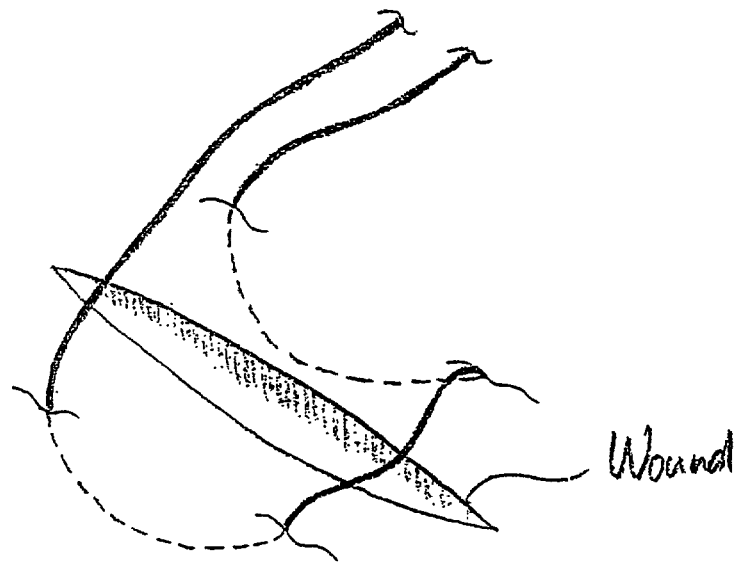

Use the thread 4 as shown in FIG. 107 to make a knot as in the nineteenth embodiment and as shown in FIG. 45 to complete the suturing procedure.

In addition to the advantages of nineteenth embodiment, suturing by puncture of two curved needles reduces treatment time. Since the distance between the two curved needles may be adjusted, the suture intervals may be adjusted as required.

Embodiment 21

FIGS. 95, and 108 through 111 illustrate a twenty-first embodiment of the invention. This embodiment is an improved version of the eighteenth embodiment shown in FIG. 95, and has construction in which the suturing device 286 of the eighteenth embodiment is replaced by a suturing device 344.

The suturing device 344 comprises a coil 335 which may be rotate in the instrument channel port 6 and is made from multiple-thread coil of superior torque transmission, a tip C 336 fixed at the distal end of the coil 335 and having an internal cavity, an arm 340 for connecting the tip C 336 and a curved needle 338, an operation unit (3) provided on the operator side of the coil 335 and not shown in the figure, a shaft 344 which is connected at its operator side to the operation unit (4) not shown in the figure, a tip D 337 fixed on the distal end of the shaft 344, and an arm 341 for connecting the tip D 337 and a curved needle 339. The distance between the curved needles 338 and 339 may be freely adjusted by moving the shaft 344. The curved needles 338 and 339 may be rotated in different directions. Needle holes 342 and 343 are respectively provided on the curved needles 338 and 339. Although the needle holes 342 and 343 are provided in this embodiment, they may be needle's slits as in the twentieth embodiment.

The operation of the twenty-first embodiment is described below by referring to FIGS. 108 through 111.

Figure 108:
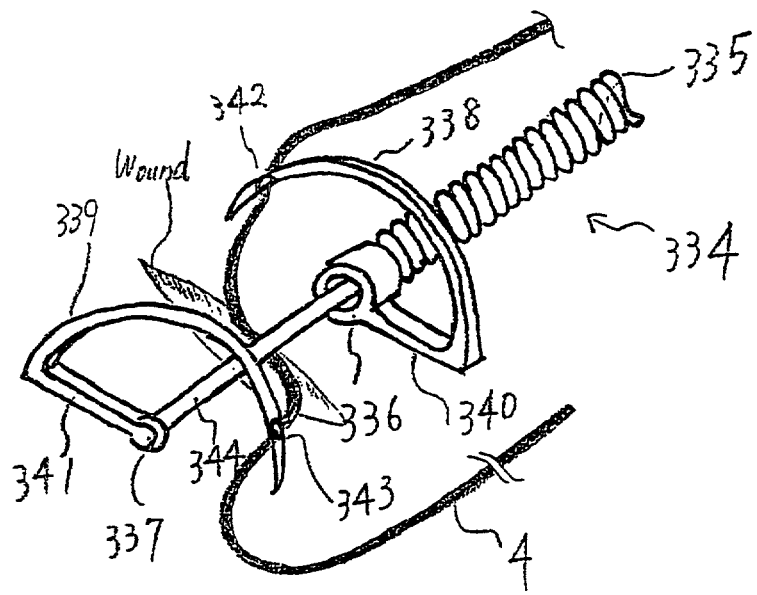

Insert the suturing device 334 set as shown in FIG. 108 into the instrument channel port 6 shown in FIG. 95 of the eighteenth embodiment, and pass the thread 4 and the thread grasping/withdrawing means 80 into the instrument channel port 7.

Insert the distal end of the flexible portion 16 with the suturing device 334 set thereon to the suturing target site in the body cavity, and press the flexible portion 16 against the tissue with the curved needles 338 and 339 set at the position shown in FIG. 108.

Figure 109:
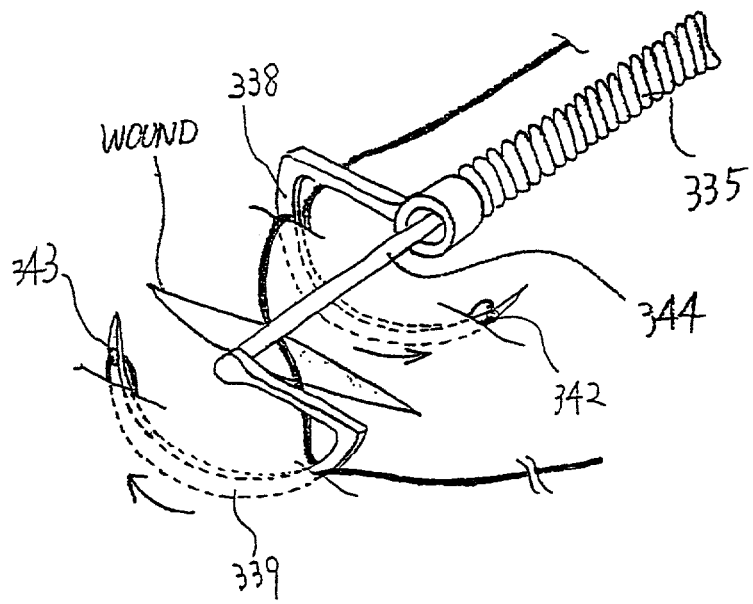

As shown in FIG. 109, respectively rotate the coil 335 and the shaft 344 counterclockwise and clockwise by using the operation units (3) and (4) not shown in the figure to urge both the curved needles 338 and 339 into the suturing site as shown in the figure. The puncture timing of the two curved needles may be either simultaneous or not simultaneous.

Figure 110:
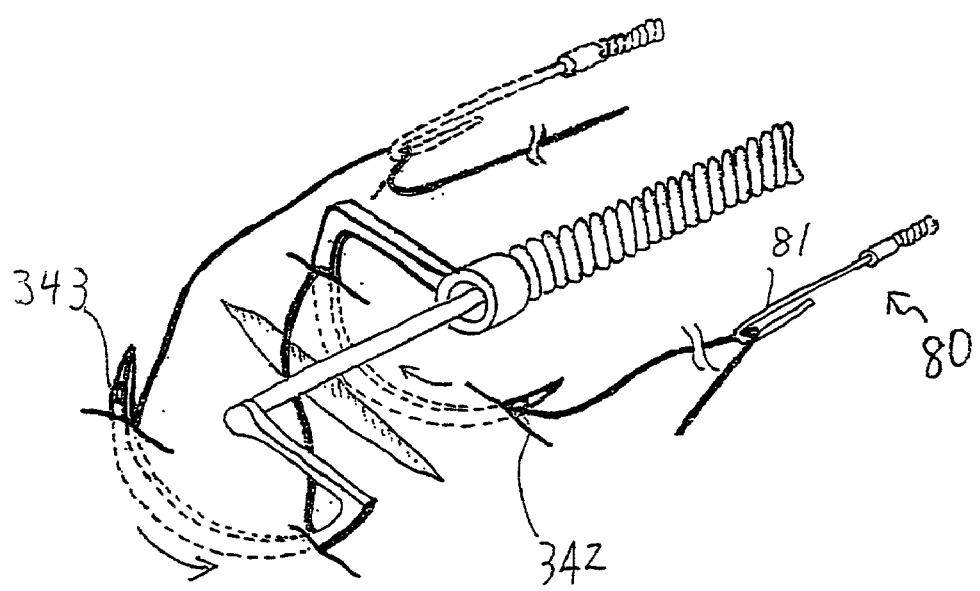

Then hook the thread 4 held by the needle holes 342 and 343 as shown in FIG. 110 onto the elongate member 81 of the thread grasping/withdrawing means 80 inserted via the instrument channel port 7 and pull the thread 4 toward the operator side.

Figure 111:
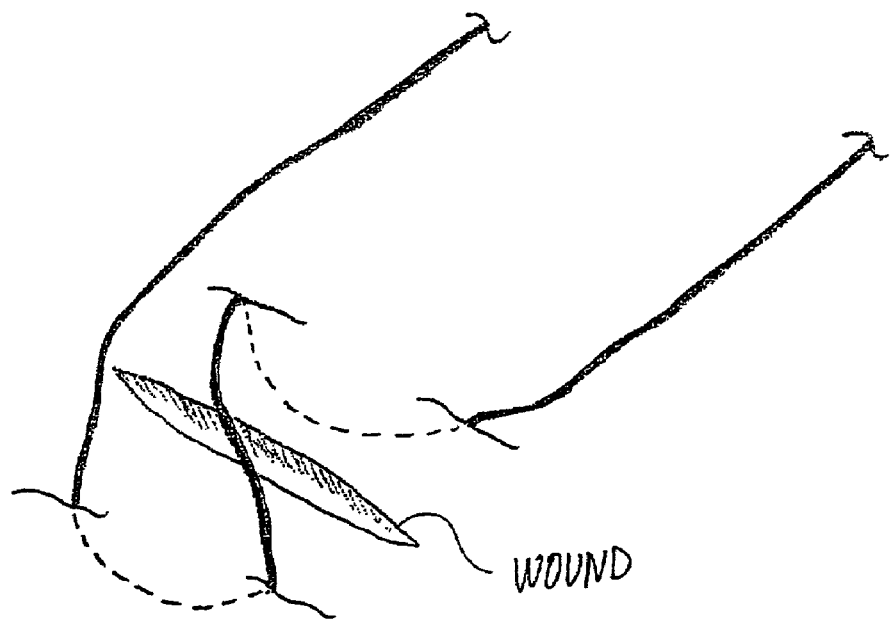

Reverse the curved needles 338 and 339 using the operation units as shown in FIGS. 110 and 111 to remove them from the tissue.

Use the thread as shown in FIG. 111 to make a knot as shown in FIG. 45 to complete the suturing procedure.

In addition to the advantages of the twentieth embodiment, suture threads may be fixed in a cross shape to further enhance suturing effects.

Embodiment 22

A twenty-second embodiment is shown in FIGS. 1 through 4 and 113 through 120 and 131 through 140 and 142. This embodiment is an improved version of the first embodiment, and a thread 348 is fixed to the needle's slit 18 on the curved needle 17 of the first embodiment.

Figure 113:
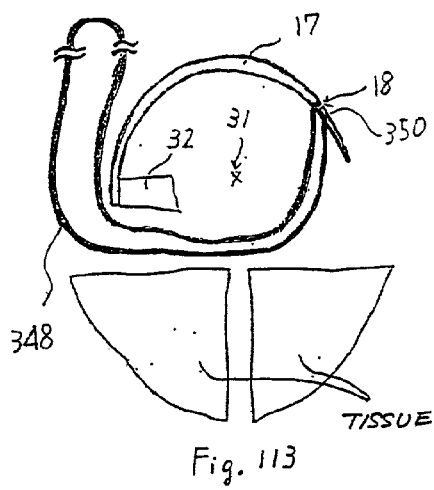
Figure 120:
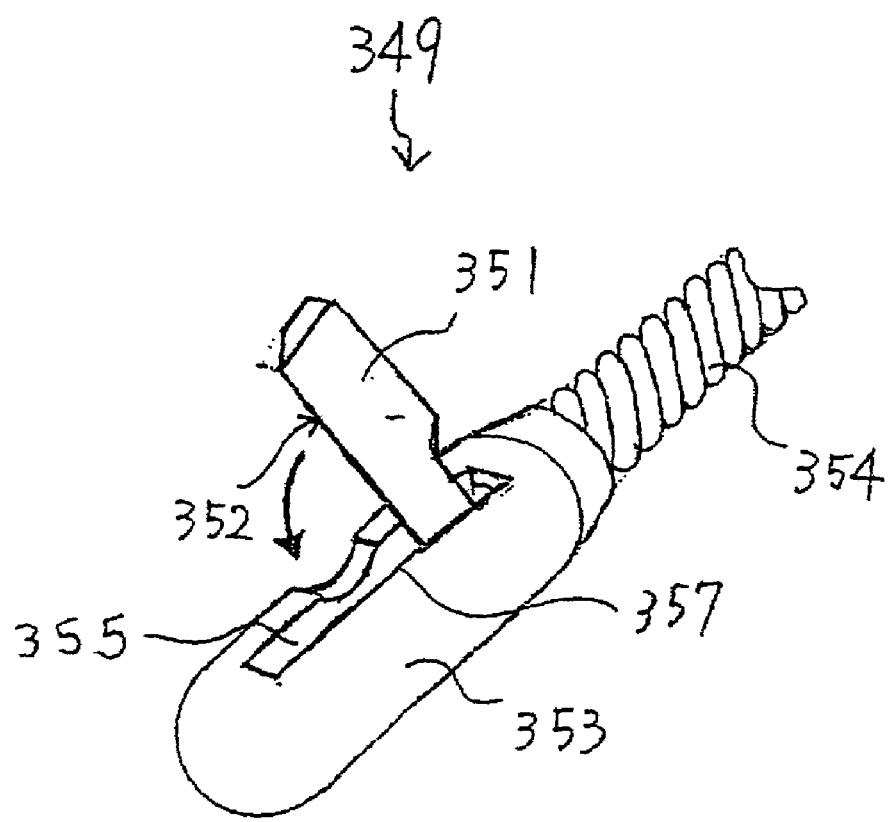

As shown in FIG. 113, a part of the thread 348 shaped in loop is fixed to the curved needle 17 with an adhesive or the like. Although a part of the thread 348 is fixed to the curved needle 17 with adhesive in the twenty-second embodiment, the thread 348 may be fixed to the curved needle 17 by other methods including calking. Although the thread grasping/withdrawing means 69 is disposed in the instrument channel port 7 in the first embodiment, a thread cutting/withdrawing means 349 is disposed therein as shown in FIG. 120 in the twenty-second embodiment. As shown in FIG. 120, the thread cutting/withdrawing means 349 comprises a coil 354, a supporting member 353 fixed at the distal end of the coil 354, a slit 355 formed on the supporting member 353, a cutting/holding member 351 having a width to pass through the slit 355, an operating wire, not shown in the figure, connected to the cutting/holding member 351 with a linkage, not shown in the figure, and moving back and forth in the coil 354, and an operation unit connected to the operator side of the operating wire and being similar to the thread grasping/withdrawing means 69 shown in FIG. 1.

Figure 121:
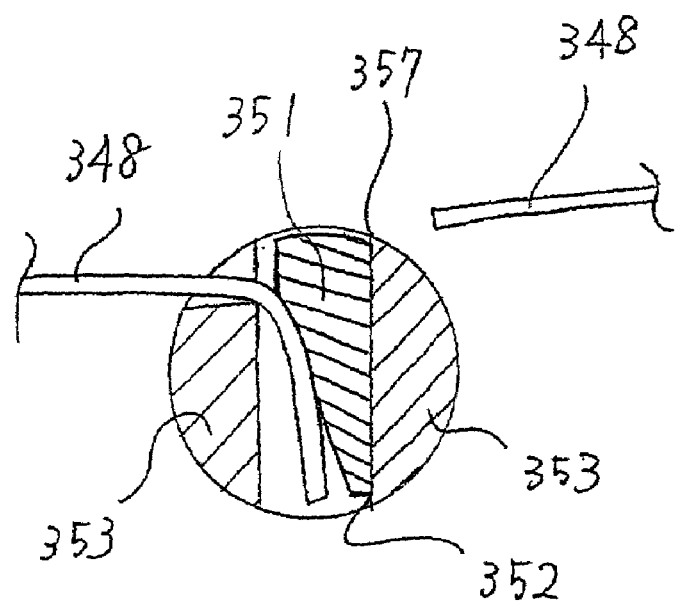

The thread cutting/withdrawing means 349 of the foregoing construction may rotate the cutting/holding member 351 via the operating wire and the linkage by advancing or withdrawing the handle 356 mounted on the operation unit on the operator side, and the thread is cut by sliding motion between the blades 352 and 357. One of the cut thread is caught by the cutting/holding member 351 and the supporting member as shown in FIG. 121. The blade is used as the cutting means in twenty-second embodiment, the thread may be cut by high frequency current or heating element.

Figure 128:
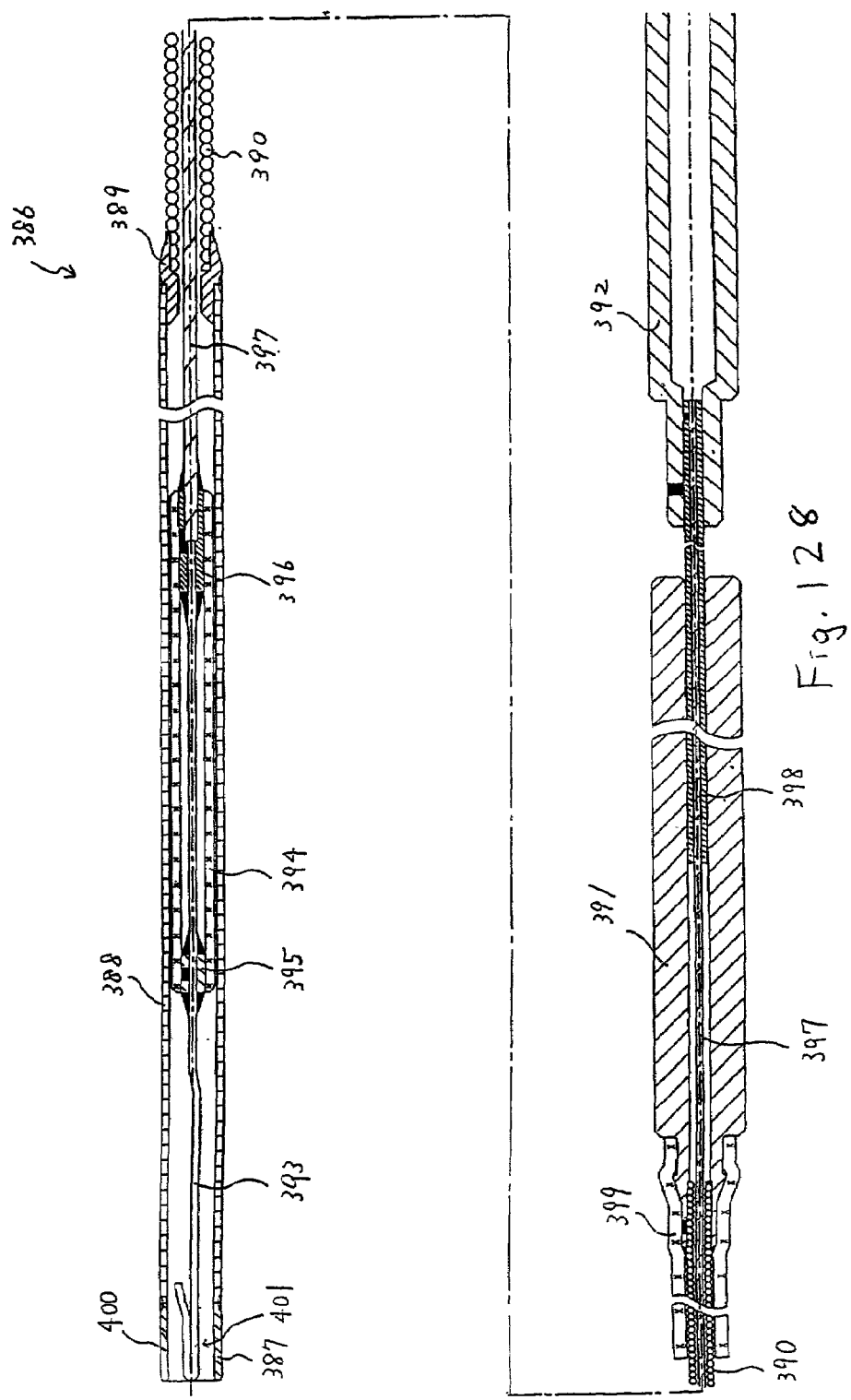

Means to cut and withdraw the thread may use the cutting/withdrawing method 386 as shown in FIG. 128. 386 has a tube tip 387 on which U-shape cutter 400 is formed, a coil sheath 388 fixed to the near end of 387, a connecting member 389 which connects 388 and the multicoil 390, a coil rotation handle 391 fixed to the near end of 390, a hook 393 which can removably fix the thread 348, a connecting member 396 which connects 393 and a torque wire 397, a pipe 398 fixed to the near end of 397, a handle 392 fixed to 398. Such construction of 386 enables to rotate 392 which sequentially rotates 401 and moving 392 back and forth sequentially pushes 401 out of 387. Moreover, 392 has a centering member 394 fixed to the guide member 395 and connecting member 396 to keep 401 on the center of axis. By doing so, it can be avoid that 401 is stuck to 387 which makes impossible to pulling it into the 388.

Figure 129:
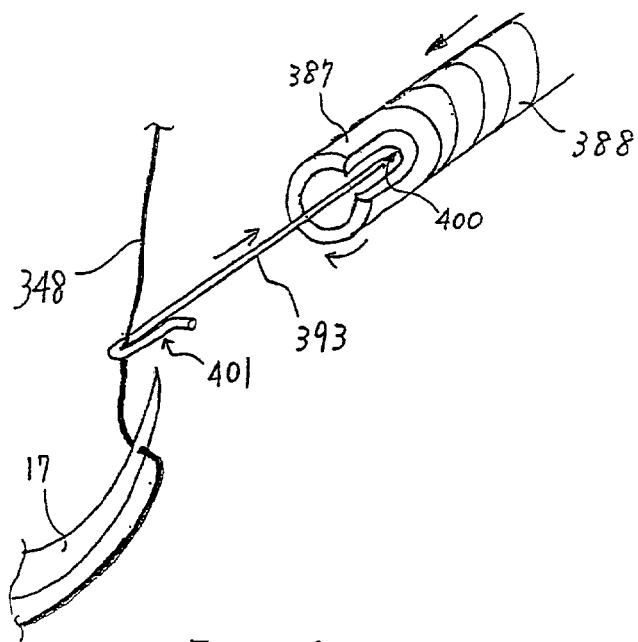
Figure 130:
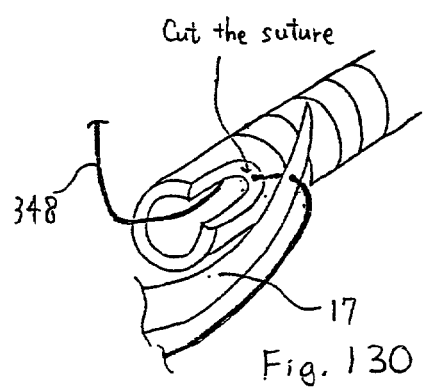
Figure 139:
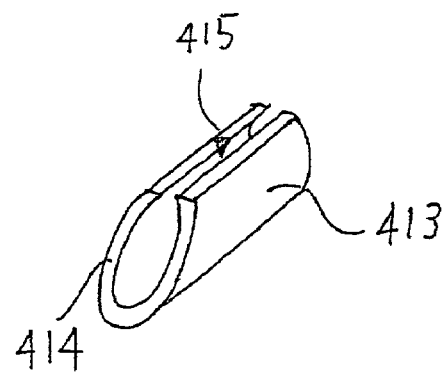
Figure 140:
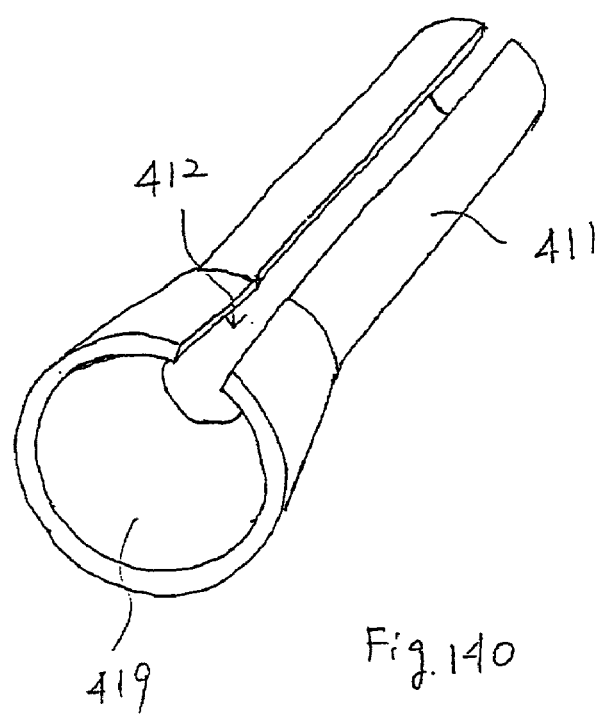

As shown in FIG. 129, after 348 is hooked by 401, the cutter 400 is faced to the curved needle 17 as turning 391 clockwise. Then 348 is cut by pulling 393 and pushing 388 at the same time as shown in FIG. 130. During this process, 401 keeps grasping one end of 348 so that it can be withdrawn by retrieving 386 to the operator side of endoscope.

Also the guiding member may be constructed on the suturing device to grasp 348 securely and automatically as shown in FIG. 131 through 140. The guiding member comprises a receiving portion 410 and active portion 418. 410 has a inner casing 413 adhered to the inside of the outer casing 411 by resin.

Casing 411 comprises a funnel-shape portion 419, which enables smooth insertion of 401, and a slit 412 where 393 and 348 can pass through, and a sheath to where 413 is fixed.

Figure 142:
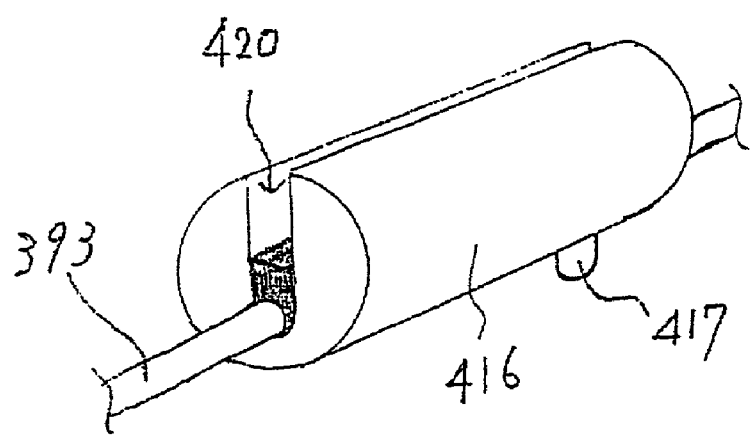

413 comprises a taper potion 414 similar to the tip end of a injection needle, a slit 415 which is larger than outer diameter of the pin 417 fixed to 416, a lumen of which inner diameter is larger than the outer diameter of sheath member 416. 418 comprises 416 and 417 with 393 is adhered to the slit 420 of 416 as shown in FIG. 142.

As shown in FIGS. 131 and 132, the guide member has a structure that 401 is inserted to 410 from 419 when 393 is pushed out of 387. Then as shown FIGS. 133 through 135, 139 and 142, 417 is in touch with 414 with 418 rotated when 393 is extruded further. It keeps rotating until 417 fits to 415, and 401 automatically faces the direction shown in FIG. 135.

Next, by pulling back 393 as shown in FIG. 136, it grasps a part of 348 fixed to 17.

Then 393 is pushed out again until 418 is out of 410 as shown in FIG. 137. As shown in FIG. 138, 393 is passed through 412 and 415 by moving the suturing device 3 or 405, and consequently 405 is separated from 410. By doing so, 401 grasps 348 automatically.

The operation of the twenty-second embodiment is described below by referring to FIGS. 113 through 119.

As shown in FIG. 113, fix the thread 348 to the curved needle 17 of the suturing device 3 set as shown in FIGS. 1 and 2 of the first embodiment. The thread 348 passes through the instrument channel port 7 and comes out of the operator side of the instrument channel port 7 as the thread 4 in FIG. 1.

Figure 114:
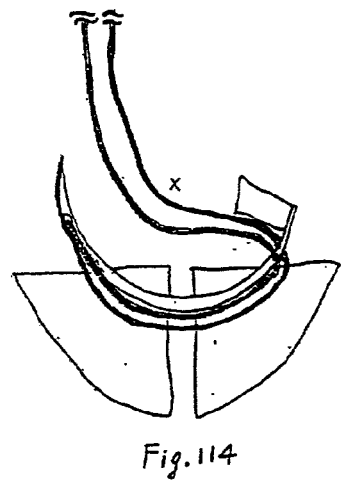

Press the suturing device 3 against the suturing site as shown in FIG. 114 and rotate the curved needle clockwise with the thread 348 fixed thereto to urge the curved needle 17 to cross the suturing site.

Figure 115:
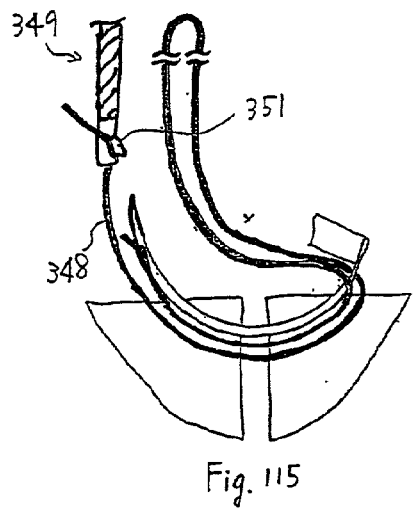

As shown in FIG. 115, use the thread cutting/withdrawing means 349 inserted in the instrument channel port 7 to cut the thread 348 fixed in the vicinity of the needle's slit 18 and hold one end of the cut thread 348 to remove from the body cavity.

Figure 116:
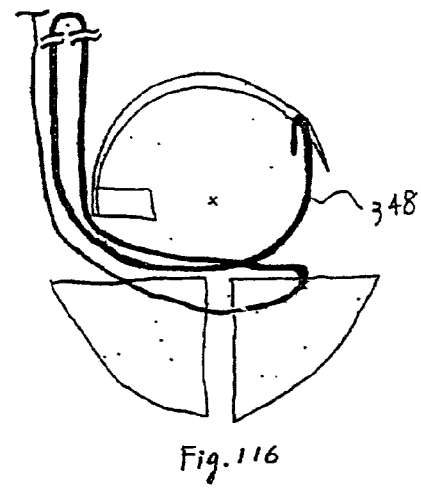

As shown in FIG. 116, rotate the curved needle 17 counterclockwise to remove the curved needle 17 from the tissue. Since the thread 348 is fixed to the curved needle 17, it does not come apart from the needle's slit 18.

Figure 117:
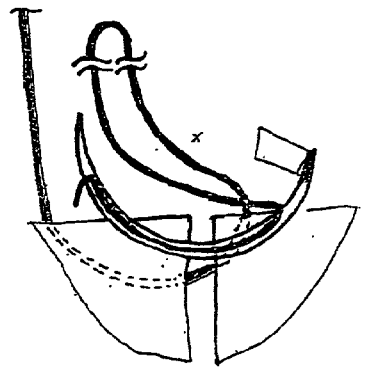
Figure 118:
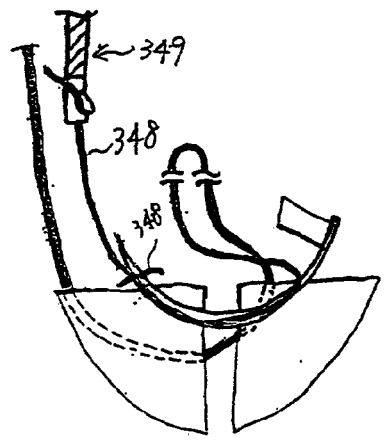

As shown in FIG. 117, adjust the angle of the endoscope to puncture the site slightly away from the previous suturing site, and cut and hold the other end of the thread 348 as in the step (3) as shown in FIG. 118 to remove it from the body cavity.

Figure 119:
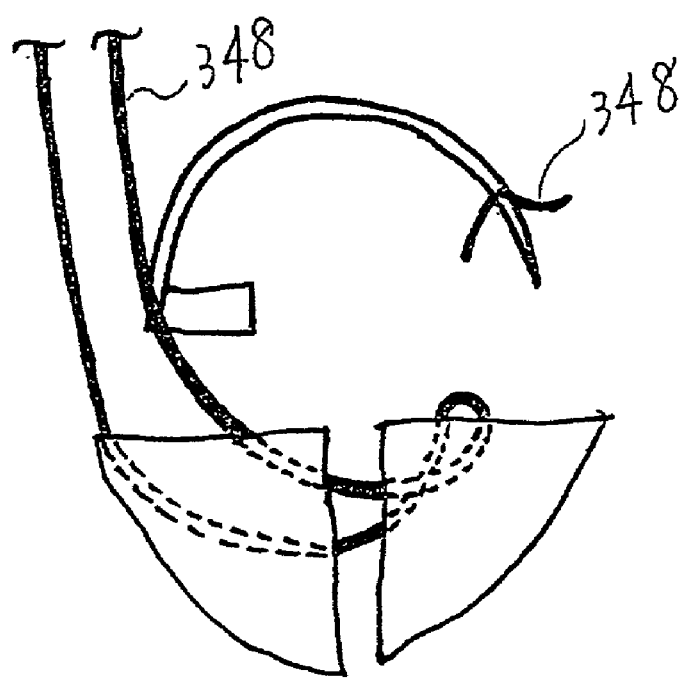

As shown in FIG. 119, rotate the curved needle 17 counterclockwise to remove it from the tissue. A part of the thread 348 remains fixed on the curved needle 17. Make a knot with the two ends of the thread 348 coming out of the body cavity as shown in FIG. 45 of the first embodiment to complete the suturing procedure.

In addition to the advantages of the first embodiment, the thread does not come apart from the curved needle since the thread is fixed to the curved needle, thus facilitating the suturing procedure. Since the thread fixed to the curved needle does not come apart from the curved needle during withdrawal of the thread to the operator side after puncture, the length of the thread may be made shorter than in the first embodiment. In short, since the thread on the X side moves along with the thread on the Y side in the direction shown with the arrow, the thread coming out of the instrument channel port 7 as shown in FIG. 1 should have enough length so that the end of the thread 4 does not enter the instrument channel port 7 during withdrawal of the thread by the thread grasping/withdrawing means 69. The twenty-second embodiment, on the other hand, should only have the length to make a knot on the operator side of the curved needle 7, thus saving the thread.

Embodiment 23

Figure 123:
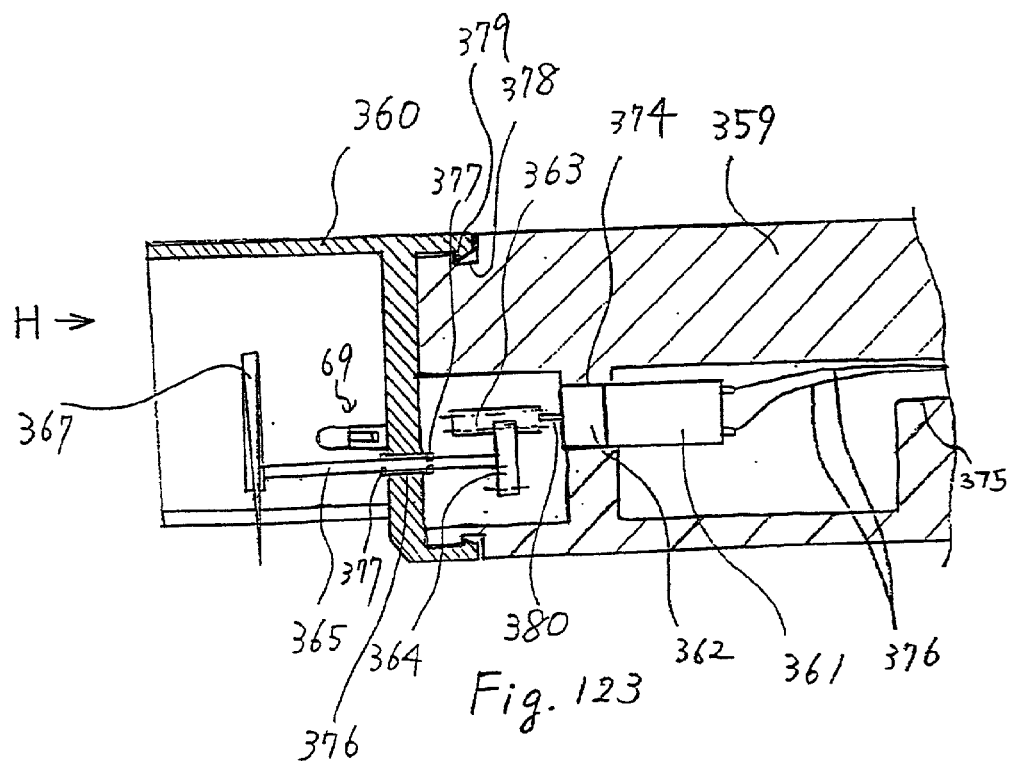
FIGS. 123 and 124 illustrate a twenty-third embodiment of the present invention.
Figure 124:
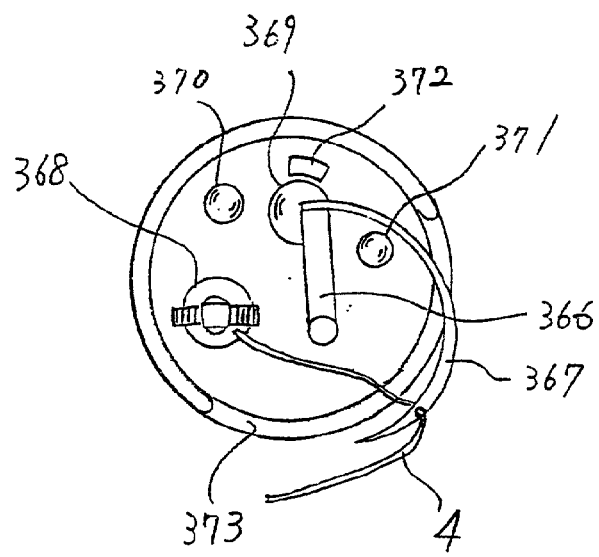

FIGS. 123 and 124 illustrate the twenty-third embodiment. FIG. 124 is the view taken from the arrow H of FIG. 123. As shown in FIG. 123, the twenty-third embodiment incorporates a motor 361 as a drive source for rotating a curved needle 367 in a flexible portion 359 of the endoscope, a small reducing gear 362 provided on the distal end of the motor like a planetary gear, and a gear 363 connected to the reducing gear 362 via a shaft 380. A tissue protective member 360 is detachably mounted on the distal end of the flexible portion 359. A stopper member 379 is formed on the operator side of the tissue protective member 360 and becomes engaged with a groove 378 formed at the distal end of the flexible portion 359 to enable detachment. A hole 375 is formed on the tissue protective member 360, and a shaft 365 is rotatably fitted in the hole 376. A gear 364 is fixed to the operator side of the shaft 365 to come to engagement with the gear 363, and a curved needle 367 is fixed at the distal end via an arm 366. Two stoppers 377 such as a C ring are fixed on the shaft 365 to catch the wall 360 from both sides to prevent axial movement.

As shown in FIG. 124, the distal end of the flexible portion 359 is provided with a CCD camera 369, light guides 370 and 371, an instrument channel 368, and a nozzle 372 for washing the lens of the CCD camera as in the first embodiment, and the thread 4 and the thread grasping/withdrawing means 69 are inserted through the instrument channel 368 as in the first embodiment.

The motor 361 is controlled by a motor controller disposed on the operator side by a wire 376 and not shown in the figure to rotate the curved needle in normal and reverse directions. The motor controller may have a built-in a microcomputer or the like.

In the twenty-third embodiment, the reducing gear 362 and the motor 361 may be fixed on the operator side of the flexible portion 359, and the shaft 380 and the reducing gear 362 may be connected by a flexible shaft with superior torque transmission.

The tissue protective member 360 including the curved needle 367, shaft 365, and gear 364 may be detached from the distal end of the flexible portion 359 so that the tissue protective member 360 alone may be washed, disinfected, or sterilized or may be made disposable.

Although the suturing procedure is same as in the twelfth embodiment, the rotation of the wire 376 is controlled with the motor controller.

In addition to the advantages of the first embodiment, the rotation of the curved needle is electronically controlled by using the motor, thus facilitating suturing operation. Since the unit 360 including the curved needle 367 is detachable, the washing and sterilizing quality will be enhanced.

The unit 360 including the curved needle 367 may be made disposable.

Needless to say the suturing devices shown in the first through twenty-third embodiments may be combined with each other.

All the parts shown in the first through twenty-third embodiments are made from metal or resin materials. The metal materials include stainless steel, aluminum, nickel, brass, titanium, iron, phosphor bronze, tungsten, gold, silver, and copper, and alloy of these metals. The resin materials include polysulfone, polyphenylsulfone, polyether amide, polytetrafluoroethylene (PTFE), tetrafluoroethylene parfluoro alcoxiethylene resin (PFA), tetrafluoroethylene hexafluoride propylene resin (FEP), POM, PEEK, polyolefine, polycarbonate, ABS, polyamide, vinyl chloride, latex, nylon, dichlorphin resin, and norbornen resin, or synthetic resin of these.

What is claimed is:

1. A suturing device comprising:
   a flexible elongated tubular member adapted to extend from a proximal end to a distal end of a flexible endoscope and to be bendable with the flexible endoscope;
   a needle for suturing which is adapted to pierce tissue and which is provided on a distal end of the flexible elongated tubular member separately from the flexible elongated tubular member;
   an engaging element provided on said needle so as to engage a suturing thread;
   a catching device provided at a distal end side of the suturing device for retrieving at least a portion of said suturing thread after the needle pierces the tissue;
   a wire which is adapted to operate the needle and which is provided in the flexible elongated tubular member; and
   a protective member which covers at least a part of the needle, and which includes an opening extending along both a front end portion of the protective member and one lateral side portion of the protective member;
   wherein the needle is rotatable to be positioned in: (i) a first state in which the needle is accommodated in the protective member, (ii) a second state in which a tip of the needle extends out from the front portion of the protective member through the opening, and (iii) a third state in which the tip of the needle extends out from said one side portion of the protective member through the opening.

2. The suturing device according to claim 1, wherein the flexible elongated tubular member comprises a flexible coil.

3. The suturing device according to claim 1, wherein the needle comprises a curved needle.

4. The suturing device according to claim 1, further comprising a tissue fixing member which is provided on the distal end side of the suturing device separately from the needle to prevent said suturing device from dislocating from a tissue to be sutured.

5. The suturing device according to claim 1, wherein the flexible endoscope includes a COD camera inside a distal end portion thereof.

6. The suturing apparatus according to claim 5, wherein the flexible elongated tubular member comprises a flexible coil.

7. The suturing device according to claim 1, wherein the flexible elongated tubular member is adapted to be inserted into a channel formed in the flexible endoscope.

8. A suturing device for use with a flexible endoscope, comprising:
   a body, which includes a flexible elongated tubular member, and which is adapted to extend from a proximal end to a distal end of the flexible endoscope and to be bendable with the flexible endoscope;
   a rotation axis provided at a distal end of the body;
   a rotatable curved needle for suturing which is adapted to pierce tissue and which is provided on the distal end of the body separately from the body;
   an engaging element provided on said needle so as to engage a suturing thread;
   a connecting member that supports the curved needle so that the needle is rotatable around the rotation axis without a guide through which the needle is moveable;
   a wire which is adapted to operate the needle and which is provided in the flexible elongated tubular member; and
   a catching device provided at a distal end side of the suturing device for retrieving at least a portion of said suturing thread after the needle pierces the tissue;
   wherein the suturing device is adapted to be combined with the flexible endoscope such that the needle is movable through a position in front of the distal end of the endoscope, at which position at least a portion of the needle is a distal-most element of the suturing device along a longitudinal direction of the suturing device.

9. The suturing device according to claim 8, further comprising a tissue fixing member which is provided on the distal end side of the suturing device separately from the needle to prevent said suturing device from dislocating from a tissue to be sutured.

10. The suturing device according to claim 9, further comprising a cover member adapted to be provided on the distal end of the flexible endoscope for covering at least a part of the needle.

11. The suturing device according to claim 9, wherein the flexible elongated tubular member is adapted to be inserted into a channel formed in the flexible endoscope.

12. The suturing device according to claim 8, wherein the flexible elongated tubular member comprises a flexible coil.

13. The suturing device according to claim 12, wherein the channel is provided on an outer surface of the endoscope.

14. The suturing device according to claim 8, wherein the flexible elongated tubular member is adapted to be inserted into a channel of the endoscope.

15. A suturing device for use with a flexible endoscope, comprising;
   a body, which includes a flexible elongated tubular member, and which is adapted to extend from a proximal end to a distal end of the flexible endoscope and to be bendable with the flexible endoscope;
   a rotatable member provided at a distal end of the body;
   a rotatable curved needle for suturing which is adapted to pierce tissue and which is provided on the distal end of the body separately from the body;
   an engaging element provided on said needle so as to engage a suturing thread;
   a connecting member which extends radially from the rotatable member and which supports the curved needle so that the needle is rotatable by rotation of the rotatable member;
   a wire which is adapted to operate the needle and which is provided in the flexible elongated tubular member; and
   a catching device provided at a distal end side of the suturing device for retrieving at least a portion of said suturing thread after the needle pierces the tissue;
   wherein the suturing device is adapted to be combined with the flexible endoscope such that the needle is positioned in front of the distal end of the endoscope.

16. The suturing device according to claim 15, wherein the needle is detachably coupled to the connecting member.

* * * * *